US012570971B2

(12) United States Patent
Steemers et al.

(10) Patent No.: US 12,570,971 B2
(45) Date of Patent: *Mar. 10, 2026

(54) CONTIGUITY PRESERVING TRANSPOSITION

(71) Applicant: Illumina Cambridge Limited, Essex (GB)

(72) Inventors: Frank J. Steemers, San Diego, CA (US); Kevin L. Gunderson, San Diego, CA (US); Fan Zhang, San Diego, CA (US); Jason Richard Betley, Essex (GB); Niall Anthony Gormley, Essex (GB); Wouter Meuleman, San Diego, CA (US); Jacqueline Weir, Essex (GB); Avgousta Ioannou, Essex (GB); Gareth Jenkins, Essex (GB); Rosamond Jackson, Essex (GB); Natalie Morrell, Essex (GB); Dmitry K. Pokholok, San Diego, CA (US); Steven J. Norberg, San Diego, CA (US); Molly He, San Diego, CA (US); Amirali Kia, San Diego, CA (US); Igor Goryshin, Madison, WI (US); Rigo Pantoja, San Diego, CA (US)

(73) Assignee: Illumina Cambridge Limited, Cambridge (GB)

( * ) Notice: Subject to any disclaimer, the term of this patent is extended or adjusted under 35 U.S.C. 154(b) by 765 days.

This patent is subject to a terminal disclaimer.

(21) Appl. No.: 17/719,276

(22) Filed: Apr. 12, 2022

(65) Prior Publication Data

US 2022/0282242 A1     Sep. 8, 2022

Related U.S. Application Data

(63) Continuation of application No. 16/173,202, filed on Oct. 29, 2018, now abandoned, which is a continuation of application No. 15/519,482, filed as application No. PCT/US2015/056040 on Oct. 16, 2015, now Pat. No. 11,873,480.

(60) Provisional application No. 62/242,880, filed on Oct. 16, 2015, provisional application No. 62/157,396, filed on May 5, 2015, provisional application No. 62/065,544, filed on Oct. 17, 2014.

(51) Int. Cl.
*C12Q 1/6806* (2018.01)
*C12N 15/10* (2006.01)
*C12Q 1/6874* (2018.01)
*C12Q 1/6876* (2018.01)

(52) U.S. Cl.
CPC ..... *C12N 15/1065* (2013.01); *C12N 15/1082* (2013.01); *C12N 15/1093* (2013.01); *C12Q 1/6806* (2013.01); *C12Q 1/6874* (2013.01);

*C12Q 1/6876* (2013.01); *C12Q 2600/154* (2013.01); *C12Q 2600/156* (2013.01); *C12Q 2600/172* (2013.01)

(58) Field of Classification Search
CPC ......... C12N 15/10; C12Q 1/68; C12Q 1/6806
See application file for complete search history.

(56) References Cited

U.S. PATENT DOCUMENTS

| | | | |
|---|---|---|---|
| 5,130,238 A | 7/1992 | Malek | |
| 5,185,243 A | 2/1993 | Ullman et al. | |
| 5,223,414 A | 6/1993 | Zarlinq et al. | |
| 5,455,166 A | 10/1995 | Walker | |
| 5,573,907 A | 11/1996 | Carrino et al. | |
| 5,599,675 A | 2/1997 | Brenner | |
| 5,641,658 A | 6/1997 | Adams et al. | |
| 5,679,524 A | 10/1997 | Nikiforov et al. | |
| 5,750,341 A | 5/1998 | Macevicz | |
| 5,858,671 A | 1/1999 | Jones | |
| 5,965,443 A | 10/1999 | Reznikoff et al. | |
| 6,210,891 B1 | 4/2001 | Nvren et al. | |
| 6,214,587 B1 | 4/2001 | Dattaqupta | |
| 6,258,568 B1 | 7/2001 | Murem | |
| 6,274,320 B1 | 8/2001 | Rothberg et al. | |
| 6,355,431 B1 | 3/2002 | Chee et al. | |
| 6,437,109 B1 | 8/2002 | Reznikoff et al. | |
| 6,593,113 B1 | 7/2003 | Tenkanen et al. | |
| 6,777,187 B2 | 8/2004 | Makarov et al. | |
| 6,828,098 B2 | 12/2004 | Langmore et al. | |
| 6,846,658 B1 | 1/2005 | Vaisvila et al. | |
| 7,001,792 B2 | 2/2006 | Sauer et al. | |
| 7,057,026 B2 | 6/2006 | Barnes et al. | |
| 7,115,400 B1 | 10/2006 | Adessi et al. | |
| 7,138,267 B1 | 11/2006 | Jendrisak et al. | |

(Continued)

FOREIGN PATENT DOCUMENTS

| | | |
|---|---|---|
| CN | 103443338 | 12/2013 |
| EP | 320308 | 11/1993 |

(Continued)

OTHER PUBLICATIONS

BR Office Action in Brazilian Appln. No. 1220210267812, dated Jun. 7, 2023, 12 pages (with English translation).

(Continued)

*Primary Examiner* — Amy M Bunker
(74) *Attorney, Agent, or Firm* — Fletcher Yoder, P.C.

(57) ABSTRACT

Embodiments provided herein relate to methods and compositions for preparing an immobilized library of barcoded DNA fragments of a target nucleic acid, identifying genomic variants, determining the contiguity information, phasing information, and methylation status of the target nucleic acid.

11 Claims, 76 Drawing Sheets

Specification includes a Sequence Listing.

(56) References Cited

U.S. PATENT DOCUMENTS

| | | | |
|---|---|---|---|
| 7,211,414 B2 | 5/2007 | Hardin et al. | |
| 7,244,559 B2 | 7/2007 | Rothberq et al. | |
| 7,315,019 B2 | 1/2008 | Turner et al. | |
| 7,329,492 B2 | 2/2008 | Hardin et al. | |
| 7,399,590 B2 | 7/2008 | Piepenburq et al. | |
| 7,405,281 B2 | 7/2008 | Xu et al. | |
| 7,537,897 B2 | 5/2009 | Brenner et al. | |
| 7,582,420 B2 | 9/2009 | Oliphant et al. | |
| 7,595,883 B1 | 9/2009 | El Gamal et al. | |
| 7,611,869 B2 | 11/2009 | Fan | |
| 7,670,810 B2 | 3/2010 | Gunderson et al. | |
| 7,696,340 B2 | 4/2010 | Goldman et al. | |
| 7,741,463 B2 | 6/2010 | Gormley | |
| 8,003,354 B2 | 8/2011 | Shen et al. | |
| 8,383,345 B2 | 2/2013 | Shendure et al. | |
| 8,563,477 B2 | 10/2013 | Smith et al. | |
| 8,829,171 B2 | 9/2014 | Steemers | |
| 9,074,251 B2 | 7/2015 | Steemers | |
| 9,644,198 B2 | 5/2017 | Walder et al. | |
| 9,644,199 B2 | 5/2017 | Belyaev | |
| 9,683,230 B2 * | 6/2017 | Gormley | C12Q 1/6834 |
| 10,557,133 B2 | 2/2020 | Steemers et al. | |
| 11,299,730 B2 | 4/2022 | Shendure et al. | |
| 11,319,534 B2 | 5/2022 | Steemers et al. | |
| 11,873,480 B2 | 1/2024 | Steemers et al. | |
| 2001/0046669 A1 | 11/2001 | Mccombie et al. | |
| 2002/0055100 A1 | 5/2002 | Kawashima et al. | |
| 2004/0002090 A1 | 1/2004 | Maver et al. | |
| 2004/0096853 A1 | 5/2004 | Mayer | |
| 2004/0110191 A1 | 6/2004 | Winkler et al. | |
| 2004/0259229 A1 | 12/2004 | Thevelein et al. | |
| 2005/0100932 A1 | 5/2005 | Lapidus et al. | |
| 2005/0191698 A1 | 9/2005 | Chee et al. | |
| 2006/0024681 A1 | 2/2006 | Smith et al. | |
| 2006/0040297 A1 | 2/2006 | Leamon et al. | |
| 2006/0216309 A1 | 9/2006 | Holden | |
| 2006/0236413 A1 | 10/2006 | Ivies | |
| 2006/0257905 A1 | 11/2006 | Freiji et al. | |
| 2006/0292611 A1 | 12/2006 | Berka et al. | |
| 2007/0128610 A1 | 6/2007 | Buzby | |
| 2007/0128624 A1 | 6/2007 | Gormley et al. | |
| 2008/0009420 A1 | 1/2008 | Schroth et al. | |
| 2008/0108082 A1 | 5/2008 | Rank et al. | |
| 2008/0234136 A1 | 9/2008 | Drmanac et al. | |
| 2008/0242560 A1 | 10/2008 | Gunderson et al. | |
| 2009/0026082 A1 | 1/2009 | Rothberg et al. | |
| 2009/0032401 A1 | 2/2009 | Ronaahi et al. | |
| 2009/0047680 A1 | 2/2009 | Lok | |
| 2009/0088331 A1 | 4/2009 | Wu et al. | |
| 2009/0127589 A1 | 5/2009 | RothberQ et al. | |
| 2009/0176234 A1 | 7/2009 | Dramanac et al. | |
| 2010/0022403 A1 | 1/2010 | Kurn et al. | |
| 2010/0069263 A1 | 3/2010 | Shendure et al. | |
| 2010/0111768 A1 | 5/2010 | Banerjee et al. | |
| 2010/0120098 A1 | 5/2010 | Grunenwald et al. | |
| 2010/0137143 A1 | 6/2010 | Rothberg et al. | |
| 2010/0222238 A1 | 9/2010 | Smith et al. | |
| 2010/0282617 A1 | 11/2010 | Rothberq | |
| 2011/0014657 A1 | 1/2011 | RiQatti et al. | |
| 2011/0059865 A1 | 3/2011 | Smith et al. | |
| 2011/0124518 A1 | 5/2011 | Cantor | |
| 2011/0311506 A1 | 12/2011 | Craig et al. | |
| 2012/0053063 A1 | 3/2012 | RiQatti et al. | |
| 2012/0065081 A1 | 3/2012 | Chee | |
| 2012/0129704 A1 | 5/2012 | Gunderson et al. | |
| 2012/0157322 A1 | 6/2012 | Myllykangas et al. | |
| 2012/0208705 A1 | 8/2012 | Steemers | |
| 2012/0208724 A1 | 8/2012 | Steemers | |
| 2012/0270305 A1 | 10/2012 | Reed et al. | |
| 2012/0316074 A1 | 12/2012 | Saxonov | |
| 2013/0005585 A1 | 1/2013 | Anderson et al. | |
| 2013/0017978 A1 | 1/2013 | Kavana et al. | |
| 2013/0203605 A1 * | 8/2013 | Shendure | C12N 15/1093 506/2 |
| 2013/0323732 A1 | 12/2013 | Anderson et al. | |
| 2013/0338042 A1 | 12/2013 | Shen et al. | |
| 2014/0079923 A1 | 3/2014 | Georae et al. | |
| 2014/0093916 A1 * | 4/2014 | Belyaev | C12N 11/06 435/177 |
| 2014/0194324 A1 | 7/2014 | Gormley | |
| 2014/0235506 A1 | 8/2014 | Hindson | |
| 2019/0276821 A1 | 9/2019 | Steemers et al. | |
| 2022/0213470 A1 | 7/2022 | Steemers et al. | |
| 2023/0183680 A1 | 6/2023 | Steemers et al. | |

FOREIGN PATENT DOCUMENTS

| | | | |
|---|---|---|---|
| EP | 336731 | 5/1994 | |
| EP | 439182 | 4/1996 | |
| EP | 2712931 | 4/2014 | |
| EP | 2635679 | 4/2017 | |
| JP | 2013/150611 | 8/2013 | |
| JP | 2013/535986 | 9/2013 | |
| JP | 2014506788 | 3/2014 | |
| RU | 2252964 | 5/2005 | |
| WO | WO 1989/09835 | 10/1989 | |
| WO | WO 1989/10977 | 11/1989 | |
| WO | WO 1989/12696 | 12/1989 | |
| WO | WO 1990/01069 | 2/1990 | |
| WO | WO 1991/006678 | 5/1991 | |
| WO | WO 1995/23875 | 9/1995 | |
| WO | WO 1998/44151 | 10/1998 | |
| WO | WO 2004/018497 | 3/2004 | |
| WO | WO 2004/042078 | 5/2004 | |
| WO | WO 2005/065814 | 7/2005 | |
| WO | WO 2005/100585 | 10/2005 | |
| WO | WO 2006/047183 | 10/2005 | |
| WO | WO 2007/098279 | 8/2007 | |
| WO | WO 2007/123744 | 11/2007 | |
| WO | 101432439 A | 5/2009 | |
| WO | WO 2010/002883 | 1/2010 | |
| WO | WO 2010/048605 | 4/2010 | |
| WO | WO 2011/106314 | 9/2011 | |
| WO | WO 2012/025250 | 3/2012 | |
| WO | WO 2012/048341 | 4/2012 | |
| WO | WO 2012/058096 | 5/2012 | |
| WO | WO 2012/061832 | 5/2012 | |
| WO | WO 2012/103545 | 8/2012 | |
| WO | WO 2012/106546 | 8/2012 | |
| WO | WO 2012/108864 | 8/2012 | |
| WO | WO 2013/131962 | 9/2013 | |
| WO | WO-2013131962 A1 * | 9/2013 | C12Q 1/6806 |
| WO | WO 2013/177220 | 11/2013 | |
| WO | WO 2013/184796 | 12/2013 | |
| WO | WO 2014/108810 | 7/2014 | |
| WO | WO 2014/142850 | 9/2014 | |
| WO | WO 2014/189957 | 11/2014 | |
| WO | WO 2015/031691 | 3/2015 | |
| WO | WO 2015/103339 | 7/2015 | |
| WO | WO 2014/136930 | 2/2017 | |

OTHER PUBLICATIONS

AU Office Action in Australian Appln. No. 2022201205, mailed on Nov. 30, 2023, 3 pages.

JP Office Action in Japanese Appln. No. 2022-129859, mailed on Sep. 5, 2023, 8 pages (with English translation).

CA Office Action in Canadian Appln. No. 2,964,799, mailed on Dec. 22, 2023, 3 pages.

CN Office Action in Chinese Appln. No. 202111171107.9, mailed on Mar. 1, 2024, 15 pages (with English translation).

Cline et al., "PCR fidelity of pfu DNA polymerase and other thermostable DNA polymerases," Nucleic Acids Research, Sep. 1, 1996, 24(18):3546-51.

Pérez-Arnaiz et al., "Functional Importance of Bacteriophage φ29 DNA Polymerase Residue Tyr148 in Primer-terminus Stabilisation at the 3'-5' Exonuclease Active Site," Journal of Molecular Biology, Sep. 4, 2009, 391(5):797-807.

Silander et al., "Whole genome amplification with Phi29 DNA polymerase to enable genetic or genomic analysis of samples of low DNA yield," Genomics Protocols, 2008:1-8.

(56)     References Cited

OTHER PUBLICATIONS

CA Office Action in Canadian Appln. No. 2,964,799, dated Nov. 9, 2022, 4 pages.
EP Office Action in European Appln. No. 19183798.8, mailed on Sep. 26, 2024, 7 pages.
JP Office Action in Japanese Appln. No. 2022-129859, mailed on Feb. 6, 2024, 5 pages (with English translation).
RU Office Action in Russian Appln. No. 2020137454, mailed on Apr. 24, 2024, 7 pages (with English translation).
Adey, et al., "Rapid, low-input, low-bias construction of shotgun fragment libraries by high-density in vitro transposition", Genome Biology, vol. 11:R119, Dec. 8, 2010, 47 pages.
Adey, et al., "Ultra-low-input, tagmentation-based whole-genome bisulfite sequencing", Genome Research, vol. 22, No. 6, Mar. 30, 2012 (Mar. 30, 2012), XP055136909; ISN: 1088-9051, DOI: 10.1101/qr.136242.111, 1139-1143.
Amini, et al., "Haplotype-resolved whole-genome sequencing by contiguity-preserving transposition and combinatorial indexing", Nature Genetics, vol. 46 No. 12, Dec. 2014, 1343-1349.
Amini, et al., "Supplementary information for:Haplotype-resolved whole-genomes sequencing by contiguity-preserving transposition and combinatorial indexing", Nature Genetics, vol. 46 No. 12, Dec. 2014, 1-16 XP-002753799.
AU Office Action in Australian Application No. 2015331739, dated Dec. 10, 2020, 5 pages.
Bains, et al., "A novel method for nucleic acid sequence determination", J. Theor Biol., (1988) 135, 303-307.
Ball, et al., "Targeted and genome-scale strategies reveal gene-body methylation siQnatures in human cells", Nature BiotechnoloQy 27(4), Apr. 2009, 361-368.
Bansal, et al., "HapCUT: an efficient anA1l:A17lrithm for the haplotype assembly problem", Bioinformatics;24(16), (2008) 1153-1159.
Batzoglou, et al., "ARACHNE: A Whole-Genome Shotgun Assembler", Genome Research, 12:177-189 (2002).
Benetti, et al., "A mammalian microRNA cluster controls DNA methylation and telomere recombination via Rbl2-dependent regulation of DNA methyltransferases.", Nat Struct & Mol Bio 15(3), Mar. 2008, 268-279.
Bentley, et al., "Accurate whole human genome sequencing using reversible terminator chemistry", Nature, vol. 45616, Nov. 20081 doi:10.1038/nature075177218, Nov. 6, 2008, 53-59.
Bimber, et al., "Whole-Genome Characterization of Human and Simian Immunodeficiency Virus Intrahost Diversity by Ultradeep Pyrosequencing", Journal of Virol0QY, vol. 84, No. 22, 2010, 12087-12092 DOI: 10.1128/JVI.01378-10.
Bloch, et al., "Purification of Escherichia coli Chromosomal Segments without Cloning", Biochemical and Biophysical Research Communications, vol. 223, 1996, 104-111.
Boeke, et al., "Transcription and Reverse Transcription of Retrotransposons", Annu Rev Microbial 43, 1989, 403-34.
BR Office Action in Brazilian Appln. No. BR112015016005-0, dated Sep. 24, 2019, 7 pages (with English translation).
BR Office Action in Brazilian Appln. No. BR112017007912-7, dated Apr. 20, 2020, 10 pages (with English Translation).
Branton, et al., "The potential and challenges of nanopore sequencing", Nature Biotechnoloqy, vol. 26, No. 10, Oct. 2008, 1146-1153.
Braslavsky, et al., "Sequence information can be obtained from single DNA molecules", PNAS, 100(7). Epub Mar. 21, 2003., Apr. 1, 2003, 3960-3964.
Brown, et al., "Retroviral integration: Structure of the initial covalent product and its precursor, and a role for the viral IN protein", Proc. Natl. Acad. Sci. USA 86 (1989).
Brownlie, et al., "The Caenorhabditis briggsae genome contains active CbmaT1 and Tcb 1 transposons", Molecular Genetics and Genomics, vol. 273, 2005, 92-101.
CA Application No. 2,898,456, Office Action dated Jul. 27, 2018, 5 pages.
CA Office Action in Canadian Appln. No. 2,964,799, dated Jan. 12, 2022, 4 pages.
Caruccio, et al., "Preparation of Next-Generation Sequencing Libraries Using Nextera(TM) Technology: Simultaneous DNA Fragmentation and Adaptor Tagging by in Vitro Transpoition", Methods in Molecular Biology, 733, Jan. 1, 2011, 241-255.
Chernoff, et al., "Molecular Analysis of the von Hippel-Lindau Disesase Gene", Methods. Mol. Med. 53, 2001, 193-216.
Choi et al., "Applications of transposon-based gene delivery system in bacteria," Journal of Microbiology and Biotechnology, Jan. 2009, 19(3):217-28.
Clark, et al., "High sensitivity mapping of methylated cytosines", Nucleic Acids Research, vol. 22, No. 15, 1994, 2990-2997.
CN Chinese Office Action, Application No. 201280012945.4, mailed Apr. 17, 2015.
CN Chinese Office Action, Application No. CN201280012945.4 with English Translations, State Intellectual Property Office, PRC China, Nov. 6, 2015, 21 pages.
CN Chinese Office Action, Application No. CN201280012945.4, mailed May 28, 2014.
CN Office Action in Chinese Appln. No. 201580068116.1, dated Apr. 8, 2021, 12 pages (with English translation).
CN Office Action in Chinese Appln. No. 201580068116.1, dated Sep. 11, 2020, 21 pages (with English translation).
Cockroft, et al., "A Single-Molecule Nanopore Device Detects DNA Polymerase Activity With Single-Nucleotide Resolution", J. Am. Chem. Soc, 130(3), Jan. 23, 2008, 818-820.
Cokus, et al., "Shotgun bisulphite sequencing of the Arabidopsis genome reveals DNA methylation patterning", Nature 452113 Mar. 20081 doi: 10.1038/nature06745, 215-219.
Colegio, et al., In Vitro Transposition System for Efficient Generation of Rrandom Mutants of Camovlobacter ieiunl, J. Bacterial, 183, No. 7, Apr. 2001, oo. 2384-2388.
Craig, N.L., "Transposon Tn7", Howard Hughes Medical Institute, Department of Molecular Biology and Genetics. 615 PCTB, 725 North Wolfe Street, Johns Hopkins School of Medicine, Baltimore, MD 21205, USA, Review in: Curr Top Microbial Immunol, 204, 1996, 27-48.
Craig, N.L., "V(D)J Recombination and Transposition: Closer Than Expected", Science, 271, Mar. 1996, p. 1512.
De Vries, et al., "PCR on Cell Lysates Obtained from Whole Blood Circumvents DNA Isolation", Clin. Chem. 47, No. 9, 2001, 1701-1702.
Deamer, et al., "Characterization of Nucleic Acids by Nanopore Analysis", ACC Chem Res, 2002, 35(10), 817-825.
Deamer, et al., "Nanopores and nucleic acids: prospects for ultrarapid sequencing", Trends Biotechnol, vol. 18, No. 4, 2000, 147-151.
Dean, et al., Comprehensive human genome amplification using multiple.
Deng, et al., "Targeted bisulfite sequencing reveals changes in DNA methylation associated with nuclear reprogramming.", Nat Biotechnol 27(4), Apr. 2009, 353-360.
Dienekes et al., "Anthropology Blog, ASHG 2014 Titles and Abstracts," Book of Abstracts of the 64th Annual Meeting of the American Society of Human Genetics, Oct. 18-22, 2014 in Sep. 2014, San Diego, California, 14 pages.
Down, et al., "A Bayesian deconvolution strategy for immunoprecipitation-based DNA methylome analysis," Nat Biotechnol 26(7), Jul. 2008, 779-785.
Dressman, et al., "Transforming single DNA molecules into fluorescent magnetic particles for detection and enumeration of genetic variations", PNAS, 100(15), Jul. 22, 2003, 8817-8822.
Drmanac, et al., "Accurate sequencing by hybridization for DNA diagnostics and individual Qenomics", Nature BiotechnoloQy, 16(1), 1998, 54-8.
Drmanac, et al., "Human Genome Sequencing Using Unchained Base Reads on Self-Assembling DNA Nanoarrays", Sciencexpress, Nov. 5, 2009; 10.1126/Science.1181498.
Duan, et al., "A three-dimensional model of the yeast genome", Nature; 465(7296), May 2010, 363-7.
Duitama, et al., "ReFHap: A Reliable and Fast Algorithm for Single Individual Haplotyping", Proceedings of the First ACM International Conference on Bioinformatics and Computational Bioloav, 160-169, 2010.

(56) References Cited

OTHER PUBLICATIONS

Eid, "Real-Time DNA Sequencing from Single Polymerase Molecules", Science 323, 2009, 133-138.

EP Application No. 15797490.8, Communication Under Rule 164(2)(a) EPC, dated Jun. 21, 2018, 8 pages.

EP Communication pursuant to Article 94(3) EPC in 12741945.5, Oct. 26, 2015.

EP Communication pursuant to Article 94(3) EPC, mailed Oct. 28, 2014, for APPiication No. 11802179.9.

EP European Patent Office, Communication Pursuant to Article 94(3) for application No. 15797490.8, Jan. 10, 2018.

EP European Patent Office, Extended European Search Report for application No. 18198695.1, Feb. 18, 2019.

EP Extended European Search Report in EP Appln. No. 19183798.8, dated Mar. 12, 2020, 16 pages.

Ewing, et al., "Base-CalIng of Automated Sequencer Traces UsingPhred.?11. Error? Probabilities", Genome Research, 8, 1998, 186-194.

Fan, et al., "Whole-genome molecular haplotyping of single cells.", Nat Biotech 29(1):, Jan. 2011, 51-57.

Filee et al., "Insertion sequence diversity in Archaea," Microbial. Mal. Biol. Rev. 2007, 71(1), 121-157.

Fisher et al., "Abstract 1698S, Contiguity Preserving Transposition Sequencing (CPT-seq): Haplotype-Resolved Sequencing and Assembly," Book of Abstracts, 64th Annual Meeting of the American Society of Human Genetics, Oct. 18-22, Sep. 2014, San Diego, California, 2 pages.

Fodor, et al., "Light-Directed, Spatially Addressable Parallel Chemical Synthesis", Science, vol. 251, Feb. 15, 1991, 767-773.

Fullwood, et al., "An Oestrogen-Receptor a-bound Human Chromatin Interactome", Nature 462(7269), Nov. 5, 2009, 58-64.

Fullwood, et al., "Chromatin Interaction Analysis Using Paired-End Tag Sequencing", Current Protocols in Molecular Biology, Supplement 89, Jan. 21, 2010, 21.15.1-21.15.25.

Gal, et al., "Directional cloning of native PCR products with preformed sticky ends (autosticky PCR)" Molecular & General Genetics, vol. 260, No. 6, Jan. 1999, 569-.

Geiss, et al., "Direct multiplexed measurement of gene expression with color-coded probe pairs", Nat Biotechnol.; 26(3), Mar. 2008, 317-25.

Gloor, "Gene targeting in Drosophila", Methods Mol Biol. 260, 2004, 97-114.

Gnerre, "High-quality draft assemblies of mammalian genomes from massively parallel sequence data", Proc Natl Acad Sci USA., [Epub ahead of print] PubMed PMID: 21187386, Dec. 27, 2010.

Goodman, "Identifying genetic determinants needed to establish a human gut symbiont in its habit", Cell Host & Microbe, vol. 6, Sep. 2009, 279-289.

Goryshin et al., "Tn5/IS50 target recognition," Proceedings of the National Academy of Sciences, Sep. 1, 1998, 95(18):10716-21.

Goryshin, "Tn5 in Vitro Transposition", J. Biol. Chem. vol. 273, No. 13, Issue of Mar. 27, 1998, 7367-7374.

Grunenwald, "Nextera PCR-Free DNA Library Preparation for Next-Generation Seauencina", (Poster Presentation, AG8T)., 2011.

Grunenwald, "Rapid, high-throughput library preparation for next-generation sequencing, Nature Methods, Application Notes", Aug. 2010, iii-iv GS FLX Titanium LV emPCR Kit (Lib-L) protocol, Aug. 2008, 1-2.

Gu, "Preparation of reduced representation bisulfite sequencing libraries for genome-scale DNA methylation profilini::i", Nat Protoc 6(4), 2011, 468-481.

Haapa, "An efficient and accurate integration of mini-Mu transposons in vitro: a general methodology for functional genetic analysis and molecular biology applications", Nucleic Acids Research vol. 27, No. 13, 1999, 2777-2784.

Handelsman, "Metagenomics: Application of Genomics to Uncultured Microorganisms", Microbiology and Molecular Biology Reviews, 68(4), Dec. 2004, 669-685.

Harris, "Comparison of sequencing-based methods to profile DNA methylation and identification of monoallelic epigenetic modifications.", Nat Biotechnol28(10), 2010, 1097-1105.

Head et al., "Library construction for next-generation sequencing: overviews and challenges," Biotechniques, Feb. 2014, 56(2):61-77.

Healy, "Nanopore-based single-molecule DNA analysis", Nanomed. 2(4), 2007, 459-481.

Heredia, "In vitro double transposition for DNA identification", Analytical Biochemistry 399, 2010, 78-83.

Hiatt, "Parallel, tag-directed assembly of locally derived short sequence reads", Nat Methods. 7(2), 2010, 119-22 Nextera TM DNA Sample Prep Kits, printed on Feb. 13, 2012, 1 pg., htto://www.eoibio.com/nextera.

Ichikawa, "In vitro transposition of transposon Tn3", J Biol Chem, 265, 1990, 18829-32.

IL Office Action in Israeli Appln. 251737, dated Feb. 25, 2020, 9 pages (with English translation).

IL Office Action in Israeli Appln. 251737, dated Jul. 27, 2020, 4 pages (with English translation).

IN Hearing Notice in Indian Appln. No. 201717017016, dated Sep. 2, 2021, 3 pages (English translation).

IN Office Action in Indian Appln. No. 201717017016, dated Nov. 12, 2020, 7 pages.

IN Office Action in Indian Appln. No. 6953/DELNP/2015, dated Oct. 24, 2019, 8 pages (with English translation).

Ivics et al., "Targeted Sleeping Beauty transposition in human cells," Mal. Ther. 2007, 15(6), 1137-1144.

Jackson, "Plasmid tagging for efficient large-scale sequence completion of entire clone inserts", BioTechniques, vol. 34, Mar. 2003,604-608.

Johnson et al., "DNA sequences at the ends of transposon Tn5 required for transposition," Nature 1983, 304(5923), 280-282.

Johnson, "Genome-wide mapping of in vivo protein-DNAinteractions", Science. 316(5830)., 2007, 1497-502.

Joos, "Covalent attachment of hybridizable oligonucleotides to glass supports", Analytical Biochemistry, 247, 1997, 96-101.

JP Decision to Grant in Japanese Appln. No. 2018-232885, dated Mar. 22, 2021, 4 pages (with English translation).

JP Japanese Office Action in Japanese Appln. No. 2017-520884, dated Oct. 29, 2019, 11 pages (with English Translation).

JP Japanese Office Action in Japanese Appln. No. 2020-204004, dated Jan. 4, 2022, 10 pages (with English translation).

JP Office Action for JP213-552641 with English Translations, Jan. 12, 2016, 7 pages.

JP Office Action in Japanese Patent Application No. 2017-520884, dated Jun. 9, 2020, 7 pages (with English language translation).

JP Office Action in Japanese Patent Application No. 2018-232885, Dec. 24, 2019, 5 pages (with English translation).

Keith, "Algorithms for Sequence Analysis via Mutagenesis", Bioinformatics, vol. 20 No. 15; published online doi: 10.1093/bioinformatics/bth258, May 14, 2004, 2401-2410.

Keith, "Unlocking Hidden Genomic Sequence", Nucleic Acids Research, vol. 32, No. 3, published online DOI: 10.1093/nar/qnh022, Feb. 18, 2004, e35.

Khandjian, "UV crosslinking of RNA to nylon membrane enhances hybridization sianals", Mol. Bio. Rep, 11, 1986, 107-115.

Kidd, "Mapping and sequencing of structural variation from eight human genomes", Nature. 453 (7191), 2008, 56-64.

Kirby, "Cryptic plasmids of Mycobacterium aviumL Tn552 to the rescue", Molecular Microbiol0QY, 43, 2002, 173-86.

Kirby, "in vivo mutagenesis using EZ-Tn5"TM.", Methods in Enzymology, vol. 421, paQes 17-21 (2007).

Kitzman, "Hapiotype-resolved genome sequencing of a Gujarati Indian individual", Nature Biotechnology, vol. 29(1), Jan. 2011, 59-63.

Kleckner, "Tn10 and IS10 transposition and chromosome rearrangements: mechanism and regulation in vivo and in vitro", Curr Top Microbial Immunol., 204, 1996, 49-82.

Korlach, "Selective aluminum passivation for targeted immobilization of single DNA polymerase molecules in zero-mode waveguide nanostructures", PNAS, 105(4), 2008, 1176-1181.

KR Office Action in Korean Appln. No. 10-2015-7018788, dated Mar. 13, 2020, 14 pages (with English translation).

(56)                   References Cited

OTHER PUBLICATIONS

KR Office Action in Korean Appln. No. 10-2017-7013242, dated Dec. 28, 2021 8 pages (with English translation).

Kramer, "cDNA Library Construction from Single Cells", Current Protocols in Neuroscience, 2002, 4.27.1-4.27.19.

Lage, "Whole genome analysis of genetic alterations in small DNA samples using hyperbranched strand displacement amplification and array-CGH", Genome Research, vol. 13., Issue 2, Feb., Feb. 2003, 294-307.

Lai, "A shotgun optical map of the entire Plasmodium falciparum genome.", Nat Genet. 23(3), 1999, 309-13.

Lamble et al., "Improved workflows for high throughput library preparation using the transposome-based Nextera system," BMC Biotechnology, Dec. 2013, 13(1):1-0.

Lampe, "A purified mariner transposase is sufficient to mediate transposition in vitro", EMBO J., 15, 1996, 5470-5479.

Lander, "Initial sequencing and analysis of the human genome", Nature, 409(6822), 2001, 860-921.

Law Insider, All or Substantially All Legal Definition, Law Insider, 2020, obtained from https://www.lawinsider.com/dictionary/all-or-substantially-all on Oct. 2, 2020. (Year: 2013), 4 pages.

Lehoux et al., "Defined oligonucleotide tag pools and PCR screening in signature-tagged mutagenesis of essential genes from bacteria," Biotechniques 1999, 26(3), 473-478, 480.

Leshziner et al., "Tn552 Transposase Catalyzes Concerted Strand Transfer in vitro," Proc. Natl. Acad. Sci. USA 1998, 95, 7345-7350.

Levene, "Zero-Mode Waveguides for Single-Molecule Analysis at high concentrations", Science 299, 2003, 682-686.

Levy, "The Diploid Genome Sequence of an Individual Human", PLoS Biology, vol. 5, Issue 10, Oct. 2007, 2113-2144.

Li, "De novo assembly of human genomes with massively parallel short read sequencinq", Genome Res. 20 (2), 2010, 265-72.

Li, "DNA molecules and configurations in a solid-state nanopore microscope", Nature Mater, 2(9), 2003, 611-615.

Li, "Fast and accurate short read alignment with Burrows-Wheeler transform", Bioinformatics 25: 1754-1760, 2009.

Li, "Primase-based whole genome amplification", Nucleic Acids Res. 36(13), 2008, e79.

Li, "The DNA methylome of human peripheral blood mononuclear cells", PLoS Bioi 8(11), 2010, e1000533.

Lieberman-Aiden, "Comprehensive mapping of long-range interactions reveals folding principles of the human aenome", Science. 326(5950), 2009, 289-93.

Lim, "Shotgun optical maps of the whole *Escherichia coli* 0157:H7 genome", Genome Res. 11(9), 2001, 1584-93.

Lin, "Whole genome shotgun optical mapping of Deinococcus radiodurans," Science. 285(5433):, 1999, 1558-62.

Lister, "Human DNA methylomes at base resolution show widespread epigenomic differences", Nature, 462(7271), Nov. 19, 2009, 315-322.

Lizardi, "Mutation detection and single-molecule counting using isothermal rolling- circle amplification", Nature Genetics, vol. 19, 1998, 225-232.

Lundquist, "Parallel confocal detection of single molecules in real time", Opt. Lett. 33(9), 2008, 1026-1028.

Mahillon et al., "Insertion Sequences," Microbial. Mal. Biol. Rev. 1998, 62(3), 725-774.

Mardis, "Next-generation DNA sequencing methods", Annual Review of Genomics and Human Genetics, Sep. 2008, 387-402.

Mardis, "The impact of next-generation sequencing technology on genetics", Trends in Genetics 24, 2008, 133-141.

Margulies, "Genome sequencing in microfabricated high-density picolitre reactors", Nature, vol. 437, 2005, 376-380 and Supplemental Materials.

Marine, "Evaluation of a transposase protocol for rapid generation of shotgun high-throughput sequencing libraries from nanogram quantities of DNA", Appl. Environ. Microbial, vol. 77 (22), Nov. 2011, 8071-8079.

Mazurkiewicz et al., "Signature-tagged mutagenesis: barcoding mutants for genome-wide screens," Nature Reviews Genetics, Dec. 2006, 7(12):929-39.

Mazutis, "Droplet-based microfluidic systems for high- throughput single DNA molecule isothermal amplification and analysis", Anal Chem. 81 (12), 2009, 4813-21.

McCloskey, "Encoding PCR Products with Batch-stamps and Barcodes", Biochem Genet 45:761, Oct. 23, 2007, 761-767.

Meissner, Reduced representation bisulfite sequencing for comparative high-resolution DNA methylation analysis Nucleic Acids Research, 33, 2005, 5868-5877.

Miner, "Molecular barcodes detect redundancy and contamination in hairpin-bisulfite PCR", Nucleic Acids Research, 2004, vol. 32, No. 17, Sep. 30, 2004, e135, 4 paqes.

Mitra, "Fluorescent in situ sequencing on polymerase colonies", Analytical Biochemistry—320 (2003) 55-65, 2003, 55-65.

Mizuuchi, "In vitro transposition of bacteriophage Mu: a biochemical approach to a novel replication reaction", Cell, 35, 1983, 785-94.

Mizuuchi, "Transpositional Recombination: Mechanistic Insights from Studies of Mu and Other Elements", Annu. Rev. Biochem. 61, 1992, 1011-51.

Mortazavi, "Mapping and quantifying mammalian transcriptomes by RNA-seq", Nature Methods, 5(7), 2008, 621-8.

Ng, "Targeted capture and massively parallel sequencing of 12 human exomes" Nature. 461 (7261), 2009, 272-6.

Nijman, "Mutation discovery by targeted genomic enrichment of multiplexed barcoded samples", Nature Methods, vol. 7, No. 11, Nov. 2010, 913-915.

Oh, "A Robust Platform for High-Throughput Genomics in Microorganisms", A dissertation submitted to the department of genetics and the committee on graduate studies of Stanford University in partial fulfillment of the requirements for the degree of doctor of philosophy, Mar. 2010, i, ii and 10-30.

Oh, "A universal TagModule collection for parallel genetic analysis of microorQanisms", Nucleic Acids Research, vol. 38, No. 14, May 21, 2010, 146.

Ohtsubo, "Bacterial insertion sequences", Curr. Top. Microbial. Immunol. 204, 1996, 26 pages.

Old, R. et al., "Recognition sequence of restriction endonuclease Ill from Hemophilus influenzae", J Mal Biology, vol. 92(2), Feb. 25, 1975, 331-339.

Ooka, "Inference of the impact of insertion sequence (IS) elements on bacterial genome diversification through analysis of small-size structural polymorphisms in *Escherichia coli* 0157 Qenomes", Genome Research, vol. 19, 2009, 1809-1816.

Oroskar, "Detection of immobilized amplicons by ELISA-like techniques", Clinical Chemistry 42, 1996, 1547-1555.

Parkinson et al., Genome Research, vol. 22, No. 1, Jan. 2012, 125-133.

Paul, "Single-molecule dilution and multiple displacement amplification for molecular haplotypinQ", BioTechniques 38, Apr. 2005, 553-559.

PCT International Preliminary Report on Patentability mailed in PCT application No. PCT/IB2014/000610, Jul. 14, 2015.

PCT International Search Report and The Written Opinion, issued for PCT/US2011/059642, Apr. 10, 2012, 12.

PCT International Search Report and Written Opinion for PCT Appl. No. PCT/US2015/038050, mailed Aug. 28, 2015, 13 pages.

PCT International Search Report and Written Opinion for PCT/US12/23679, Applicant: University of Washington Through Its Center for Commercialization, Date of Mailing: Aug. 24, 2012.

PCT Search Report and Written Opinion for PCT application No. PCT/US2014/070658, Jun. 23, 2015.

Peck et al., "A method for high-throughput gene expression signature analysis,".

Piscelli, S. et al., "Full-Length RNA-seq from Single Cells Using Smart-seq2," Nature Protocols 2014, 9(1), 171-181.

Plasterk, "The Tcl/mariner transposon family", Curr Top Microbial Immunol, 204, 1996, 125-43.

Pobigaylo, "Construction of a large signature-tagged min0Tn5 transposon library and its application to mutagenesis of Sinorhizobium meliloti", Applied and Environmental MicrobioloQy, vol. 72, No. 6, Jun. 2006, 4329-4337.

(56)                  References Cited

OTHER PUBLICATIONS

Ramanathan, "An integrative approach for the optical sequencing of single DNA molecules", Analytical Biochemistry, vol. 330, No. 2, 2004, 227-241.

Raymond, "Targeted, haplotype-resolved resequencing of long segments of human aenome", Genomics 86, 2005, 759-766.

Reinhardt, "De Novo Assembly Using Low-Coverage Short Read Sequence Data from the Rice Pathogen Pseudomonas syringae pv. Oryzae", Genome Research 19(2), Feb. 2009, 294-305.

Rhode, CK et al., "New tools for integrated genetic and physical analyses of the *Escherichia coli* chromosome", Gene, vol. 166(1), Dec. 1, 1995, 1-9.

Riehn, "Restriction mapping in nanofluidic devices", Proceedings of the National Academy of Sciences of the United States of America 102(29):, 2005, 10012-10016.

Ritz, "Structural variation analysis with strobe reads", Bioinformatics. 26(10), 2010, 1291-8.

Ronaghi, "A Sequencing Method Based on Real-Time Pyrophosphate", Science. Jul. 17, 1998; 281 (5375):363-365 USE, Jul. 17, 1998, 363-365.

Ronaghi, "Pyrosequencing sheds light on DNA sequencing", Genome Res, 11(1), 2001, 3-11.

Ronaghi, "Real-time DNA sequencing using detection of pyrophosphate release", Anal. Biochem. Nov. 1, 1996; 242 (1):84-9, Nov. 1, 1996, 84-89.

RU Decision to Grant in Russian Appln. No. 2019138705, dated Sep. 16, 2020, 14 pages (with English translation).

RU Office Action in Russian Appln. No. 2019138705, dated May 22, 2020, 14 pages (with English translation).

RU Russian Office Action in Russian Appln. No. 2017116989, dated May 17, 2019, 21 pages (with English Translation).

RU Russian Search Report in Russian Appln. No. 2019138705, dated May 22, 2020, 4 pages (with English translation).

Savilahti, "The Phage Mu transpososome core: DNA requirements for assembly and function", EMBO J., 14, 1995, 4893-4903.

Schwartz, "Capturing native long-range contiguity by in situ library construction and optical sequencing", PNAS, vol. 109m No. 46, 2012, 18749-18754.

Schwartz, "Ordered restriction maps of Saccharomyces cerevisiae chromosomes constructed bv optical mappina", Science. 262 (5130), 1993, 110-4.

Seong et al., "Measurement of Enzyme Kinetics Using a Continuous-Flow Microfluidic System," Anal. Chem. 2003, 75, 3161-3167.

Shendure, "Accurate Multiplex Polony Sequencing of an Evolved Bacterial Genome", Science, vol. 309, Sep. 9, 2005, 1728-1732.

Shendure, "Advanced sequencing technologies: methods and goals", Nature Rev. Genet., 5, 2004, 335-344.

Shendure, "Next-generation DNA sequencing", Nature Biotechnology 26(10), 2008, 1135-1145.

Shendure, "Sequence Tag Directed Subassembly of Short Sequencing Reads Into Long Sequencing Reads", U.S. Appl. No. 61/096,720, filed Sep. 12, 2008.

Shevchenko, "Systematic sequencing of eDNA clones using the transposon Tn5", Nucl. Acids Res. vol. 30, No. 11, oo 2469-2477 (2002).

Simon, "Short-Read Sequencing Technologies for Transcriptional Analyses", Annual review of plant bioloav 60, 2009, 305-333.

Sipos, "An Improved Protocol for Sequencing of Repetitive Genomic Regions and Structural Variations Using Mutagenesis and Next Generation Sequencing", PLoS One 7(8), published online doi: 10.1371/journal.pone.0043359, Aug. 17, 2012, e43359.

Smith, "Direct Mechanical Measurements of the Elasticity of Single DNA Molecules by UsinQ MaQnetic Beads", Science, 258, 1992, p. 1122.

Soni, "Progress toward Ultrafast DNA Sequencing Using Solid-State Nanopores", Clin Chem, 53(11), 2007, 1996-2001.

Sorber, "The Long March: A Sample Preparation Technique That Enhances Contig Length and Coverage by High-Throughput Short-Read Sequencing", PLoS One 2(10):e3495, Oct. 2008, 9 pages.

Steensel, "Genomics tools for unraveling chromosome architecture", Nature Biotechnology, Oct. 13, 2010.

Steiniger et al., "Defining characteristics of Tn 5 Transposase non-specific DNA binding," Nucleic Acids Research, Jan. 1, 2006, 34(9):2820-32.

Supplementary European Search Report for Application EP12741945. 5, Applicant: University of Washington Through Its Center for Commercialization, Date of MailinQ: Sep. 22, 2014.

Syed, "Next-generation sequencing library preparation: simultaneous fragmentation and tagging using in vitro transposition", Application Notes, Nature Methods, Epicentre Biotech, Nov. 2009, i-ii.

Syed, "Optimized library preparation method for next- generation sequencing", Nature Methods, 6(10), 2009, 1-11.

Taylor, "Characterization of chemisorbed monolayers by surface potential measurements", J. Phys. D: Aool. Phys., 24, 1991, p. 1443.

Twining et al., "Functional characterization of arginine 30, lysine 40, and arginine 62 in Tn5 transposase," Journal of Biological Chemistry, Jun. 22, 2001, 276(25):23135-43.

US Final Office Action in U.S. Appl. No. 15/519,482, dated May 17, 2021, 46 pages.

US Final Office Action in U.S. Appl. No. 15/519,482, dated Oct. 23, 2019, 21 pages.

US Final Office Action in U.S. Appl. No. 16/173,202, dated Oct. 13, 2020.

US Final Office Action in U.S. Appl. No. 16/173,202, dated Sep. 20, 2019, 43 pages.

US Non-Final Office Action in U.S. Appl. No. 15/519,482, dated Mar. 18, 2019, 52 pages.

US Non-Final Office Action in U.S. Appl. No. 16/173,202, dated Apr. 24, 2020, 34 pages.

US Non-Final Office Action in U.S. Appl. No. 16/173,202, dated Apr. 29, 2019, 21 pages.

US Non-Final Office Action in U.S. Appl. No. 15/519,482, dated Aug. 11, 2020, 36 pages.

US Office Action in U.S. Appl. No. 15/519,482, dated Aug. 11, 2020, 36 pages.

US Office Action in U.S. Appl. No. 15/519,482, dated Dec. 15, 2021, 46 pages.

US Office Action in U.S. Appl. No. 16/173,202, dated Mar. 15, 2021, 47 pages.

US Office Action in U.S. Appl. No. 16/665,800, dated Jan. 25, 2021, 26 pages.

US Office Action in U.S. Appl. No. 16/735,348, dated Feb. 4, 2021, 40 pages.

Van Berkum, "Method to Study the Three-dimensional Architecture of Genomes", htto://www.iove.com/details.sto?id=1869 doi:1 0.3791/ 1869. J Vis Exo.39 (2010).

Vincent, "Helicase-dependent isothermal DNA amplification", EMBO Rep 5, Epub Jul. 9, 2004, 795-800.

Voordouw, et al., "Studies on ColE1-plasmid DNA and its interactions with histones: sedimentation velocity studies of monodisperse complexes reconstituted with calf-thymus histones," Nucleic Acids Res. 1977, 4(5), 1207-1223.

Walker, "A Chemiluminescent DNA Probe Test Based on Strand Displacement Amplification", Molecular Methods for Virus Detection, 1995, Academic Press Inc. Ch 15 pp. 329-349., 1995, 329-349.

Walker, "Strand displacement amplification—an isothermal, in vitro DNA amplification technique", NAR, 20, 1992, 1691-1696.

Wang, "Calling Cards enable multiplexed identification of genomic targets of DNA-bindinq proteins", Genome Research, vol. 21, No. 5, 2011, 748-755.

Waterston, "Initial sequencing and comparative analysis of the mouse genome", Nature. 420(6915), 2002, 520-62.

Waterston, "On the sequencing of the human genome", Pro Proc Natl Acad Sci USA. 99(6), 2002, 3712-6.

Wilson, "New transposon delivery plasmids for insertional mutagenesis in Bacillus anthracis", Journal of Microbiological Methods, 71, 2007, 332-335.

Wold, "Sequence Census Methods for Functional Genomics", Nature Methods, 5(1), Jan. 2008, 19-21.

Wong, "ChIP'ing the mammalian genome: technical advances and insights into functional elements", Genome Medicine 1.9, 2009, 89.

(56)                    References Cited

OTHER PUBLICATIONS

Xu, "Extracting Haplotypes from Diploid Organisms", Current Issues in Molecular Biology, vol. 8, Jul. 2006, 113-122.

Zeevi, "Increasing cloning possibilities using artificial zinc finger nucleases", Proceedings of the National Academy of Sciences, USA, vol. 105, No. 35, Sep. 2008, 12785-12790.

Zeng, "High-performance single cell genetic analysis using microfluidic emulsion aenerator arrays," Anal Chem. 82 (8), 2010, 3183-90.

Zerbino, "Velvet: Algorithms for De Novo Short Read Assembly Using de Bruijn Graphs", Genome Research, 18(5), Mar. 2008, 821-829.

Zhang, "A Novel Mechanism of Transposon-Mediated Gene Activation", PLoS Genetics e1000689. Epub Oct. 16, 2009.

Zhou, "A Single Molecule Scaffold for the Maize Genome", PLoS Genet5(11), 2009, e1000711.

Zhou, "Molecular genetic analysis of transposase-end DNA sequence recognition: Cooperativity of three adjacent base-pairs in specific interaction with a mutant Th5 transposase", Journal of Molecular Biology, vol. 276, 1998, 913-925.

Zhou, "Validation of rice genome sequence by optical mapping", BMC Genomics 8(1), 2007, 278.

Zilberman, "Genome-wide analysis of DNA methylation patterns.", Development 134(22), 2007, 3959-3965.

Wu, Jun, et al.; "Tn5 transposase-assisted transformation of indica rice," The Planet Journal, vol. 68, No. 1, Jul. 18, 2011, pp. 186-200.

Goryshin, Igor Y., et al.,; "Insertional transposon mutagenesis by electroporation of released Tn5 transposition complexes," Nature Biotechnology, 18.1, Jan. 2000, pp. 97-100. 2000.

\* cited by examiner

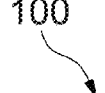
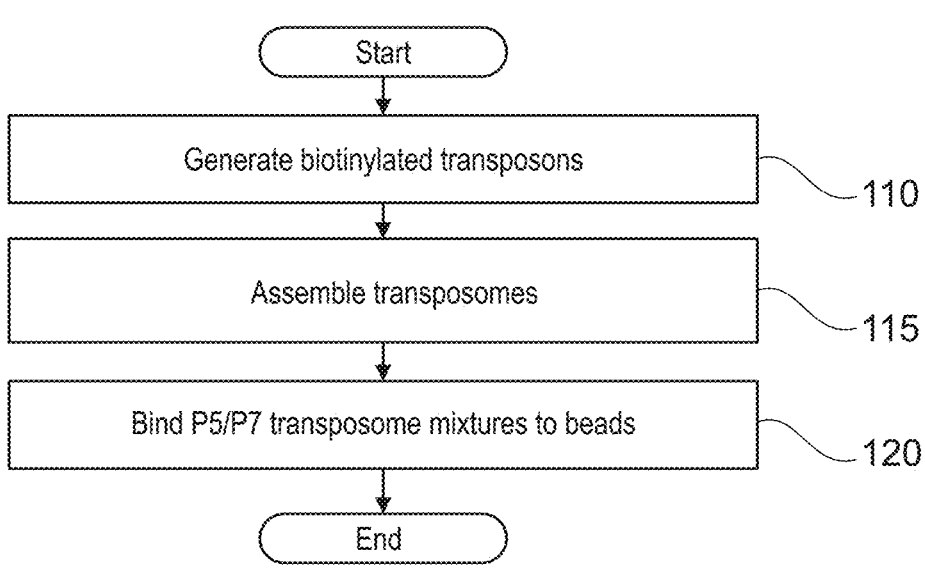
Fig. 1

400

| Sample | No of clusters with equal volume of PCR product | | | | | | | |
|---|---|---|---|---|---|---|---|---|
| pM used to cluster | 15 | | 19 | | 21 | | 24 | |
| | K/mm2 | % | K/mm2 | % | K/mm2 | % | K/mm2 | % |
| 50 ng | 466 | 100 | 541 | 100 | 618 | 100 | 668 | 100 |
| 250 ng | 504 | 108 | 598 | 110 | 703 | 114 | 740 | 111 |
| 1000 ng | 512 | 109 | 602 | 111 | 670 | 108 | 716 | 107 |
| *50 ng full repeat | 377 | 81 | 455 | 84 | 516 | 83 | 555 | 83 |

500

| | Median Insert Size | Mean Insert Size |
|---|---|---|
| BBN50-index1 | 341 | 409.78 |
| BBN500-index1 | 344 | 415.89 |
| BBN50-index2 | 337 | 405.97 |
| BBN500-index2 | 346 | 419.91 |
| BBN50-index3 | 330 | 400.35 |
| BBN500-index3 | 327 | 398.65 |
| BBN50-index4 | 321 | 388.71 |
| BBN500-index4 | 328 | 400.75 |
| BBN50-index5 | 327 | 397.62 |
| BBN500-index5 | 328 | 399.88 |
| BBN50-index6 | 324 | 389.35 |
| BBN500-index6 | 331 | 401.50 |

After hybridization capture, contiguity is maintained after Tn5 removal. DNA is hybridized to bead with indexed primers keeping all individual libraries together on a bead 1. 100bp Ladder
2. gDNA
3. 12.SuM TnS
4. 1uL NCP DNA
5. 1uL S-200 NCP DNA
6. 3uL S-200 NCP DNA
7. 6uL 2-200 NCP DNA
8. 1uL NCP DNA
9. 1uL S-400 NCP DNA
10. 3uL S-400 NCP DNA
11. 6uL S-400 NCP DNA
12. 1kb Ladder Optimization of Capture Density on Beads

|  | Probe Density (dilution) | Ligation |
|---|---|---|
| 1 | 1x | No |
| 2 | 10x | Yes |
| 3 | 1x | No |
| 4 | 10x | Yes |

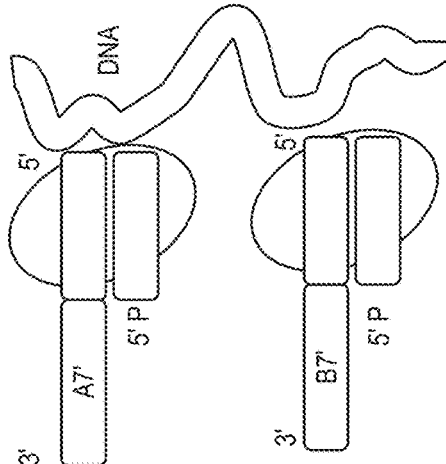
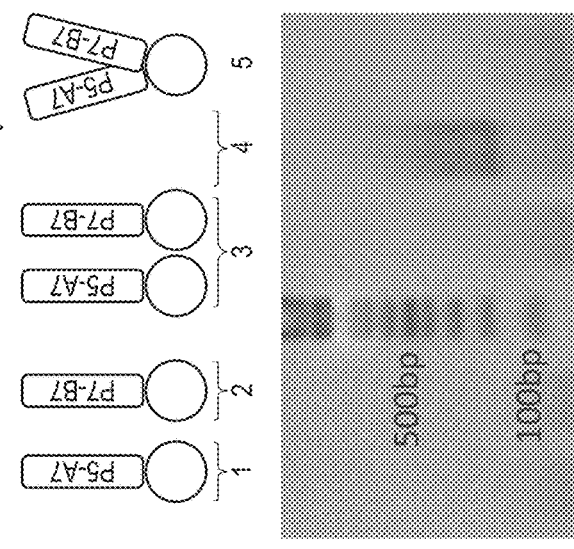
Feasibility of CPT-seq on Beads: Intra-molecular Libraries
| | Beads | Ligase Added |
|---|---|---|
| 1 | A7 | Yes |
| 2 | B7 | Yes |
| 3 | Bead A7 & B7 | Yes |
| 4 | A7+B7 | Yes |
| 5 | A7+B7 | No |
Fig. 26

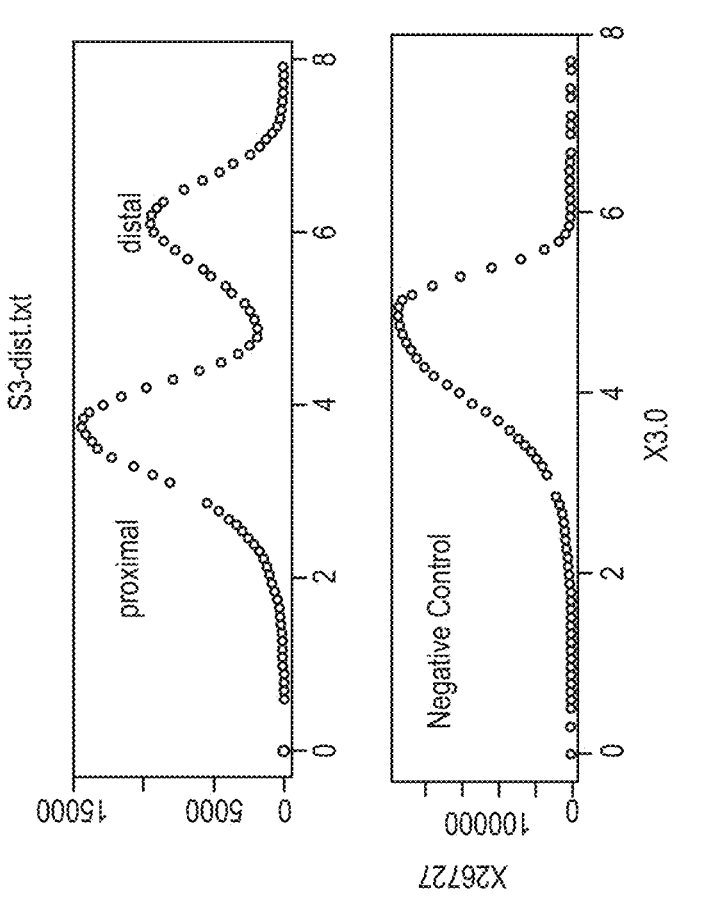
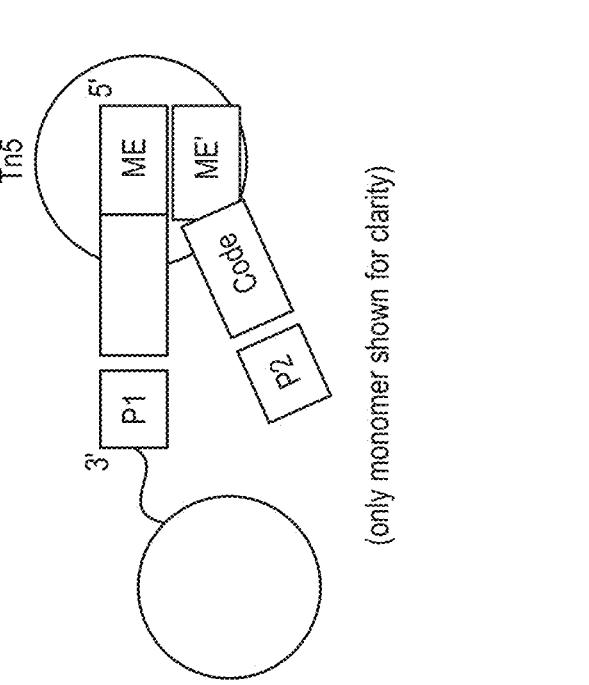
Fig. 30

- Assembly Tnp:Tn5 complex first
- Load on beads
- Wash beads
- Mix beads
- Add DNA and tagmentation
- PCR
5' biotin ME and 3' biotin ME' oligos on beads
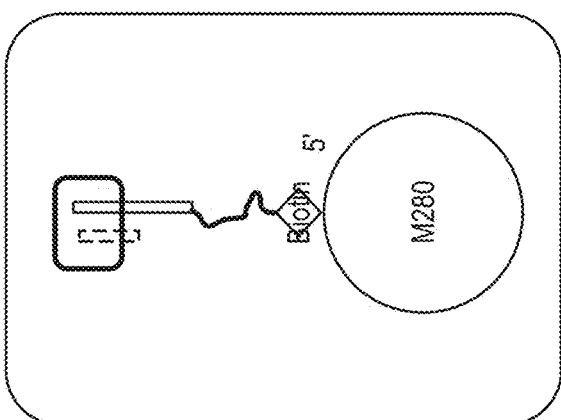
Or
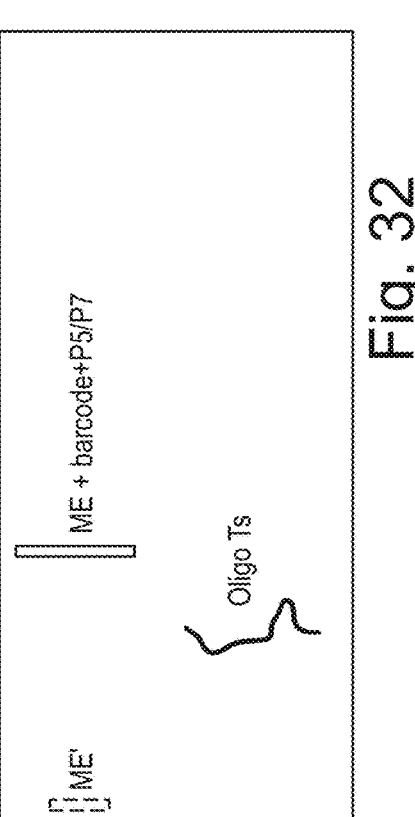
Fig. 32

Whole
Blood

A= Blood Loading Zone
B= Membrane
C= Plasma Collection Zone

Plasma collects
In Area C, free of
gDNA/haem/cells

Blood loaded
Into the Device

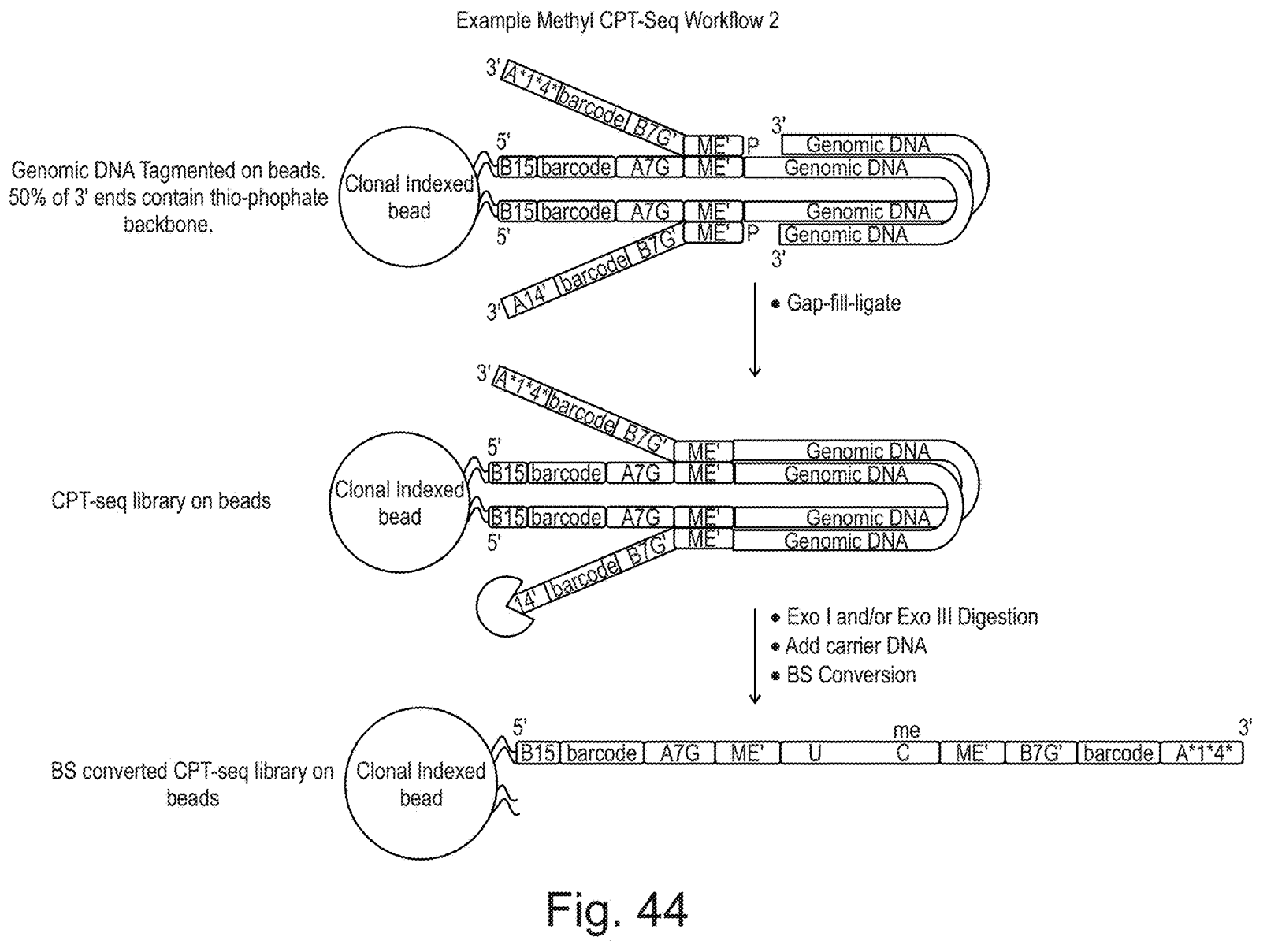

Example Methyl CPT-Seq Workflow 2

Genomic DNA Tagmented on beads.
50% of 3' ends contain thio-phophate backbone.

- Gap-fill-ligate

CPT-seq library on beads

- Exo I and/or Exo III Digestion
- Add carrier DNA
- BS Conversion

BS converted CPT-seq library on beads

Fig. 44

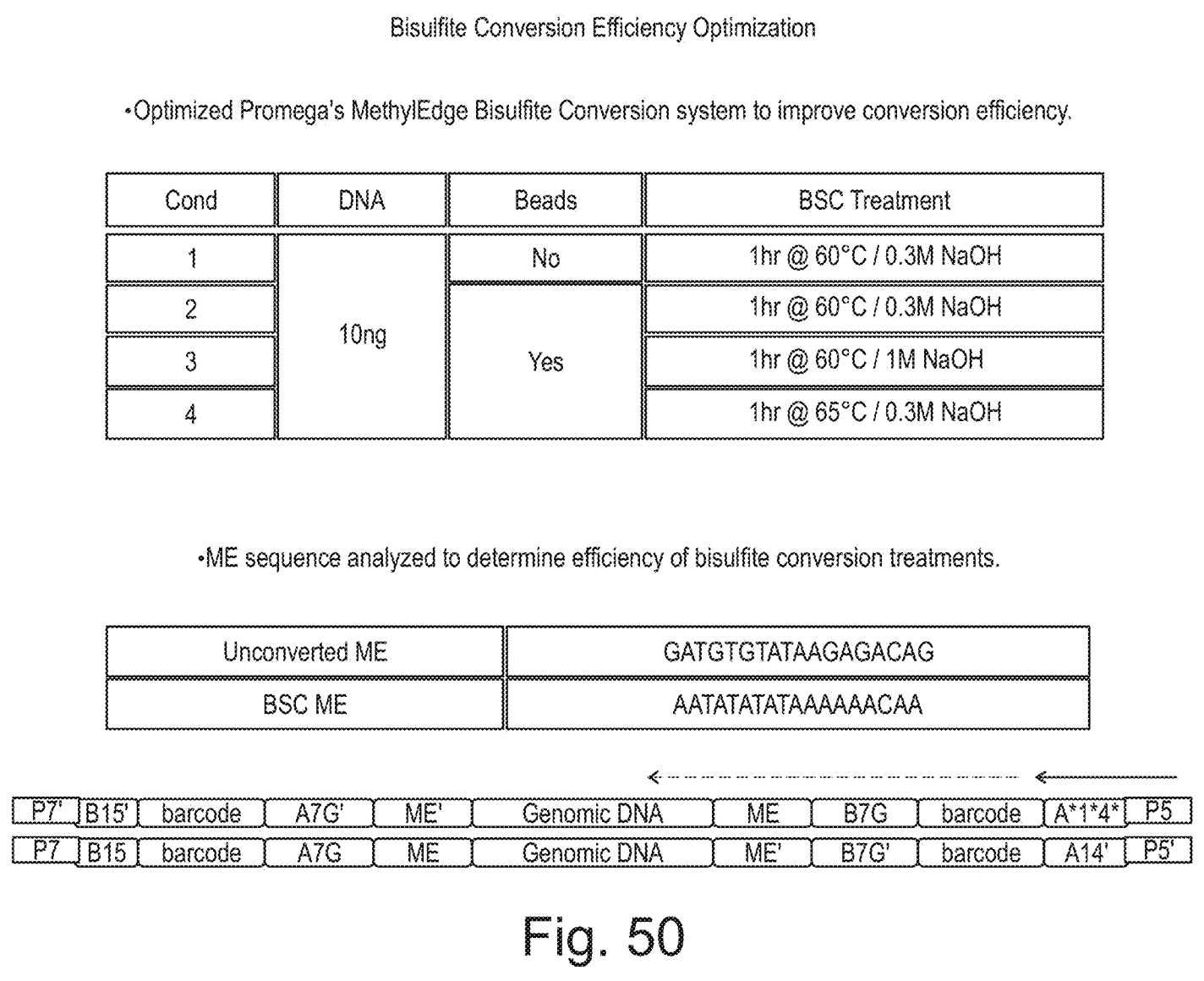

Bisulfite Conversion Efficiency Optimization

• Optimized Promega's MethylEdge Bisulfite Conversion system to improve conversion efficiency.

| Cond | DNA | Beads | BSC Treatment |
|---|---|---|---|
| 1 | 10ng | No | 1hr @ 60°C / 0.3M NaOH |
| 2 | | Yes | 1hr @ 60°C / 0.3M NaOH |
| 3 | | | 1hr @ 60°C / 1M NaOH |
| 4 | | | 1hr @ 65°C / 0.3M NaOH |

• ME sequence analyzed to determine efficiency of bisulfite conversion treatments.

| Unconverted ME | GATGTGTATAAGAGACAG |
|---|---|
| BSC ME | AATATATATAAAAAACAA |

P7' B15' barcode A7G ME' Genomic DNA ME B7G barcode A*14* P5

P7 B15 barcode A7G ME' Genomic DNA ME' B7G' barcode A14' P5'

Fig. 50

Bisulfite Conversion Efficiency Optimization

Results

- 95% bisulfite conversion (BSC) of indexed-linked libraries attached to beads.

- Similar PCR yields observed between bisulfite conditions > Harsher bisulfite treatment did not appear to degrade libraries.

Fig. 52

Enrichment of CPT-Seq libraries

| Cond | Library | Probe Set | [Probe] pM/ea | Hyb Volume | Hyb Ramp | EHB | Elution | Washes | SMB |
|---|---|---|---|---|---|---|---|---|---|
| 1 | 1.1ug CPTSeq | DNA Dunn A, B, K | 100pM | 25uL | 95 > 58 (O/N) | Form, Nxt Blkrs | ET1 | Std | 3x |
| 2 | 1.1ug CPTSeq | EEX | 2.5uL | 25uL | 95 > 58 (O/N) | Form, Nxt Blkrs | ET1 | Std | 3x |
| 3 | 1.1ug CPTSeq | RNA Dunn A, B, K | 100pM | 25uL | 95 > 65 (O/N) | Form, Nxt Blkrs | RNase H | Std | 3x |

CPT-Seq Libraries Post Enrichment

•Targeted indexed-linked sequencing libraries

Mechanisms for Swapping

1-DNA binds to two differently indexed beads

-Possible solutions:

• More space between beads( dilute DNA more before adding)

• Add dummy beads to space complex-beads out more

2 - Complexes come apart and re-form

- Possible solutions:

• Be more gentle with mixing steps

• Wash away monomers not bound by SA

• Crosslink?

• Form complexes fresh?

3 - SA-biotin bond breaks and complex re-hybs to another bead

- Possible solutions:

• Traptavidin beads

• Block free streptavidin sites so that biotinylated oligos can't bind

4 - Contamination

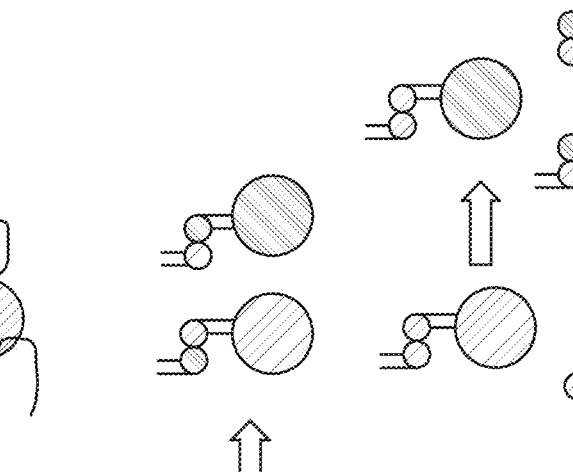
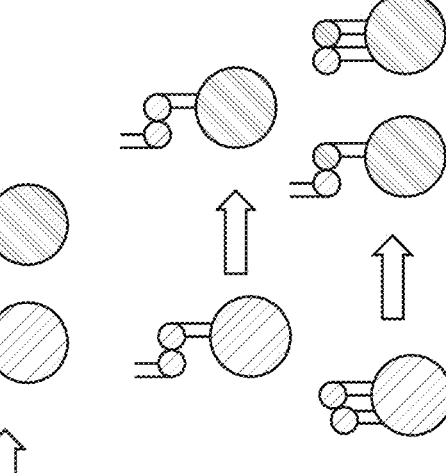

Fig. 57

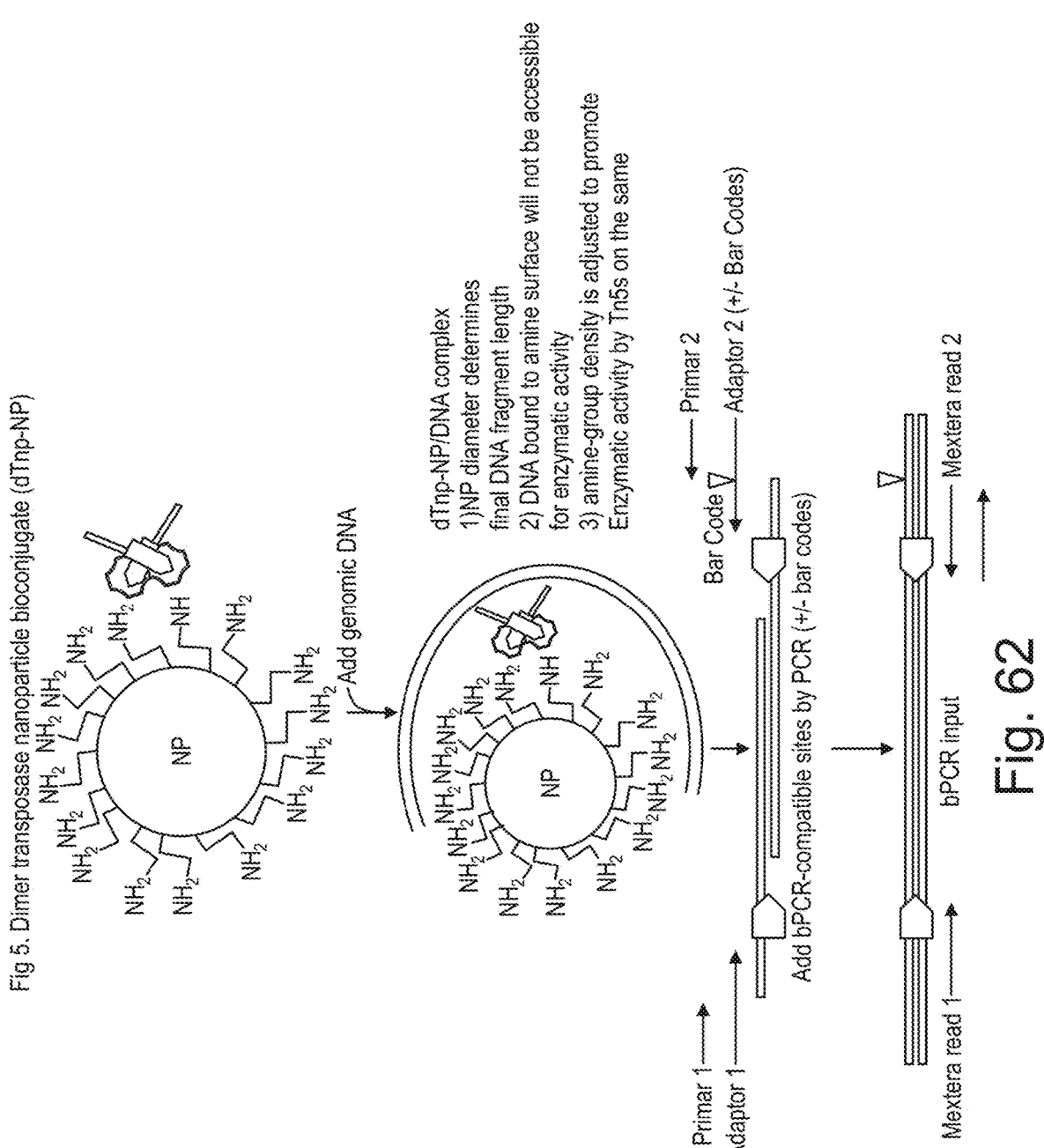

Fig 5. Dimer transposase nanoparticle bioconjugate (dTnp-NP)

Add genomic DNA dTnp-NP/DNA complex
1) NP diameter determines final DNA fragment length
2) DNA bound to amine surface will not be accessible for enzymatic activity
3) amine-group density is adjusted to promote Enzymatic activity by Tn5s on the same Primar 2
Adaptor 2 (+/- Bar Codes)

Bar Code

Primar 1
Adaptor 1

Add bPCR-compatible sites by PCR (+/- bar codes)

Mextera read 1 bPCR input

Mextera read 2

Fig. 62

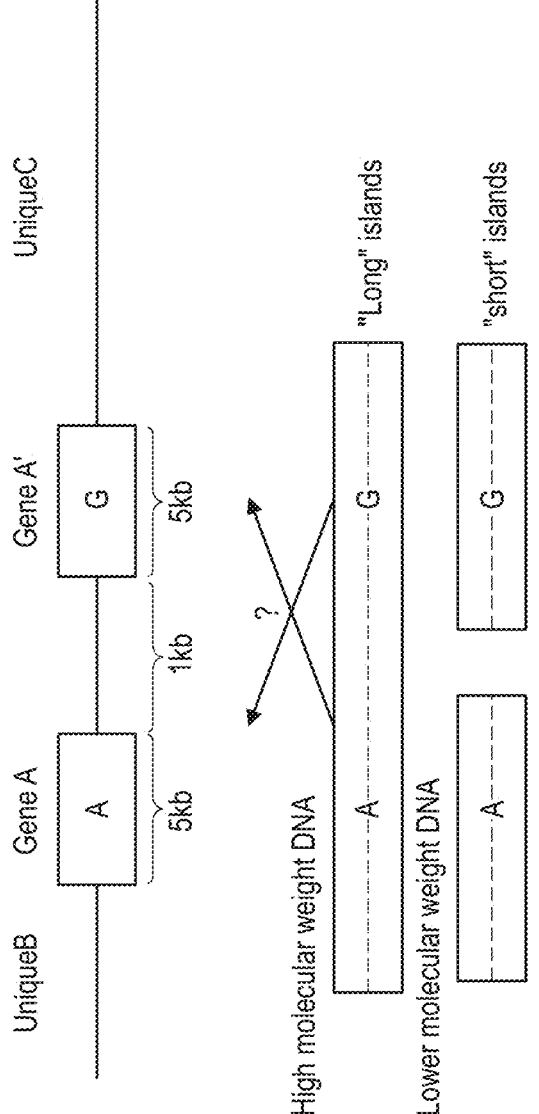

Indexed linked reads for assembly/phasing of pseudo-genes

Fig. 64

- Example, CYP2D6
- Long islands (>30kb) of indexed linked reads will span the speudogenes, gene A and A'
  Due to the high sequence, it is not possible to determine which variant belongs to
  GeneA or GeneA'
- Shorter islands will only link onevariant in one of the pseudogenes with unique surrounding sequence
- → This can be accomplished by shearing DNA before CPT-seq or
  use combination of sheared and unsheared DNA

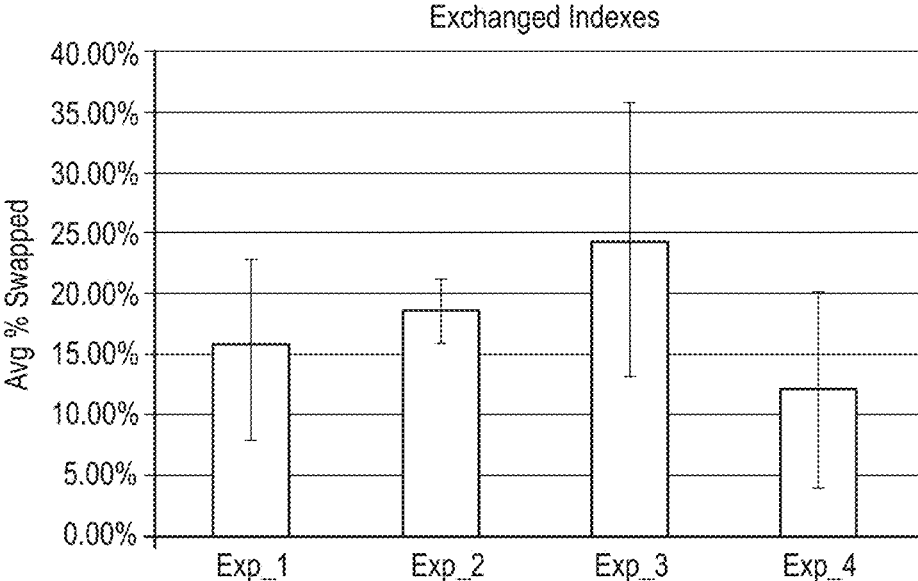
Figure 1: Index exchange. Bead with different indices were prepared. After mixing, Index exchange was determined by sequencing the libraries and reporting the indices for each library. % "swapped" was calculated as (D4+D5+E3+E5+f4)/(sum of all 96) and reported in the figure.
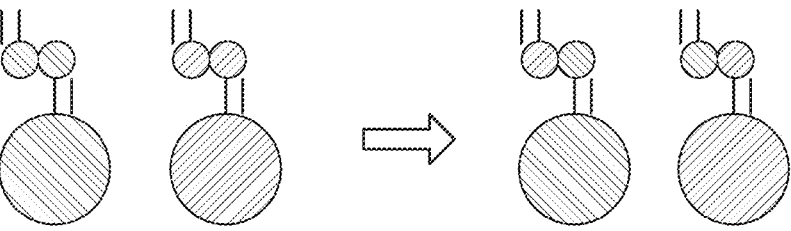
Fig. 65

MiSeq Methyl CPT-Seq Statistics

• Observed phased reads "islands"
  ○ Average island size 17 kb
  ○ >50% unique reads
  ○ 88% of Cs are converted to Us Bisulfite Conversion Efficiency Optimization Optimized Promega's MethylEdge Bisulfite Conversion system to improve conversion efficiency.

| Cond | DNA | Beads | BSC Treatment |
|------|-----|-------|---------------|
| 1 |  | No | 1hr @ 60°C/0.3M NaOH |
| 2 | 10 ng |  | 1hr @ 60°C/0.3M NaOH |
| 3 |  | Yes | 1hr @ 60°C/1M NaOH |
| 4 |  |  | 1hr @ 65°C/0.3M NaOH |

ME sequence analyzed to determine efficiency of bisulfite conversion treatments.

| Unconverted ME | GATGTGTATAAGAGACAG |
|----------------|--------------------|
| BSC ME | AATATATATAAAAAACAA |

| P7 | B15' | barcode' | A7G' | ME' | Genomic DNA | ME | B7G | barcode | A*1*4* | P5 |
|----|------|----------|------|-----|-------------|-----|-----|---------|--------|----|
| P7 | B15 | barcode | A7G | ME | Genomic DNA | ME' | B7G' | barcode' | A14' | P5' |

Fig. 75A

Results
- 95% bisulfiteconversion with 1M NaOH or 65°C heat treatment
- Similar PCR yields observed betweem bisulfite conditions > Harsher bisulfite treatment did not appear to degrade libraries.

| Beads: | no | yes | yes | yes |
|--------|-----|------|------|------|
| [NaOH]: | 0.3M | 0.3M | 1M | 0.3M |
| $T_{asc}$: | 60C | 60C | 60C | 65C |

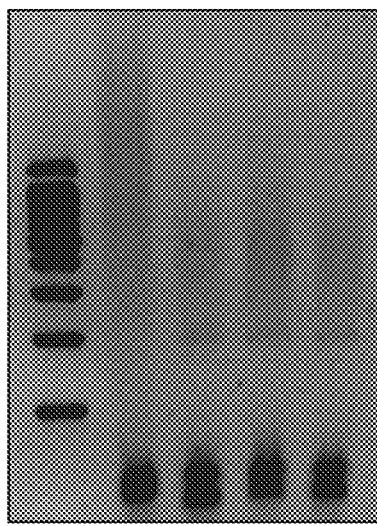

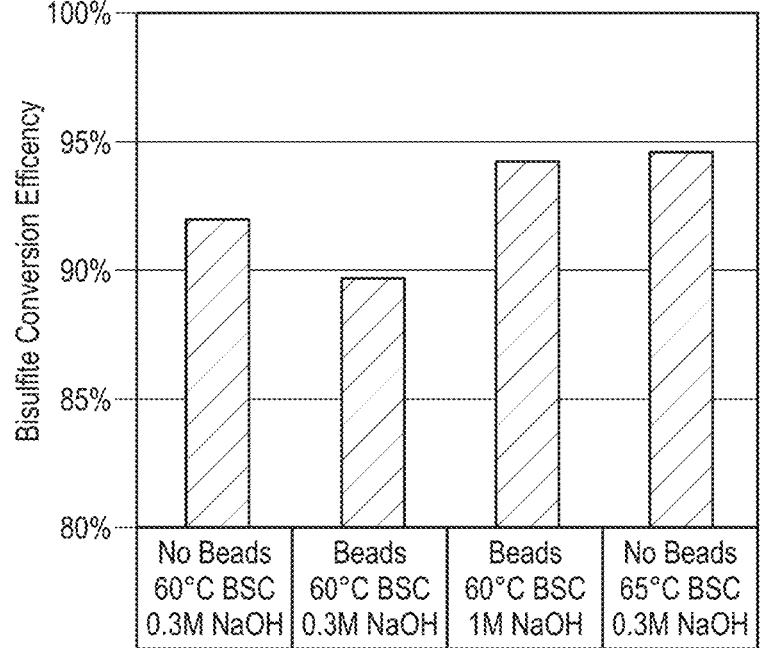

Fig. 75B

SEQUENCE LISTING

```
<160> NUMBER OF SEQ ID NOS: 9

<210> SEQ ID NO 1
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
aatgatacgg cgaccaccga gatctacac                                          29

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
caagcagaag acggcatacg agat                                               24

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
agatgtgtat aagagacag                                                     19

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
ctgtctctta tacacatct                                                     19
```

```
<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
gatgtgtata agagacag                                                    18

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
aatatatata aaaaacaa                                                    18

<210> SEQ ID NO 7
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
tttttttttt tt                                                          12

<210> SEQ ID NO 8
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
aaaaaaaaaa aaa                                                         13

<210> SEQ ID NO 9
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
aaaaaaaaaa aa                                                          12
```

CONTIGUITY PRESERVING TRANSPOSITION

RELATED APPLICATIONS

This application is a continuation of Ser. No. 16/173,202 (now abandoned), filed on Oct. 29, 2018, which is a continuation of Ser. No. 15/519,482 (now U.S. Pat. No. 11,873, 480), filed on Apr. 14, 2017, which is a national stage entry of International Patent Application No. PCT/US2015/ 056040, filed Oct. 16, 2015, which claims priority to U.S. Provisional Patent Application No. 62/065,544 filed on Oct. 17, 2014, U.S. Provisional Patent Application No. 62/157, 396 filed on May 5, 2015, and U.S. Provisional Patent Application No. 62/242,880 filed on Oct. 16, 2015, which are hereby incorporated by reference in their entirety.

SEQUENCE LISTING

The instant application contains a Sequence Listing which has been submitted electronically in ASCII format and is hereby incorporated by reference in its entirety. Said ASCII copy, created on Mar. 31, 2022, is named SequenceListing.txt and is 2.48 kilobytes in size.

FIELD OF THE INVENTION

Embodiments of the present invention relate to sequencing nucleic acids. In particular, embodiments of the methods and compositions provided herein relate to preparing nucleic acid templates and obtaining sequence data therefrom.

BACKGROUND OF THE INVENTION

The detection of specific nucleic acid sequences present in a biological sample has been used, for example, as a method for identifying and classifying microorganisms, diagnosing infectious diseases, detecting and characterizing genetic abnormalities, identifying genetic changes associated with cancer, studying genetic susceptibility to disease, and measuring response to various types of treatment. A common technique for detecting specific nucleic acid sequences in a biological sample is nucleic acid sequencing.

Nucleic acid sequencing methodology has evolved significantly from the chemical degradation methods used by Maxam and Gilbert and the strand elongation methods used by Sanger. Today several sequencing methodologies are in use which allow for the parallel processing of nucleic acids all in a single sequencing run. As such, the information generated from a single sequencing run can be enormous.

SUMMARY OF THE INVENTION

In one aspect, described herein are methods of preparing a library of barcoded DNA fragments of a target nucleic acid. The methods include contacting a target nucleic acid with a plurality of transposome complexes, each transposome complex includes: transposons and transposases, in which the transposons comprise transferred strands and non-transferred strands. At least one of the transposons of the transposome complex comprises an adaptor sequence capable of hybridizing to a complementary capture sequence. The target nucleic acid is fragmented into a plurality of fragments and inserting plurality of transferred strands to the 5' end of at least one strand of the fragments while maintaining the contiguity of the target nucleic acid. The plurality of fragments of the target nucleic acid are contacted with a plurality of solid supports, each of the solid supports in the plurality comprising a plurality of immobilized oligonucleotides, each of the oligonucleotides comprising a complementary capture sequence and a first barcode sequence, and wherein the first barcode sequence from each solid support in the plurality of the solid supports differs from the first barcode sequence from other solid supports in the plurality of solid supports. The barcode sequence information is transferred to the target nucleic acid fragments, thereby producing an immobilized library of double-stranded fragments wherein at least one strand is 5'-tagged with the first barcode such that at least two fragments of the same target nucleic acid receives identical barcode information.

In one aspect, described herein are methods for determining contiguity information of a target nucleic acid sequence The methods include contacting the target nucleic acid with a plurality of transposome complexes, each transposome complex comprising: transposons and transposases, in which the transposons comprise transferred strands and non-transferred strands, in which at least one of the transposons of the transposome complex comprise an adaptor sequence capable of hybridizing to a complementary capture sequence. The target nucleic acid is fragmented into a plurality of fragments and plurality of transferred strands is inserted into the plurality of fragments while maintaining the contiguity of the target nucleic acid. The plurality of fragments of the target nucleic acid is contacted with a plurality of solid supports. Each of the solid supports in the plurality comprising a plurality of immobilized oligonucleotides, each of the oligonucleotides comprising a complementary capture sequence and a first barcode sequence, and wherein the first barcode sequence from each solid support in the plurality of the solid supports differs from the first barcode sequence from other solid supports in the plurality of solid supports. The barcode sequence information is transferred to the target nucleic acid fragments such that at least two fragments of the same target nucleic acid receive identical barcode information. The sequence of the target nucleic acid fragments and the barcode sequences are determined. The contiguity information of the target nucleic acid are determined by identifying the barcode sequences. In some embodiments, the transposases of transposome complexes are removed after transposition and subsequent hybridization of the adaptor sequences of the transposon to the complimentary capture sequence. In some embodiments, the transposases are removed by SDS treatment. In some embodiments, the transposases are removed by proteinase treatment.

In one aspect, described herein are methods for simultaneously determining phasing information and methylation status of a target nucleic acid sequence. The methods include contacting the target nucleic acid with a plurality of transposome complexes, each transposome complex includes transposons and transposases, in which the transposons comprise transferred strands and non-transferred strands, wherein at least one of the transposons of the transposome complex comprise an adaptor sequence capable of hybridizing to a complementary capture sequence. The target nucleic acid is fragmented into a plurality of fragments and plurality of transferred strands is inserted into the target nucleic acid fragments while maintaining the contiguity of the target nucleic acid. The plurality of fragments of the target nucleic acid are contacted with a plurality of solid supports, each of the solid supports in the plurality comprising a plurality of immobilized oligonucleotides, each of the oligonucleotides comprising a complementary capture sequence and a first barcode sequence, and wherein the first barcode sequence from each solid support in the plurality of the solid supports differs from the first barcode sequence from other solid supports in the plurality of solid supports. The barcode sequence information is transferred to the target nucleic acid fragments such that at least two fragments of the same target nucleic acid receive identical barcode information. The target nucleic acid fragments comprising barcodes are subjected to bisulfite treatment, thereby generating bisulfite treated target nucleic acid fragments comprising barcodes. The sequence of the bisulfite treated target nucleic acid fragments and the barcode sequences are determined. The contiguity information of the target nucleic acid is determined by identifying the barcode sequences.

In one aspect, described herein are methods of preparing an immobilized library of tagged DNA fragments. The methods include providing a plurality of solid supports having transposome complexes immobilized thereon, in which the transposome complexes are multimeric and the transposome monomeric units of the same transposome complex are linked to each other, and wherein said transposome monomeric units comprise a transposase bound to a first polynucleotide, said first polynucleotide comprising (i) a 3' portion comprising a transposon end sequence, and (ii) a first adaptor comprising a first barcode. A target DNA is applied to the plurality of solid supports under conditions whereby the target DNA is fragmented by the transposome complexes, and the 3' transposon end sequence of the first polynucleotide is transferred to a 5' end of at least one strand of the fragments; thereby producing an immobilized library of double-stranded fragments wherein at least one strand is 5'-tagged with the first barcode.

In one aspect, described herein are methods of preparing a sequencing library for determining the methylation status of a target nucleic acid. The methods include fragmenting the target nucleic acid into two or more fragments. A first common adaptor sequence is incorporated into the 5'-end of the fragments of the target nucleic acid, wherein the adaptor sequence comprises a first primer binding sequence and an affinity moiety, wherein the affinity moiety in one member of the binding pair. The target nucleic acid fragments are denatured. The target nucleic acid fragments are immobilized on a solid support, in which the solid support comprises other member of the binding pair and the immobilization of the target nucleic acid is by binding of the binding pair. The immobilized target nucleic acid fragments are subjected to bisulfite treatment. A second common adaptor sequence is incorporated to the bisulfite treated immobilized target nucleic acid fragments, wherein the second common adaptor comprises a second primer binding site. The bisulfite treated target nucleic acid fragments immobilized on solid support is amplified thereby producing a sequencing library for determining the methylation status of a target nucleic acid.

In one aspect, described herein are methods of preparing a sequencing library for determining the methylation status of a target nucleic acid. The methods include providing a plurality of solid support comprising immobilized transposome complexes immobilized thereon. The transposome complexes comprise transposons and transposases, in which the transposons comprise transferred strands and non-transferred strands. The transferred strand comprises (i) a first portion at the 3'-end comprising the transposase recognition sequence, and (ii) a second portion located 5' to the first portion comprising a first adaptor sequence and first member of a binding pair. The first member of the binding pair binds to a second member of the binding pair on the solid support, thereby immobilizes the transposon to the solid support. The first adaptor also comprises a first primer binding sequence. The non-transferred strand comprises (i) a first portion at the 5'-end comprising the transposase recognition sequence and (ii) a second portion located 3' to the first portion comprising a second adaptor sequence, in which the terminal nucleotide at the 3'-end is blocked. The second adaptor also comprises a second primer binding sequence The target nucleic acid is contacted with the plurality of solid support comprising immobilized transposome complexes. The target nucleic acid is fragmented into a plurality of fragments and plurality of transferred strands are inserted to the 5' end of at least one strand of the fragments, thereby immobilizing the target nucleic acid fragments to the solid support. The 3'-end of the fragmented target nucleic acid is extended with a DNA polymerase. The non-transferred strand is ligated to the 3'-end of the fragmented target nucleic acid. The immobilized target nucleic acid fragments are subjected to bisulfite treatment. The 3'-end of the immobilized target nucleic acid fragments damaged during the bisulfite treatment is extended by using a DNA polymerase such that the 3'-end of the immobilized target nucleic acid fragments comprise a homopolymeric tail. A second adaptor sequence is introduced to the 3'-end of the immobilized target nucleic acid fragments damaged during the bisulfite treatment. The bisulfite treated target nucleic acid fragments immobilized on solid support are amplified using a first and a second primer, thereby producing a sequencing library for determining the methylation status of a target nucleic acid.

In one aspect, disclosed herein are methods of preparing a sequencing library for determining the methylation status of a target nucleic acid. The methods include a. contacting the target nucleic acid with transposome complexes, in which the transposome complexes comprise transposons and transposases. The transposons comprise transferred strands and non-transferred strands. The transferred strand includes (i) a first portion at the 3'-end comprising the transposase recognition sequence, and (ii) a second portion located 5' to the first portion comprising a first adaptor sequence and first member of a binding pair, wherein the first member of the binding pair binds to a second member of the binding pair. The non-transferred strand includes (i) a first portion at the 5'-end comprising the transposase recognition sequence and (ii) a second portion located 3' to the first portion comprising a second adaptor sequence, in which the terminal nucleotide at the 3'-end is blocked, and wherein the second adaptor comprises a second primer binding sequence. The target nucleic acid is fragmented into a plurality of fragments and inserting plurality of transferred strands to the 5' end of at least one strand of the fragments, thereby immobilizing the target nucleic acid fragments to the solid support. The target nucleic acid fragments comprising the transposon end are contacted with the plurality of solid support comprising second member of the binding pair, wherein binding of the first member of the binding pair to the second member of the binding pair immobilizes the target nucleic acid to the solid support. The 3'-end of the fragmented target nucleic acid is extended with a DNA polymerase. The non-transferred strand is ligated to the 3'-end of the fragmented target nucleic acid. The immobilized target nucleic acid fragments are subjected to bisulfite treatment. The 3'-end of the immobilized target nucleic acid fragments damaged during the bisulfite treatment is extended by using a DNA polymerase such that the 3'-end of the immobilized target nucleic acid fragments comprise a homopolymeric tail. A second adaptor sequence is introduced to the 3'-end of the immobilized target nucleic acid fragments damaged during the bisulfite treatment. The bisulfite treated target nucleic acid fragments immobilized on solid support are amplified using a first and a second primer, thereby producing a sequencing library for determining the methylation status of a target nucleic acid.

In some embodiments, the terminal nucleotide at the 3'-end of the second adaptor is blocked by a member selected from the group consisting of a dideoxy nucleotide, a phosphate group, thiophosphate group, and an azido group.

In some embodiments, affinity moieties can be members of a binding pair. In some cases, the modified nucleic acids may comprise a first member of a binding pair and the capture probe may comprise a second member of the binding pair. In some cases, capture probes may be immobilized to a solid surface and the modified nucleic acid may comprise a first member of a binding pair and the capture probe may comprise a second member of the binding pair. In such cases, binding the first and second members of the binding pair immobilizes the modified nucleic acid to the solid surface. Examples of binding pair include, but are not limited to biotin-avidin, biotin-streptavidin, biotin-neutravidin, ligand-receptor, hormone-receptor, lectin-glycoprotein, oligonucleotide-complementary oligonucleotide, and antigen-antibody.

In some embodiments, the first common adaptor sequence is incorporated to the 5'-end fragments of the target nucleic acid by one-sided transposition. In some embodiments, the first common adaptor sequence is incorporated to the 5'-end fragments of the target nucleic acid by ligation. In some embodiments, incorporating the second common adaptor sequence into the bisulfite treated immobilized target nucleic acid fragments includes (i) extending the 3'-end of the immobilized target nucleic acid fragments using terminal transferase to comprise a homopolymeric tail; (ii) hybridizing an oligonucleotide comprising a single stranded homopolymeric portion and a double stranded portion comprising the second common adaptor sequence, wherein the ingle stranded homopolymeric portion is complementary to the homopolymeric tail; and (iii) ligating the second common adaptor sequence to the immobilized target nucleic acid fragments, thereby incorporating the second common adaptor sequence into the bisulfite treated immobilized target nucleic acid fragments.

In some embodiments, the target nucleic acid is from a single cell. In some embodiments, the target nucleic acid is from a single organelle. In some embodiments, the target nucleic acid is genomic DNA. In some embodiments, the target nucleic acid is cross-linked to other nucleic acids. In some embodiments, target nucleic acid is from formalin fixed paraffin embedded (FFPE) sample. In some embodiments, the target nucleic acid is cross-linked with proteins. In some embodiments, the target nucleic acid is cross-linked with DNA. In some embodiments, the target nucleic acid is histone protected DNA. In some embodiments, histones are removed from the target nucleic acid. In some embodiments, the target nucleic acid is cell free tumor DNA. In some embodiments, the cell free tumor DNA is obtained from placental fluid. In some embodiments, the cell free tumor DNA is obtained from plasma. In some embodiments, the plasma is collected from whole blood using a membrane separator comprising a collection zone for the plasma. In some embodiments, the collection zone for the plasma comprises transposome complexes immobilized on solid support. In some embodiments, the target nucleic acid is cDNA. In some embodiments, the solid support is a bead. In some embodiments, the plurality of solid supports are plurality of beads and wherein the plurality of beads are of different sizes.

In some embodiments, a single barcode sequence is present in the plurality of immobilized oligonucleotides on each individual solid support. In some embodiments, different barcode sequences are present in the plurality of immobilized oligonucleotides on each individual solid support. In some embodiments, the transferring of the barcode sequence information to the target nucleic acid fragments is by ligation. In some embodiments, transferring of the barcode sequence information to the target nucleic acid fragments is by polymerase extension. In some embodiments, the transferring of the barcode sequence information to the target nucleic acid fragments is by both ligation and polymerase extension. In some embodiments, the polymerase extension is by extending the 3'-end of the non-ligated transposon strand with a DNA polymerase using the ligated immobilized oligonucleotide as a template. In some embodiments, at least a portion of the adaptor sequences further comprise a second barcode sequence.

In some embodiments, the transposome complexes are multimeric, and wherein the adaptor sequences of the transposons of each monomeric unit are different from the other monomeric unit in the same transposome complex. In some embodiments, the adaptor sequence further comprises a first primer binding sequence. In some embodiments, the first primer binding site has no sequence homology to the capture sequence or to the complement of the capture sequence. In some embodiments, the immobilized oligonucleotides on the solid support further comprise a second primer binding sequence.

In some embodiments, the transposome complexes are multimeric, and the transposome monomeric units are linked to each other in the same transposome complex. In some embodiments, the transposase of a transposome monomeric unit is linked to the transposase of another transposome monomeric unit of the same transposome complex. In some embodiments, the transposons of a transposome monomeric unit are linked to transposons of another transposome monomeric unit of the same transposome complex. In some embodiments, the transposase of a transposome monomeric unit is linked to the transposase of another transposome monomeric unit of the same transposome complex by covalent bond. In some embodiments, the transposases of one monomeric unit is linked to the transposase of another transposome monomeric unit of the same transposome complex by di-sulfide bond. In some embodiments, the transposons of a transposome monomeric unit are linked to transposons of another transposome monomeric unit of the same transposome complex by covalent bond.

In some embodiments, the contiguity information of a target nucleic acid sequence is indicative of haplotype information. In some embodiments, the contiguity information of a target nucleic acid sequence is indicative of genomic variants. In some embodiments, the genomic variants are selected from the group consisting of deletions, translocations, interchromosomal gene fusions, duplications, and paralogs. In some embodiments, the oligonucleotides immobilized on the solid support comprise a partially double stranded region and a partially single stranded region. In some embodiments, the partially single stranded region of the oligonucleotide comprises the second barcode sequence and the second primer binding sequence. In some embodiments, the target nucleic acid fragments comprising the barcodes are amplified prior to determining the sequence of the target nucleic acid fragments. In some embodiments, subsequent amplification are carried out in a single reaction compartment prior to determining the sequence of the target nucleic acid fragments. In some embodiments, a third barcode sequence is introduced to the target nucleic acid fragments during the amplification.

In some embodiments, the methods may further include combining the target nucleic acid fragments comprising the barcodes from plurality of first set of reaction compartments into a pool of target nucleic acid fragments comprising the barcodes; redistributing the pool of target nucleic acid fragments comprising the barcodes to a plurality of second set of reaction compartments; and introducing a third barcode in to the target nucleic acid fragments by amplifying the target nucleic acid fragments in the second set of reaction compartments prior to sequencing.

In some embodiments, the methods may further include pre-fragmenting the target nucleic acid prior to contacting the target nucleic acid with transposome complexes. In some embodiments, the pre-fragmenting the target nucleic acid is by a method selected from the group consisting of sonication and restriction digestion.

BRIEF DESCRIPTION OF THE DRAWINGS

FIG. 1 illustrates a flow diagram of an example of a method of binding transposomes to a bead surface.

FIG. 5 shows a data table of another example of the reproducibility of the bead-based tagmentation process of FIG. 3 in terms of uniform size.

FIG. 26 shows the results of testing the feasibility of preparing indexed sequencing libraries of CPT-DNA on beads by intra-molecular hybridization.

FIGS. 30 and 31 show the schematics of indexed clonal bead transposition in a single reaction vessel (one pot) and the results of the transposition.

FIG. 32 shows the schematics of creating clonal transposomes on beads using 5'- or 3'-biotinylated oligonucleotides.

FIG. 44 shows an alternative exemplary scheme of simultaneous phasing and methylation detection.

FIG. 50 shows ME sequences before (SEQ ID NO: 5) and after (SEQ ID NO: 6) bisulfite conversion.

FIG. 52 shows the results after bisulfite conversion in IVC plot (intensity versus cycles per individual base).

FIG. 57 shows some possible mechanisms of ME swapping.

FIG. 62 shows an exemplary scheme of conjugation of transposome dimer to an amine coated solid support.

FIG. 64 shows a diagram of indexed linked reads for assembly/phasing of pseudogenes and the advantage of identifying variants in pseudogene using shorter fragments.

FIG. 65 shows a plot of index exchange from 4 separate experiments and shown as % of indexes swapped.

FIG. 71 discloses SEQ ID NOS 7, 7, 8, 7 and 8, respectively, in order of appearance.

FIG. 75A shows a chart of various conditions for bisulfite conversion (BSC) and the sequences of unconverted mosaic ends (ME) and BSC ME (SEQ ID NOS 5 and 6, respectively, in order of appearance).

FIG. 75B shows the results of bisulfite conversion efficiency optimization in an image of a gel and a bar graph that shows varied bisulfite conversion efficiency under different conditions.

DETAILED DESCRIPTION

Embodiments of the present invention relate to sequencing nucleic acids. In particular, embodiments of the methods and compositions provided herein relate to preparing nucleic acid templates and obtaining sequence data therefrom.

In one aspect, the present invention relate to methods of tagmenting (fragmenting and tagging) target nucleic acid on a solid support for the construction of a tagmented target nucleic acid library. In one embodiment, the solid support is a bead. In one embodiment, the target nucleic acid is DNA.

In one aspect, the present invention relate to methods and compositions of solid-support, transposase-based methods that can derive contiguity information of a target nucleic acid. In some embodiments, the compositions and the methods can derive assembly/phasing information.

In one aspect, the present invention relate to methods and compositions to derive contiguity information by means of capturing contiguously-linked, transposed, target nucleic acid onto a solid support.

In one aspect the compositions and methods disclosed herein relate to analysis of genomic variants. Exemplary genomic variants include but are not limited to deletions, inter chromosomal translocations, duplications, paralogs, interchromosomal gene fusions. In some embodiments, the compositions and methods disclosed herein relate to determining phasing information of the genomic variants.

In one aspect, the compositions and methods disclosed herein relate to phasing specific regions of the target nucleic acid. In one embodiment, the target nucleic acid is DNA. In one embodiment, the target nucleic acid is genomic DNA. In some embodiments, the target nucleic acid is RNA. In some embodiments, the RNA is mRNA. In some embodiments, the target nucleic acid is complimentary DNA (cDNA). In some embodiments, target nucleic acid is from a single cell. In some embodiments, target nucleic acid is from circulating tumor cells. In some embodiments, target nucleic acid is cell free DNA. In some embodiments, target nucleic acid is cell free tumor DNA. In some embodiments, target nucleic acid is from formalin fixed paraffin embedded tissue samples. In some embodiments, target nucleic acid is cross-linked target nucleic acid. In some embodiments, target nucleic acid is cross-linked to proteins. In some embodiments, target nucleic acid is cross-linked to nucleic acid. In some embodiments, target nucleic acid is histone-protected DNA. In some embodiments, histone-protected DNA is precipitated from a cell lysate using antibodies to histones and the histones are removed.

Figure 41:
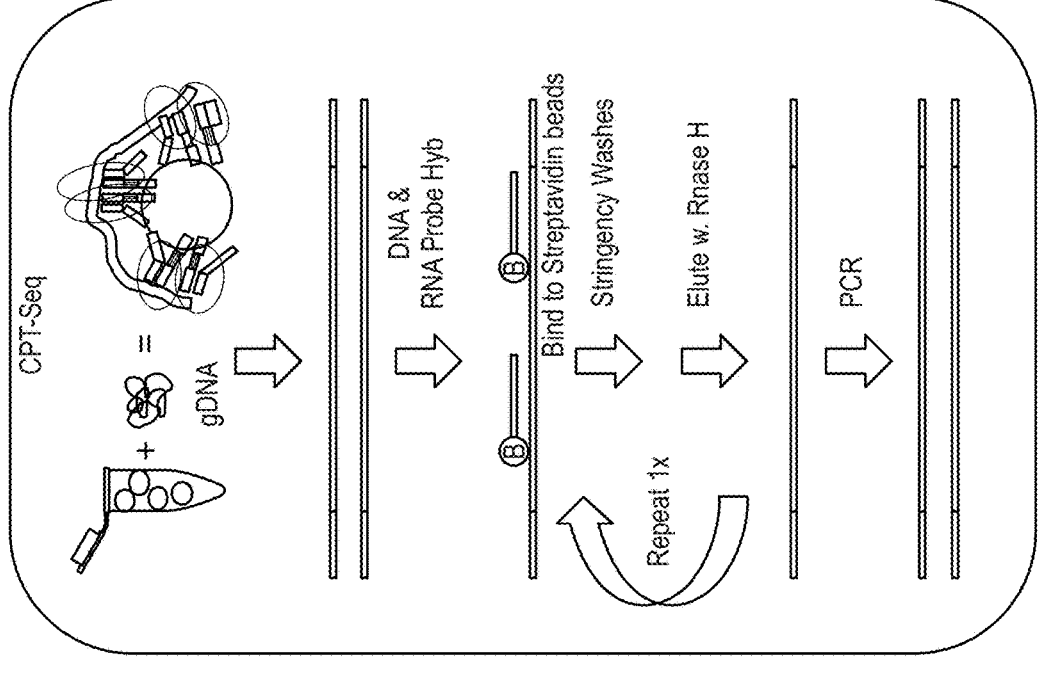
FIG. 41 shows an exemplary scheme of targeted phasing by enriching specific regions of a genome.

In some aspects, indexed libraries are created from the target nucleic acid using the clonally indexed beads. In some embodiments, the tagmented target nucleic acid, while the transposase is still bound to the target DNA can be captured using the clonally indexed beads. In some embodiments, specific capture probes are used to capture the specific region of interest in the target nucleic acid. The captured regions of the target nucleic acid can be washed at various stringencies and optionally amplified, followed by sequencing. In some embodiments, the capture probe may be biotinylated. The complex of the biotinylated capture probes hybridized to the specific regions of the indexed target nucleic acids can be separated by using streptavidin beads. Exemplary scheme of targeted phasing is shown in FIG. 41.

Figure 42:
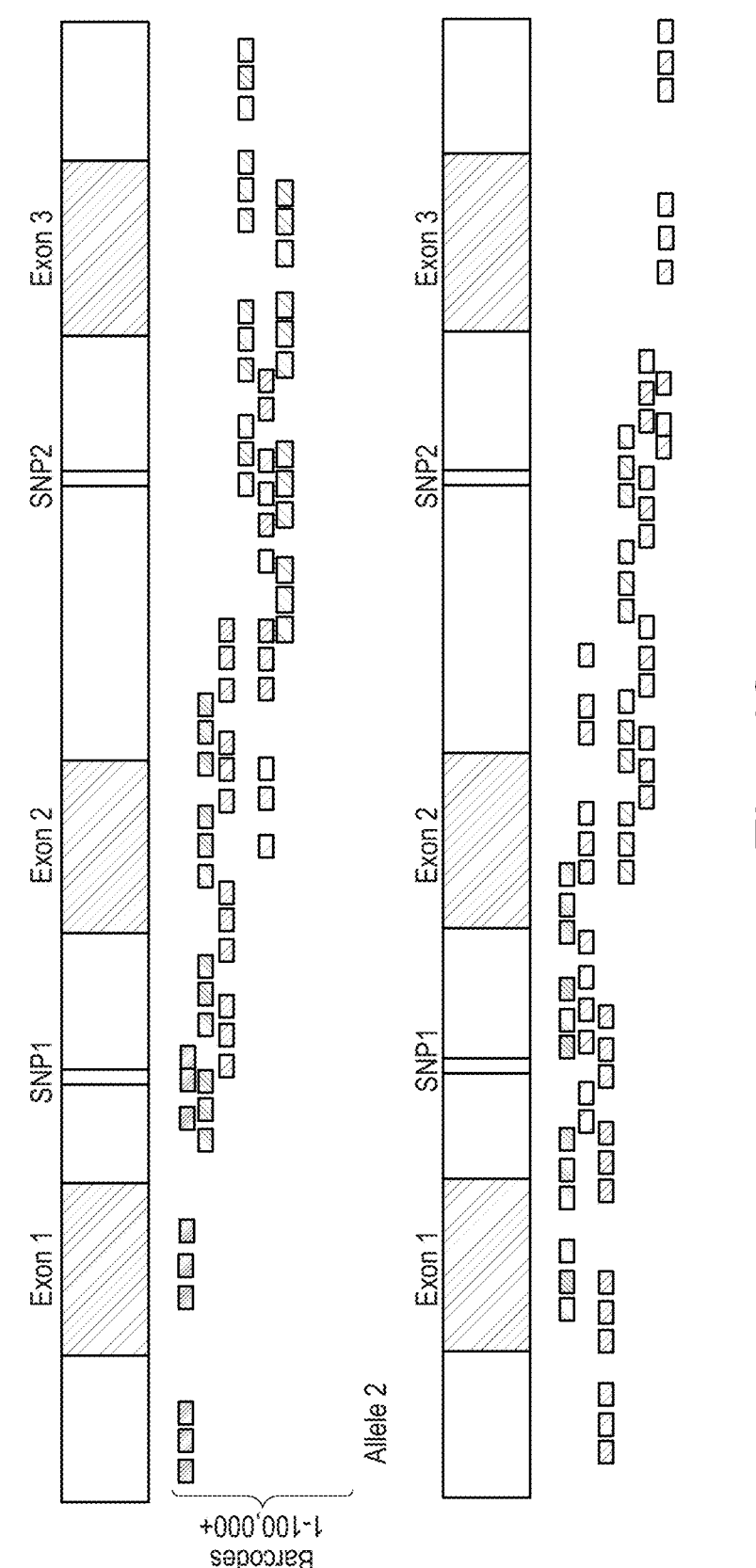
FIG. 42 shows an exemplary scheme of exome phasing using the SNPs between the exons.

In some aspects, the compositions and methods disclosed herein can be used phasing exomes. In some embodiments, exons, promoters can be enriched. Markers, for example, heterozygous SNPs between exonic regions, can aid in phasing the exons, especially when the distance between exons is large. Exemplary exome phasing is shown in FIG. 42. In some embodiments, indexed linked reads cannot span (cover) heterozygous SNPs of neighboring exons simultaneously. As such, it is challenging to phase the two or more exons. The compositions and methods disclosed herein also enriches heterozygous SNPs between exons for example, phasing exons 1 to SNP1 and SNP2 to Exon 2. As such, through the use of SNP 1, exon 1 and exon 2 can be phased as shown in FIG. 42.

In one aspect, the compositions and methods disclosed herein can be used for phasing and simultaneous methylation detection. Methylation detection through bisulfite conversion (BSC) is challenging as the BSC reaction is harsh on DNA, fragmenting the DNA and therefore removing contiguity/phasing information. Also, methods disclosed in the present application has an additional advantage because no additional purification steps are required in contrast to those required in traditional BSC approaches, thereby improving the yield.

In one aspect, the compositions and methods disclosed herein can be used to prepare different size libraries in single assay. In some embodiment, different sizes of clonally indexed beads can be used to prepare different size libraries. FIG. 1 illustrates a flow diagram of an example of a method 100 of binding transposomes to a bead surface. Transposomes may be bound to a bead surface using any chemistry that may be added on the transposon oligonucleotide, transposase, and solid-phase. In one example, transposomes are bound to a bead surface via a biotin-streptavidin binding complex. Method 100 includes, but is not limited to, the following steps.

In one embodiment, transposons may comprise sequencing primer binding sites. Exemplary sequences of sequence binding sites include, but are not limited to AATGA-TACGGCGACCACCGAGATCTACAC (P5 sequence) (SEQ ID NO: 1) and CAAGCAGAAGACGGCAT-ACGAGAT (P7 sequence) (SEQ ID NO: 2). In some embodiments, the transposons may be biotinylated.

At a step 110 of FIG. 1, P5 and P7 biotinylated transposons are generated. The transposons may also include one or more index sequence (unique identifier). Exemplary index sequences include, but are not limited to TAGATCGC, CTCTCTAT, TATCCTCT, AGAGTAGA, GTAAGGAG, ACTGCATA, AAGGAGTA, CTAAGCCT. In another example, only the P5 or only the P7 transposons are biotinylated. In yet another example, the transposons comprise only the mosaic end (ME) sequences or the ME sequences plus additional sequences that are not P5 and P7 sequences. In this example, P5 and P7 sequences are added in a subsequent PCR amplification step.

At a step 115 of FIG. 1, the transposomes are assembled. The assembled transposomes are a mixture of P5 and P7 transposomes. A mixture of P5 and P7 transposomes are described in more detail with reference to FIGS. 11 and 12.

At a step 120 of FIG. 1, P5/P7 transposome mixtures are bound to a bead surface. In this example, the beads are streptavidin coated beads and the transposomes are bound to the bead surface via a biotin-streptavidin binding complex. Beads can be of various sizes. In one example, the beads may be 2.8 μm beads. In another example, the beads may be 1 μm beads. A suspension (e.g., 1 μL) of 1 μm beads provides a large surface area per volume for transposomes binding. Because of the available surface area for transposomes binding, the number of tagmentation products per reaction is increased.

Figure 2:
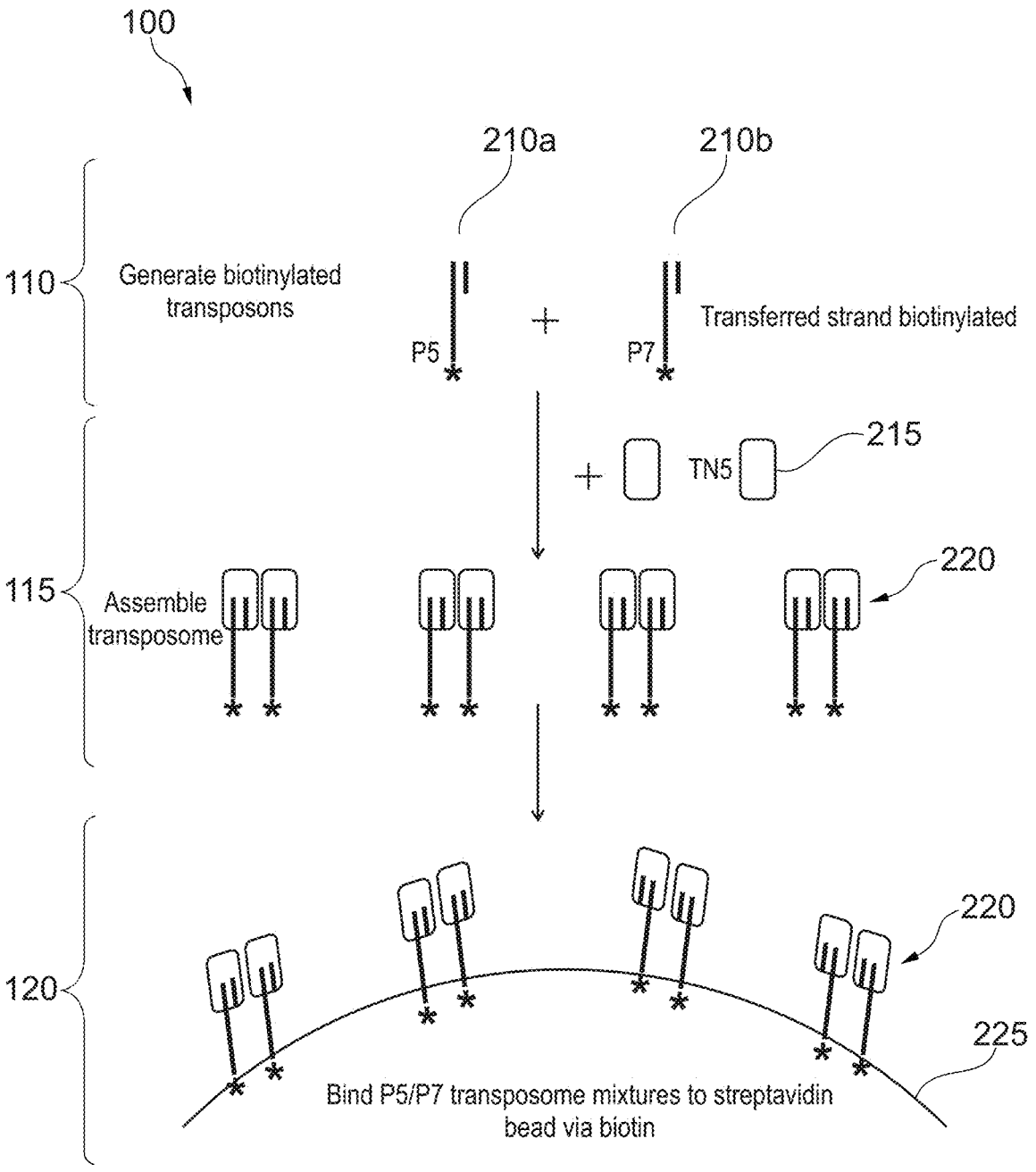
FIG. 2 shows pictorially the steps of the method of FIG. 1.

FIG. 2 shows pictorially the steps 110, 115, and 120 of method 100 of FIG. 1. In this example, the transposons are shown as duplexes. In another example (not shown), another structure such as a hairpin, i.e., a single oligonucleotide with regions of self-complementarity capable of forming a duplex, may be used.

At step 110 of method 100, a plurality of biotinylated P5 transposons 210a and a plurality of P7 transposons 210b are generated. P5 transposons 210a and P7 transposons 210b are biotinylated.

At step 115 of method 100, P5 transposons 210a and P7 transposons 210b are mixed with transposase Tn5 215 to form a plurality of assembled transposomes 220.

At step 120 of method 100, transposomes 220 are bound to a bead 225. Bead 225 is a streptavidin coated bead. Transposomes 220 are bound to bead 225 via a biotin-streptavidin binding complex.

In one embodiment, a mixture of transposomes may be formed on a solid support such as bead surface as shown in FIGS. 10, 11, 12, and 13. In this example, P5 and P7 oligonucleotides are first bound to a bead surface prior to assembly of transposome complexes.

Figure 3:
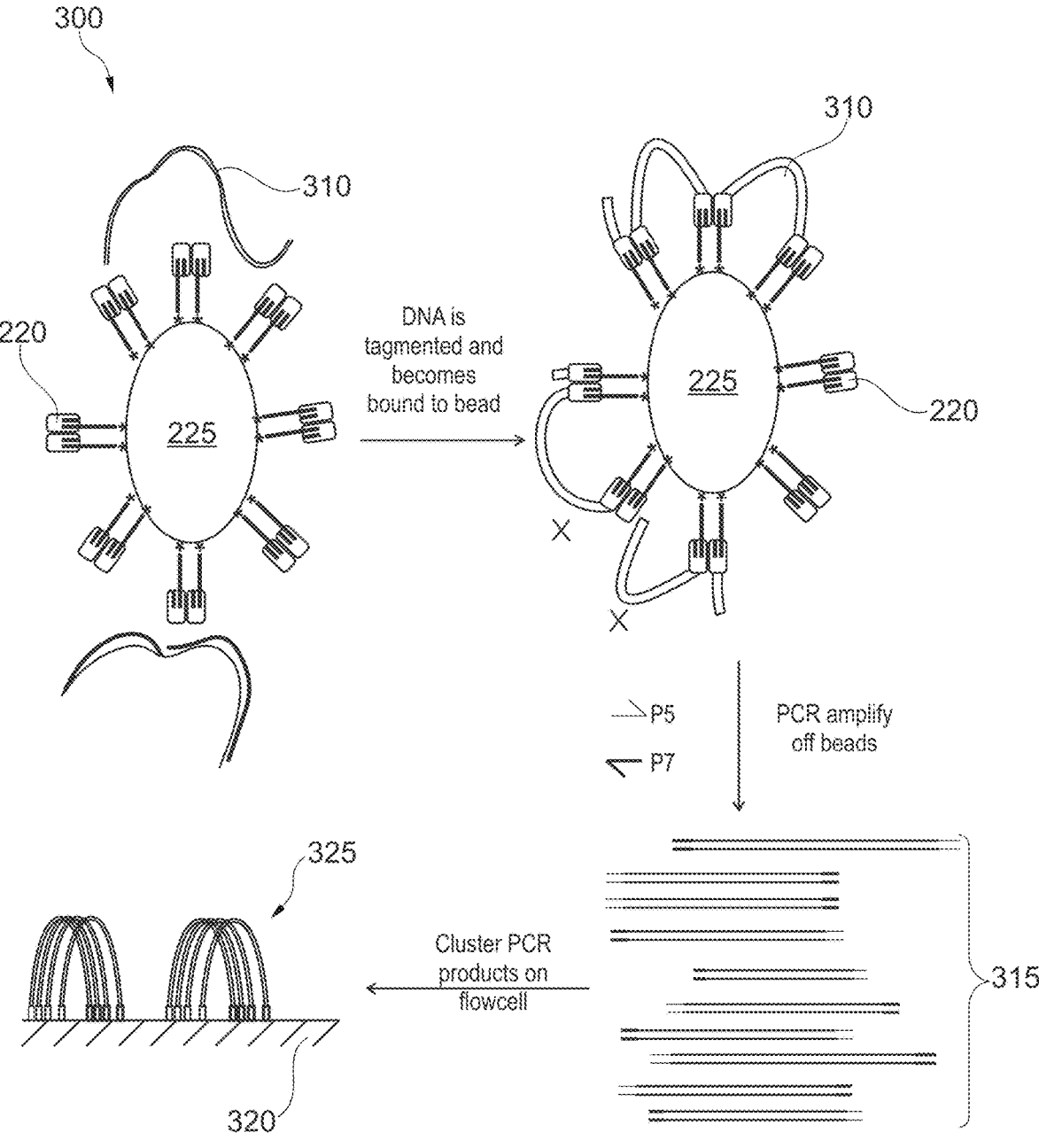
FIG. 3 illustrates a schematic diagram of an example of a tagmentation process on a bead surface.

FIG. 3 illustrates a schematic diagram of an example of a tagmentation process 300 on a bead surface. Shown in process 300 is bead 225 of FIG. 2 with transposomes 220 bound thereon. A solution of DNA 310 is added to a suspension of beads 225. As DNA 310 contacts transposomes 220, the DNA is tagmented (fragmented and tagged) and is bound to beads 225 via transposomes 220. Bound and tagmented DNA 310 may be PCR amplified to generate a pool of amplicons 315 in solution (bead-free). Amplicons 315 may be transferred to the surface of a flow cell 320. A cluster generation protocol (e.g., a bridge amplification protocol or any other amplification protocol that may be used for cluster generation) may be used to generate a plurality of clusters 325 on the surface of flow cell 320. Clusters 325 are clonal amplification products of tagmented DNA 310. Clusters 325 are now ready for the next step in a sequencing protocol.

In another embodiment, the transposomes may be bound to any solid surface, such as the walls of a microfuge tube.

Figure 10:
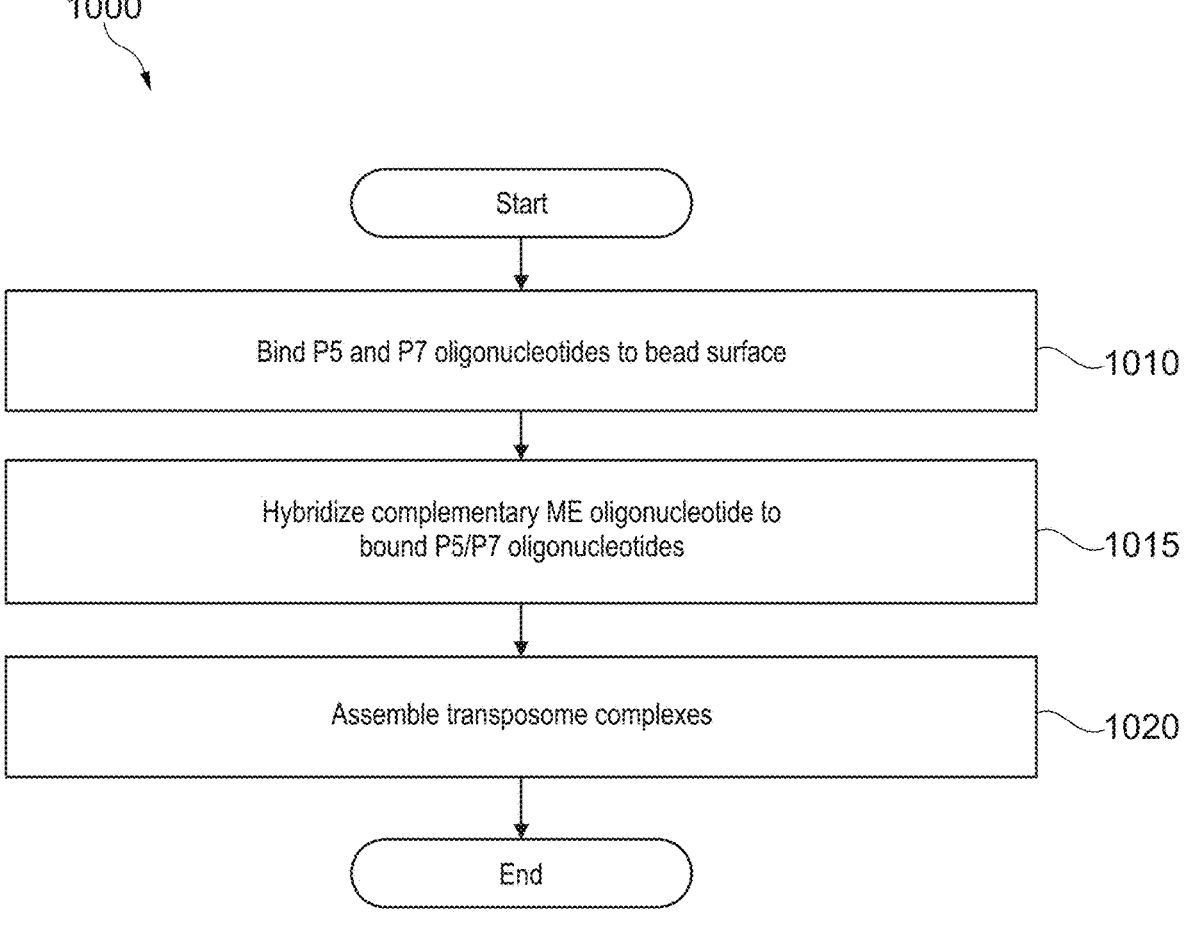
FIG. 10 illustrates a flow diagram of an example of a method of forming transposome complexes on a bead surface.

In another embodiment of forming a mixture of transposome complexes on a bead surface, oligonucleotides are first bound to a bead surface prior to transposome assembly. FIG. 10 illustrates a flow diagram of an example of a method 1000 of forming transposome complexes on a bead surface. Method 1000 includes, but is not limited to, the following steps.

Figure 11:
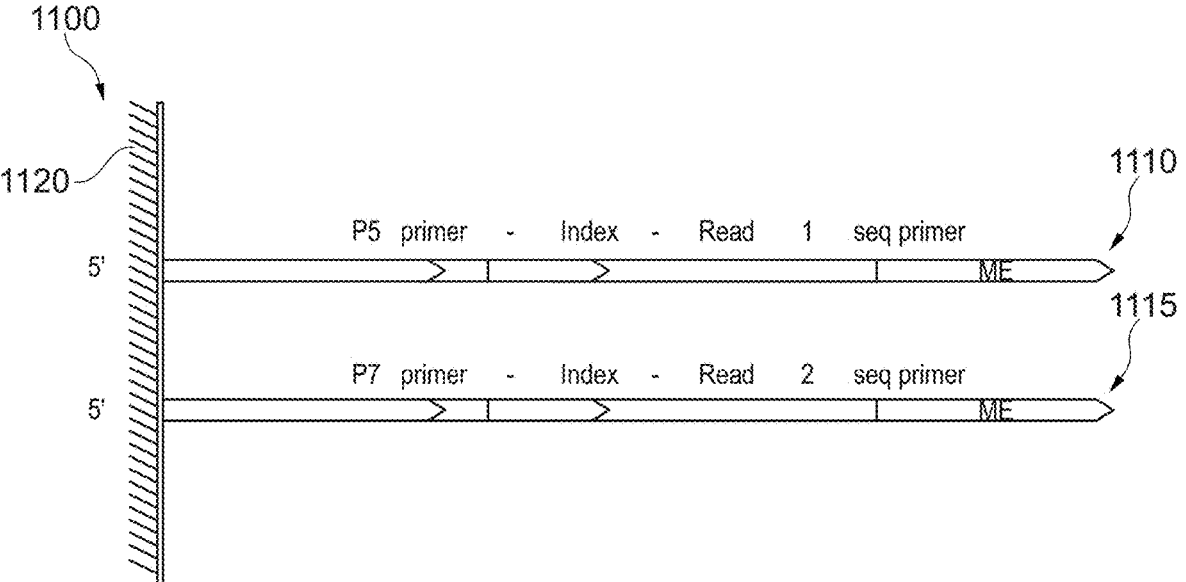
FIGS. 11, 12, and 13 show pictorially the steps of the method of FIG. 10.

At a step 1010, P5 and P7 oligonucleotides are bound to a bead surface. In one example, the P5 and P7 oligonucleotides are biotinylated and the bead is a streptavidin coated bead. This step is also shown pictorially in schematic diagram 1100 of FIG. 11. Referring now to FIG. 11, a P5 oligonucleotide 1110 and a P7 oligonucleotide 1115 are bound to the surface of a bead 1120. In this example, a single P5 oligonucleotide 1110 and a single P7 oligonucleotide 1115 are bound to the surface of bead 1120, but any number of P5 oligonucleotides 1110 and/or P7 oligonucleotides 1115 may be bound to the surface of a plurality of beads 1120. In one example, P5 oligonucleotide 1110 comprises a P5 primer sequence, an index sequence (unique identifier), a read 1 sequencing primer sequence and a mosaic end (ME) sequence. In this example, P7 oligonucleotide 1115 comprises a P7 primer sequence, an index sequence (unique identifier), a read 2 sequencing primer sequence and an ME sequence. In another example (not shown), an index sequence is present in only P5 oligonucleotide 1110. In yet another example (not shown), an index sequence is present in only the P7 oligonucleotide 1115. In yet another example (not shown), an index sequence is absent in both P5 oligonucleotide 1110 and P7 oligonucleotide 1115.

Figure 12:
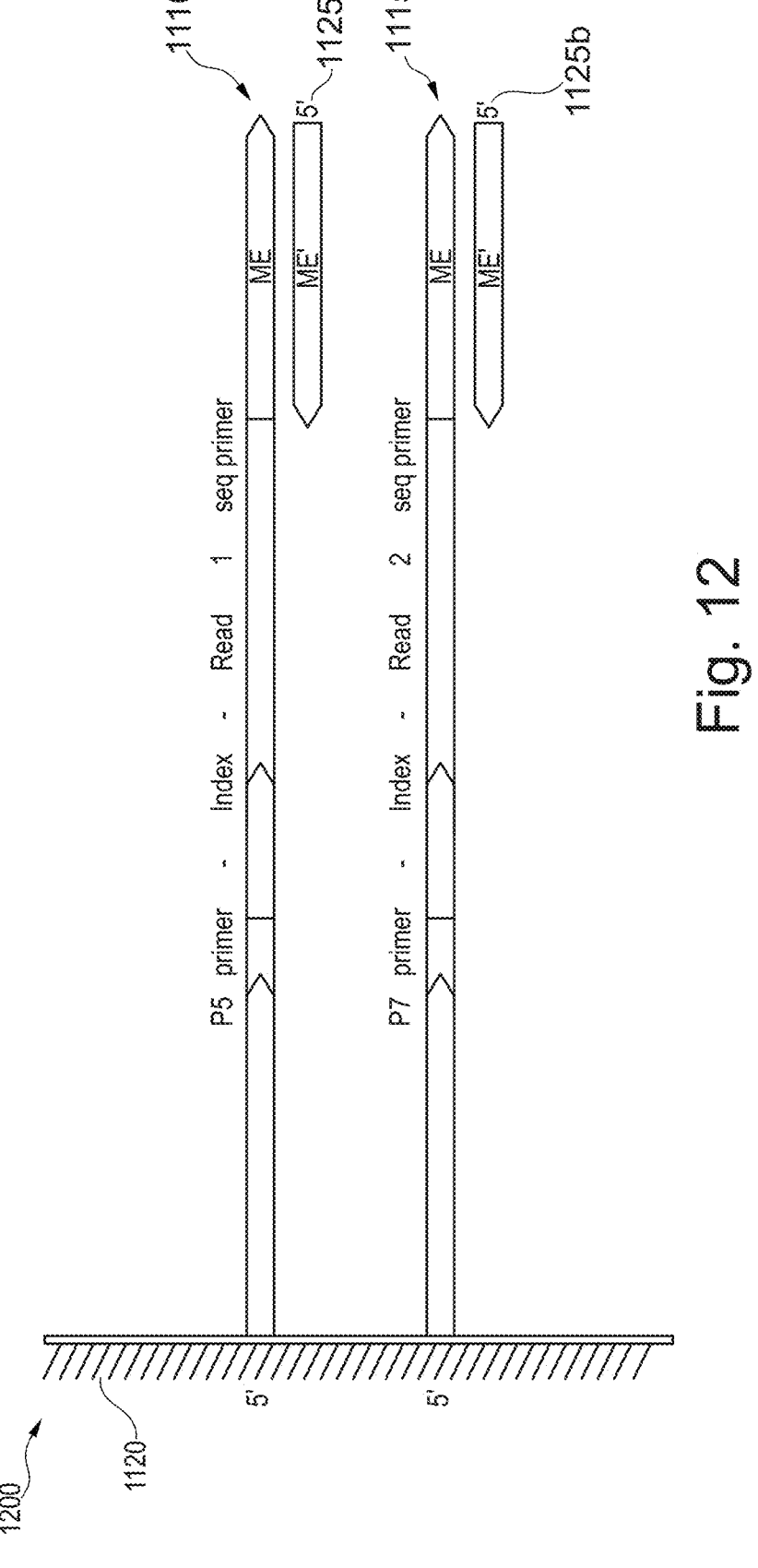

At a step 1015, complementary mosaic end (ME') oligonucleotides are hybridized to the bead-bound P5 and P7 oligonucleotides. This step is also shown pictorially in schematic diagram 1200 of FIG. 12. Referring now to FIG. 12, complementary ME sequences (ME') 1125 are hybrid to P5 oligonucleotide 1110 and P7 oligonucleotide 1115. Complementary ME sequences (ME') 1125 (e.g., complementary ME sequences (ME') 1125a and complementary ME sequences (ME') 1125b) hybridize to the ME sequences in P5 oligonucleotide 1110 and P7 oligonucleotide 1115, respectively. Complementary ME sequence (ME') 1125 is typically about 15 bases in length and phosphorylated at its 5' end.

Figure 13:
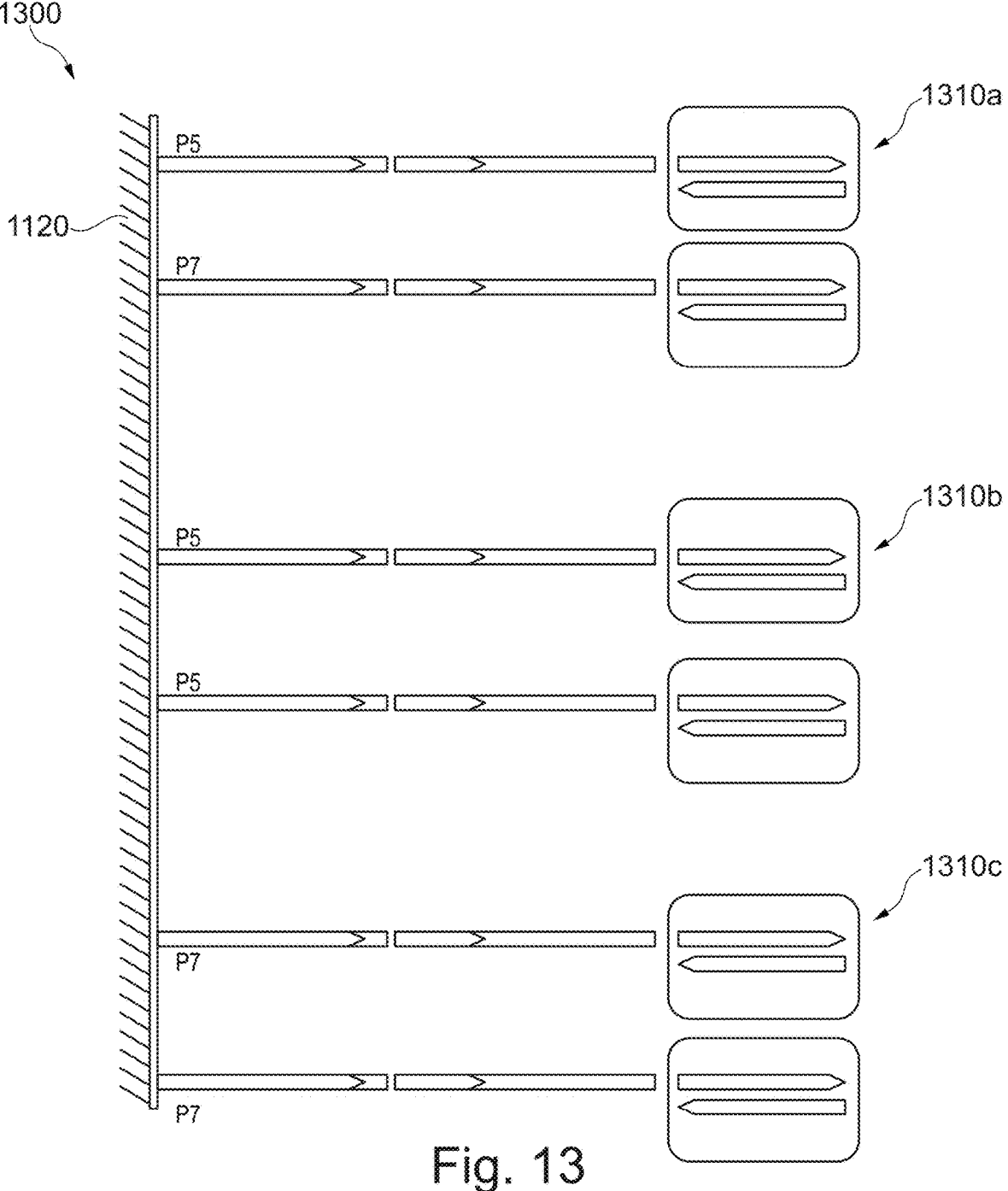

At a step 1020, transposase enzyme is added to the bead-bound oligonucleotides to form a mixture of bead-bound transposome complexes. This step is also shown pictorially in schematic diagram 1300 of FIG. 13. Referring now to FIG. 13, transposase enzyme is added to form a plurality of transposome complexes 1310. In this example, transposome complex 1310 is a duplex structure that comprises transposase enzyme, two surface-bound oligonucleotide sequences, and their hybridized complementary ME sequences (ME') 1125. For example, transposome complex 1310a comprises P5 oligonucleotide 1110 hybridized to complementary ME sequence (ME') 1125 and P7 oligonucleotide 1115 hybridized to complementary ME sequence (ME') 1125 (i.e., P5:P7); transposome complex 1310b comprises two P5 oligonucleotides 1110 hybridized to complementary ME sequences (ME') 1125 (i.e., P5:P5); and transposome complex 1310c comprises two P7 oligonucleotides 1115 hybridized to complementary ME sequences (ME') 1125 (i.e., P7:P7). The ratio of P5:P5, P7:P7, and P5:P7 transposome complexes may be, for example, 25:25:50, respectively.

Figure 14:
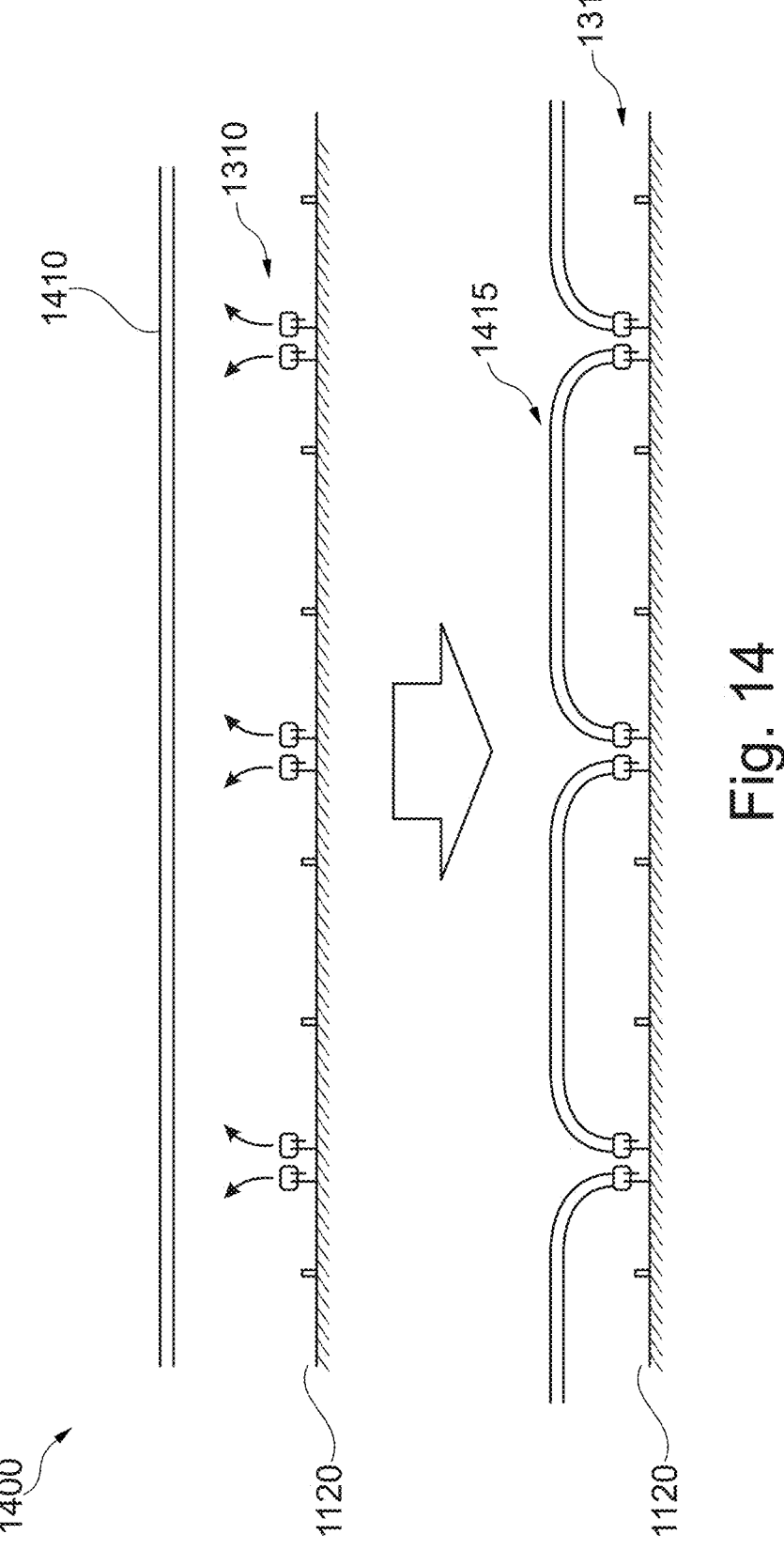
FIG. 14 shows a schematic diagram of a tagmentation process using the transposome coated bead shown in FIG. 13.

FIG. 14 shows an exemplary schematic diagram 1400 of a tagmentation process using the transposome coated bead 1120 of FIG. 13. In this example, when bead 1120 with transposome complexes 1310 thereon is added to a solution of DNA 1410 in a tagmentation buffer, tagmentation occurs and the DNA is linked to the surface of bead 1120 via transposomes 1310. Successive tagmentation of DNA 1410 results in a plurality of bridged molecules 1415 between transposomes 1310. The length of bridged molecules 1415 may be dependent on the density of transposome complexes 1310 on the surface of bead 1120. In one example, the density of transposome complexes 1310 on the surface of bead 1120 may be tuned by varying the amount of P5 and P7 oligonucleotides bound to the surface of bead 1120 in step 1010 of method 100 of FIG. 10. In another example, the density of transposome complexes 1310 on the surface of bead 1120 may be tuned by varying the amount of complementary ME sequence (ME') hybridized to P5 and P7 oligonucleotides in step 1015 of method 1000 of FIG. 10. In yet another example, the density of transposome complexes 1310 on the surface of bead 1120 may be tuned by varying the amount of transposase enzyme added in step 1020 of method 1000 of FIG. 1.

The length of bridged molecules 1415 is independent of the quantity of beads 1120 with transposome complexes 1310 bound thereon used in a tagmentation reaction. Similarly, adding more or less DNA 1410 in a tagmentation reaction does not alter the size of the final tagmented product, but may affect the yield of the reaction.

In one example, bead 1120 is a paramagnetic bead. In this example, purification of the tagmentation reaction is readily achieved by immobilizing beads 1120 with a magnet and washing. Therefore, tagmentation and subsequent PCR amplification may be performed in a single reaction compartment ("one-pot") reaction.

In one aspect, the present invention relate to methods and compositions of transposase-based methods that can derive contiguity information of a target nucleic acid on a solid support. In some embodiments, the compositions and the methods can derive assembly/phasing information. In one embodiment, the solid support is a bead. In one embodiment, the target nucleic acid is DNA. In one embodiment, the target nucleic acid is genomic DNA. In some embodiment, the target nucleic acid is RNA. In some embodiments, the RNA is mRNA. In some embodiments, the target nucleic acid is complimentary DNA (cDNA).

In some embodiments, transposons may be immobilized as dimers to solid-support such as beads, followed by the binding of transposase to the transposons to form transposomes.

Figure 15:
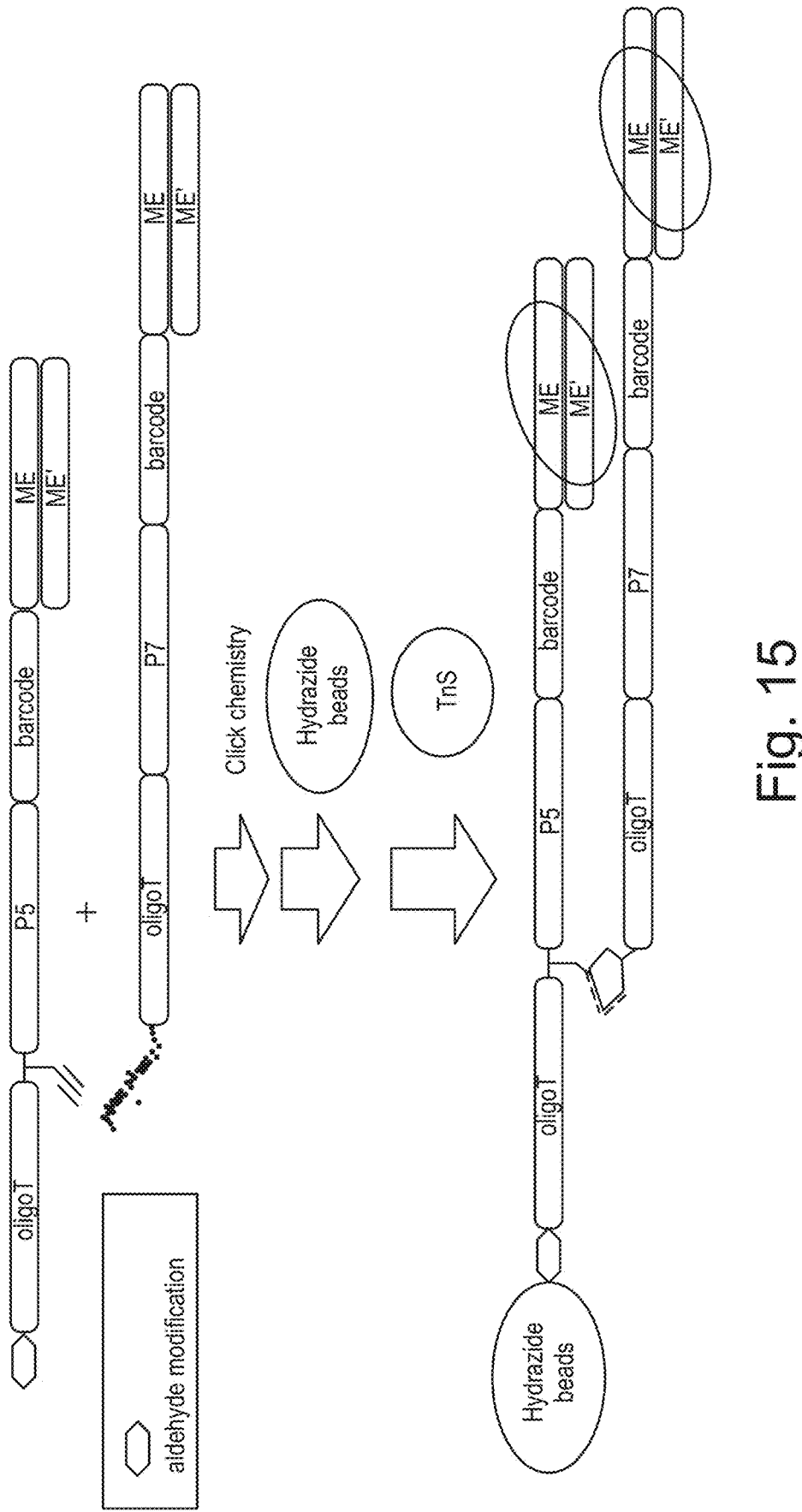
FIG. 15 shows an exemplary scheme of forming transposomes on a solid support.

In some embodiments, particularly related to formation of transposomes on solid-phases by solid-phase immobilized transposons and addition of transposase, two transposons may be immobilized in close proximity (preferably fixed distance) to one another in a solid support. There are several advantages to this approach. First, the two transposons will always be immobilized simultaneously, with preferably an optimum linker length and orientation of the two transposons to form transposomes efficiently. Second, transposome formation efficiency will not be a function of transposon density. Two transposons will always be available with the right orientation and distance between them to form transposomes. Third, with random immobilized transposons on surfaces, various distances are created between transposons, therefore only a fraction has the optimum orientation and distance to form transposomes efficiently. As a consequence, not all transposons are converted into transposomes and solid-phase immobilized non-complexed transposons will be present. These transposons are susceptible as a target to transposition as the ME-part is double-stranded DNA. This could result in a reduction of transposition efficiency or creates undesired side products. Thus, transposomes may be prepared on solid support, which can subsequently be used to derive contiguity information through tagmentation and sequencing. An exemplary scheme is illustrated in FIG. 15. In some embodiments, the transposons may be immobilized to the solid support by means other than chemical coupling. Exemplary methods of immobilizing transposons on the solid support may include, but are not limited to affinity binding such as streptavidin-biotin, maltose-maltose binding protein, antigen-antibody, DNA-DNA or DNA-RNA hybridization.

Figures 29A, 29B:
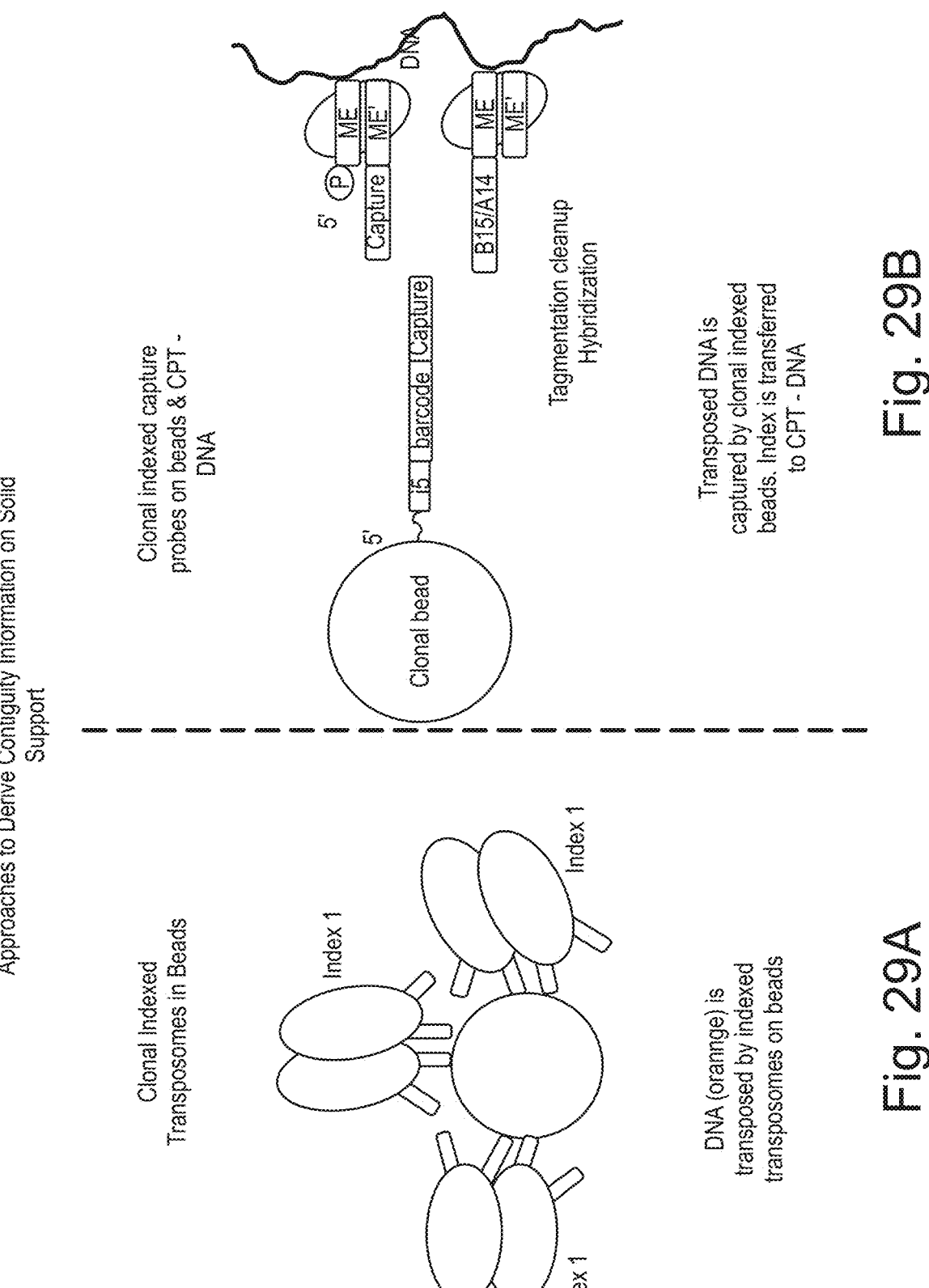
FIGS. 29A and 29B show exemplary approaches to derive contiguity information on solid support.

In some embodiments, transposomes can be pre-assembled and then immobilized on a solid-support. In some embodiments, the transposons comprise unique indexes, barcodes, and amplification primer binding sites. Transposase can be added in solution comprising transposons to form transposome dimers, which can be immobilized on a solid support. In one embodiment, multiple bead sets can be generated in which each set has the same index derived from the immobilized transposons thus generating indexed beads. Target nucleic acid can be added to each set of indexed beads as shown in FIG. 29A.

In some embodiments, target nucleic acid can be added to each set of indexed beads, tagmented and subsequent PCR amplification may be performed separately.

In some embodiments, target nucleic acid, indexed beads, and transposomes can be combined in droplets such that a number of droplets contain a single bead with one or more DNA molecules and adequate transposomes.

In some embodiments, the indexed beads can be pooled, target nucleic acid can be added to the pool, tagmented and subsequent PCR amplification may be performed in a single reaction compartment ("one-pot").

In one aspect, the present invention relate to methods and compositions to derive contiguity information by means of capturing contiguously-linked, transposed, target nucleic acid onto a solid support. In some embodiments, contiguity preserving transposition (CPT) is carried out on the DNA, but the DNA is kept intact (CPT-DNA), thus making contiguously-linked libraries. Contiguity information can be preserved by the use of transposase to maintain the association of template nucleic acid fragments adjacent in the target nucleic acid. The CPT-DNA can be captured by hybridization of complimentary oligonucleotides having unique indexes or barcodes and immobilized on solid support, e.g., beads (FIG. 29B). In some embodiments, the oligonucleotide immobilized on the solid support may further comprise primer binding sites, unique molecular indices (UMI), in addition to barcodes.

Advantageously, such use of transposomes to maintain physical proximity of fragmented nucleic acids increases the likelihood that fragmented nucleic acids from the same original molecule, e.g., chromosome, will receive the same unique barcode and index information from the oligonucleotides immobilized on a solid support. This will result in a contiguously-linked sequencing library with unique barcodes. The contiguously-linked sequencing library can be sequenced to derive contiguous sequence information.

Figure 16:
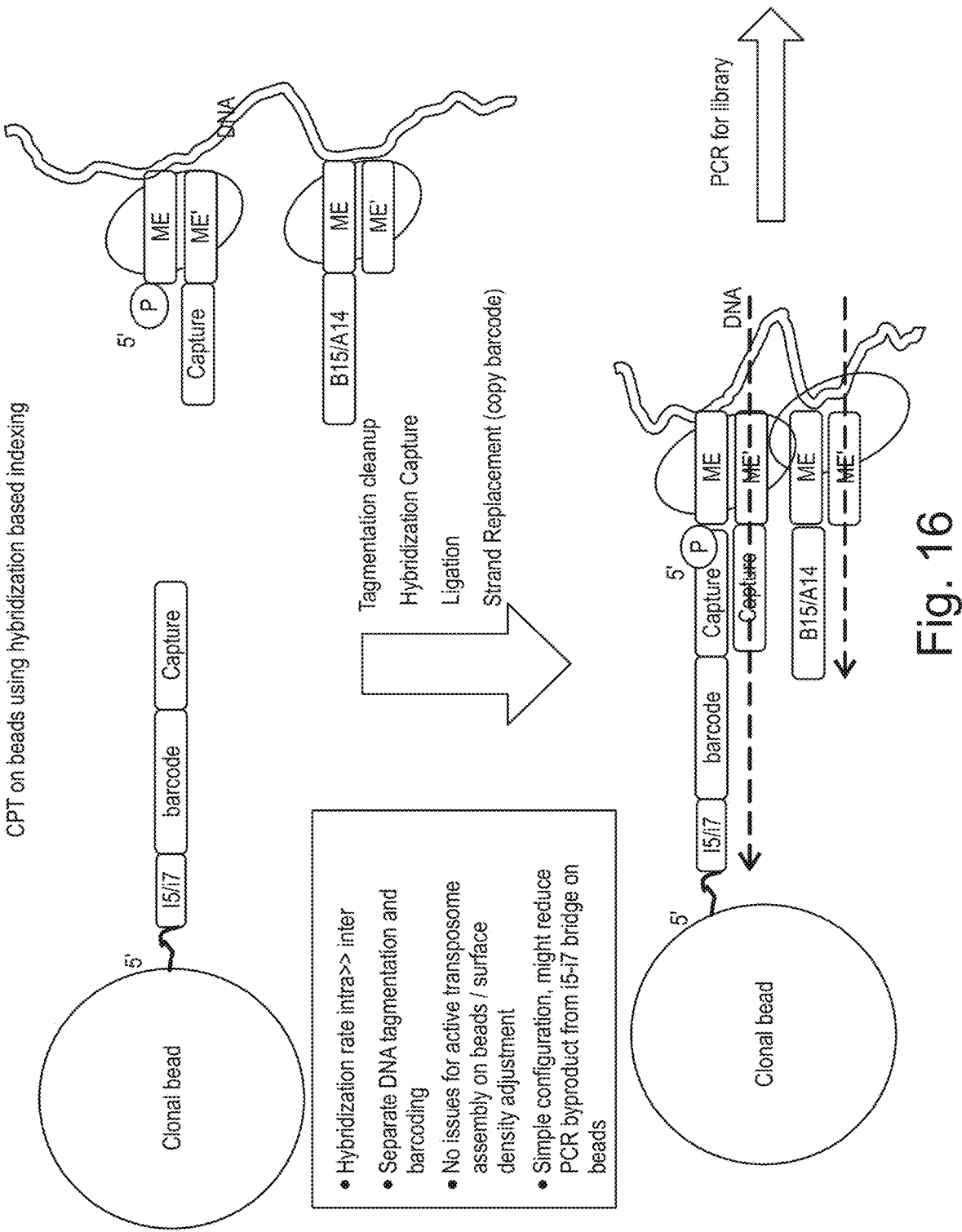
FIG. 16 shows an exemplary scheme of making contiguously-linked libraries with unique indexes.
Figure 17:
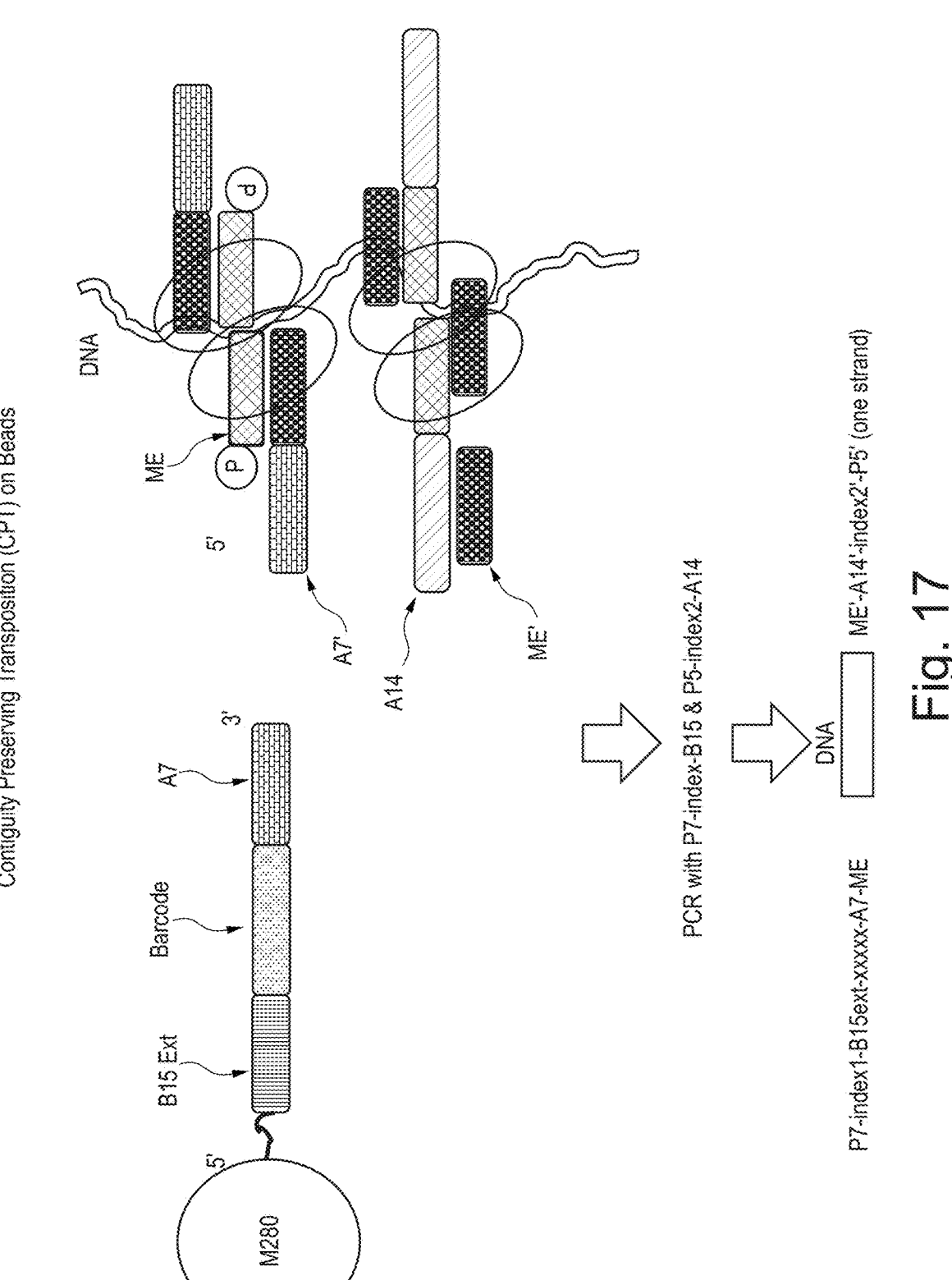
FIG. 17 shows an exemplary scheme of making contiguously-linked libraries with unique indexes.
Figure 18:
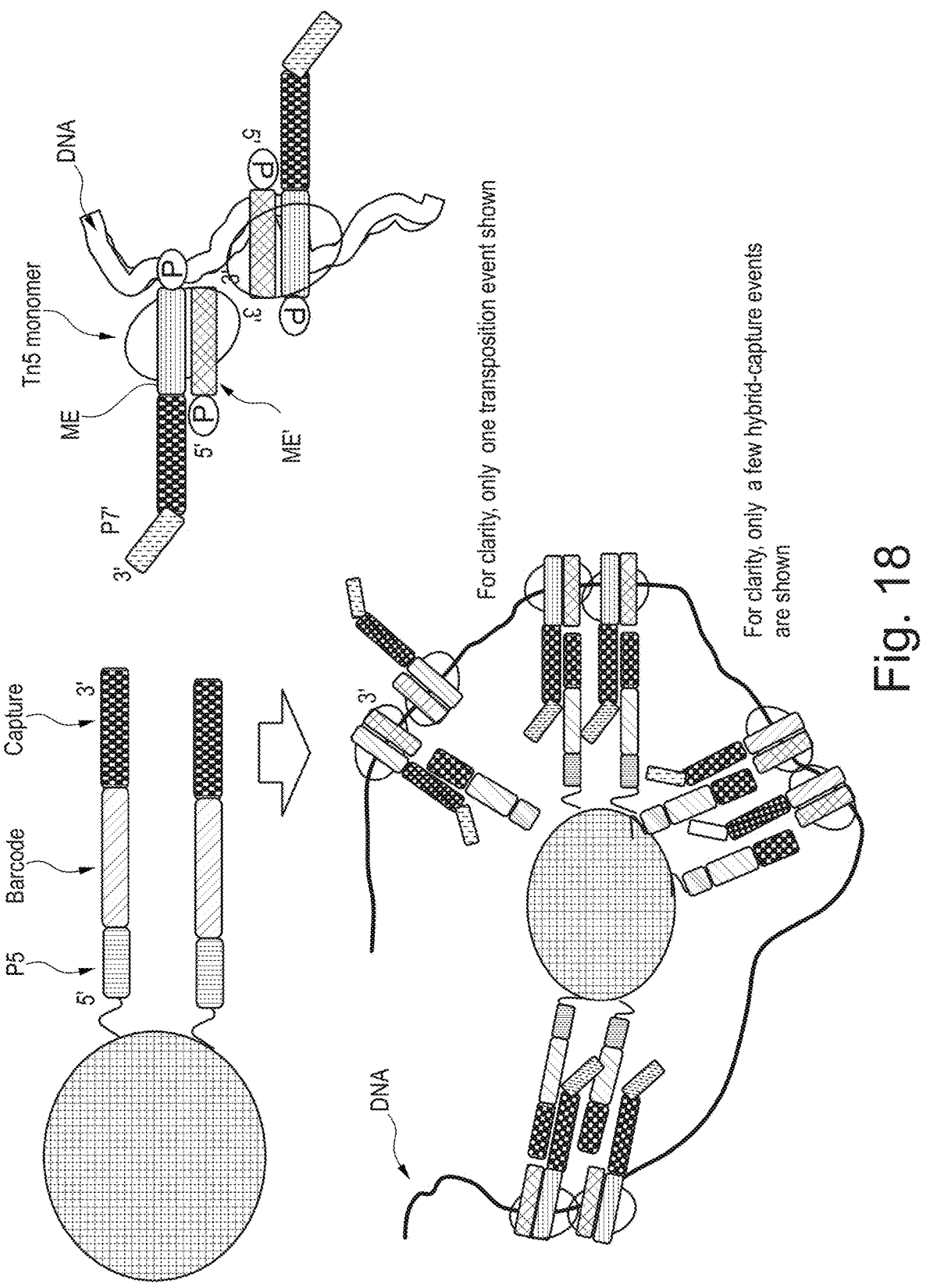
FIGS. 18 and 19 depicts the capture of a single CPT-DNA on a single clonal indexed bead where the CPT-DNA wraps around the bead.
Figure 19:
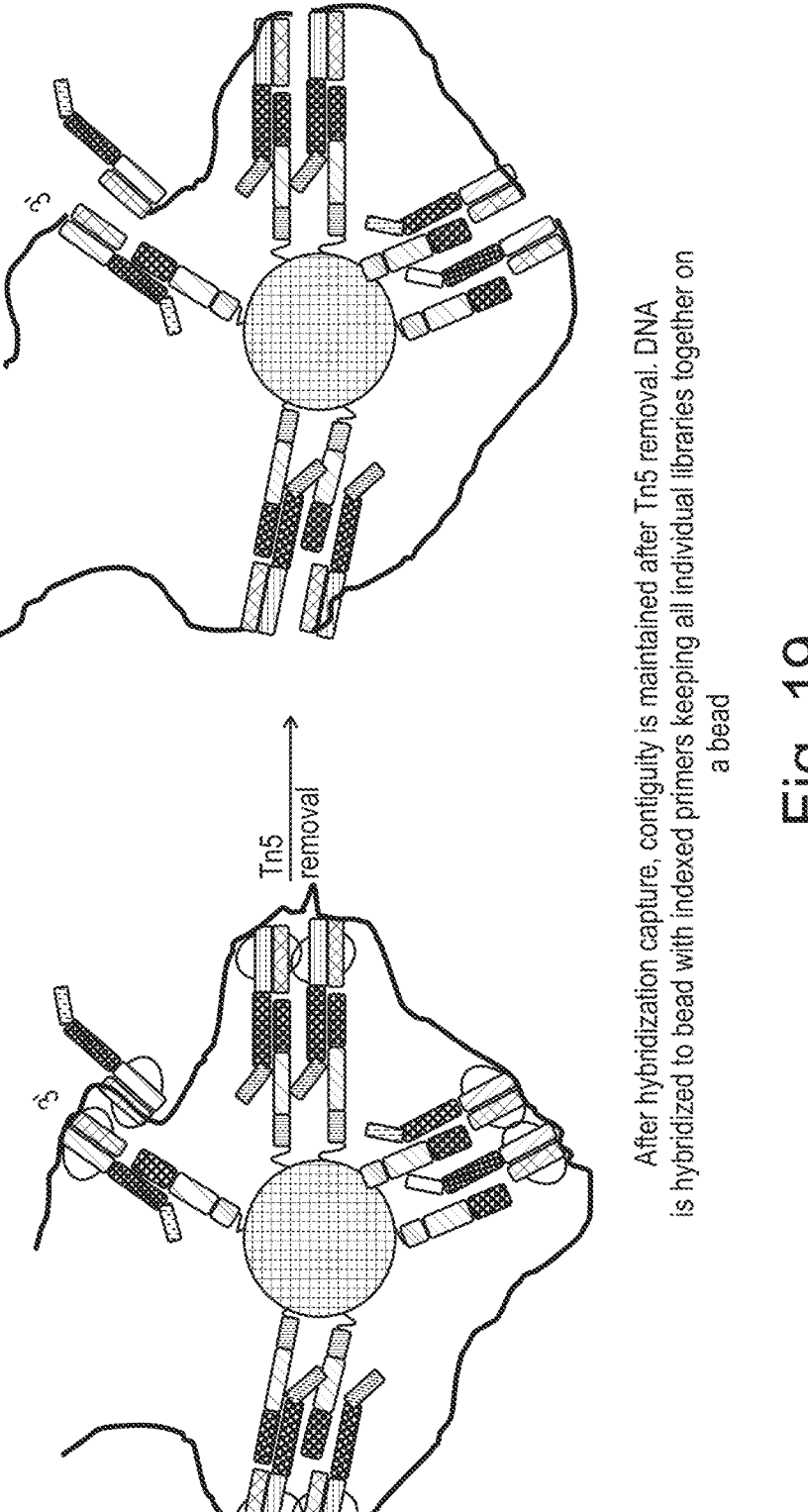

FIGS. 16 and 17 show schematic representations of an exemplary embodiment of the above aspect of the invention of making contiguously-linked libraries with unique barcodes or indices. The exemplary method leverages on ligation of the CPT-DNA with the immobilized oligonucleotides on the solid support comprising unique indexes and barcodes and strand-replacement PCR to generate a sequencing library. In one embodiment, clonal indexed beads may be generated with immobilized DNA sequences such as random or specific primer and index. Contiguously-linked libraries can be captured onto clonal-indexed beads by hybridization to the immobilized oligonucleotides followed by ligation. As intramolecular hybridization capture is much faster than intermolecular hybridization, contiguously-transposed libraries will "wrap" around the bead. FIGS. 18 and 19 depict the capture of the CPT-DNA on clonal indexed beads and the preservation of the contiguity information. Strand-replacement PCR can transfer the clonal bead index information to the individual molecule. Thus, each contiguously-linked library will be uniquely indexed.

Figure 20:
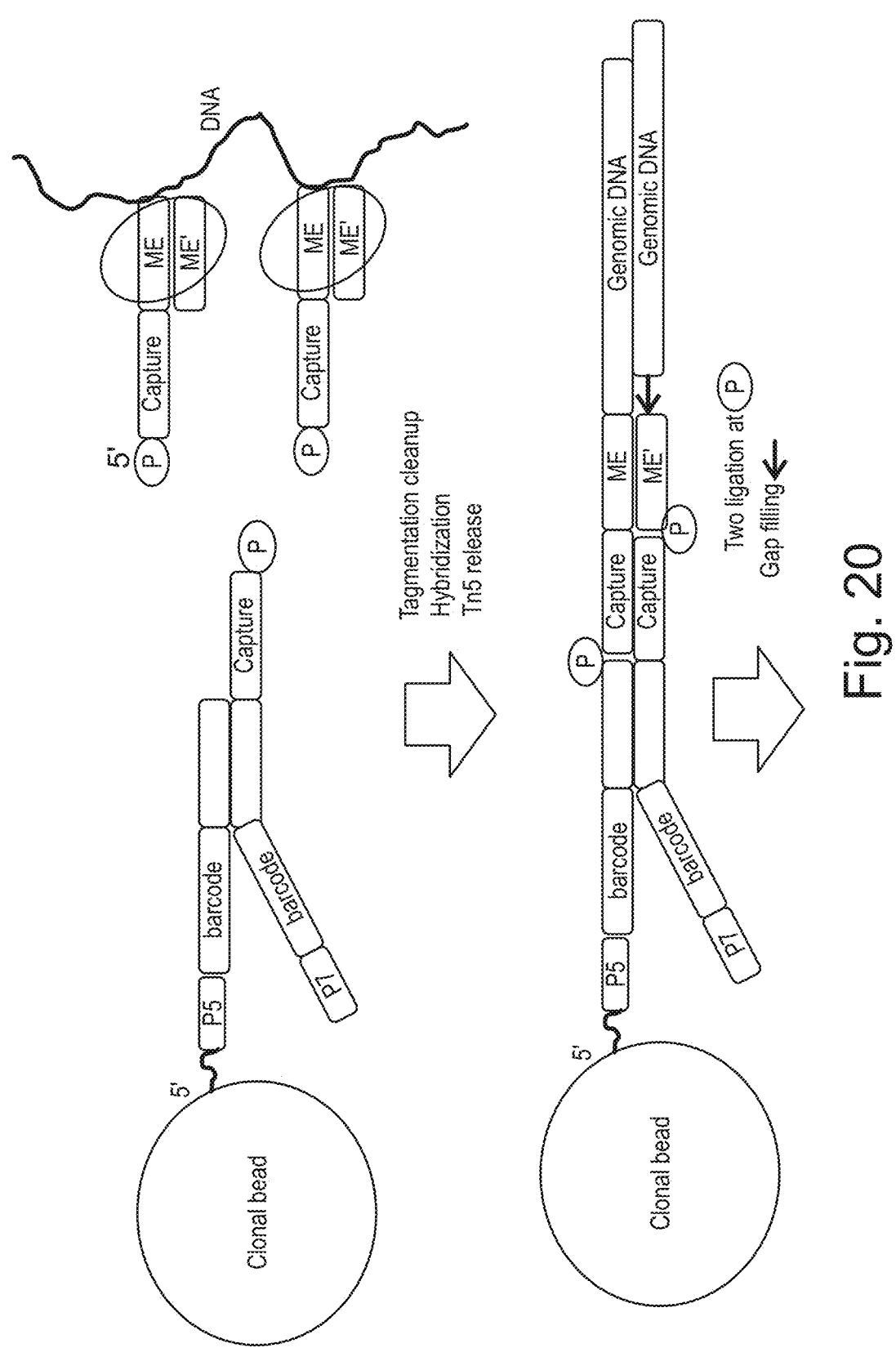
FIG. 20 shows an exemplary scheme of linking a Y-adaptor immobilized on the solid surface to the tagmented DNA by ligation and gap filling.

In some embodiments, the oligonucleotide immobilized on a solid support can comprise a partially double stranded structure such that one strand is immobilized to the solid support and the other strand is partially complementary to the immobilized strand resulting in a Y-adaptor. In some embodiments, the Y-adaptor immobilized on the solid surface is linked to the contiguously linked tagmented DNA by ligation and gap filling and shown in FIG. 20.

Figure 21:
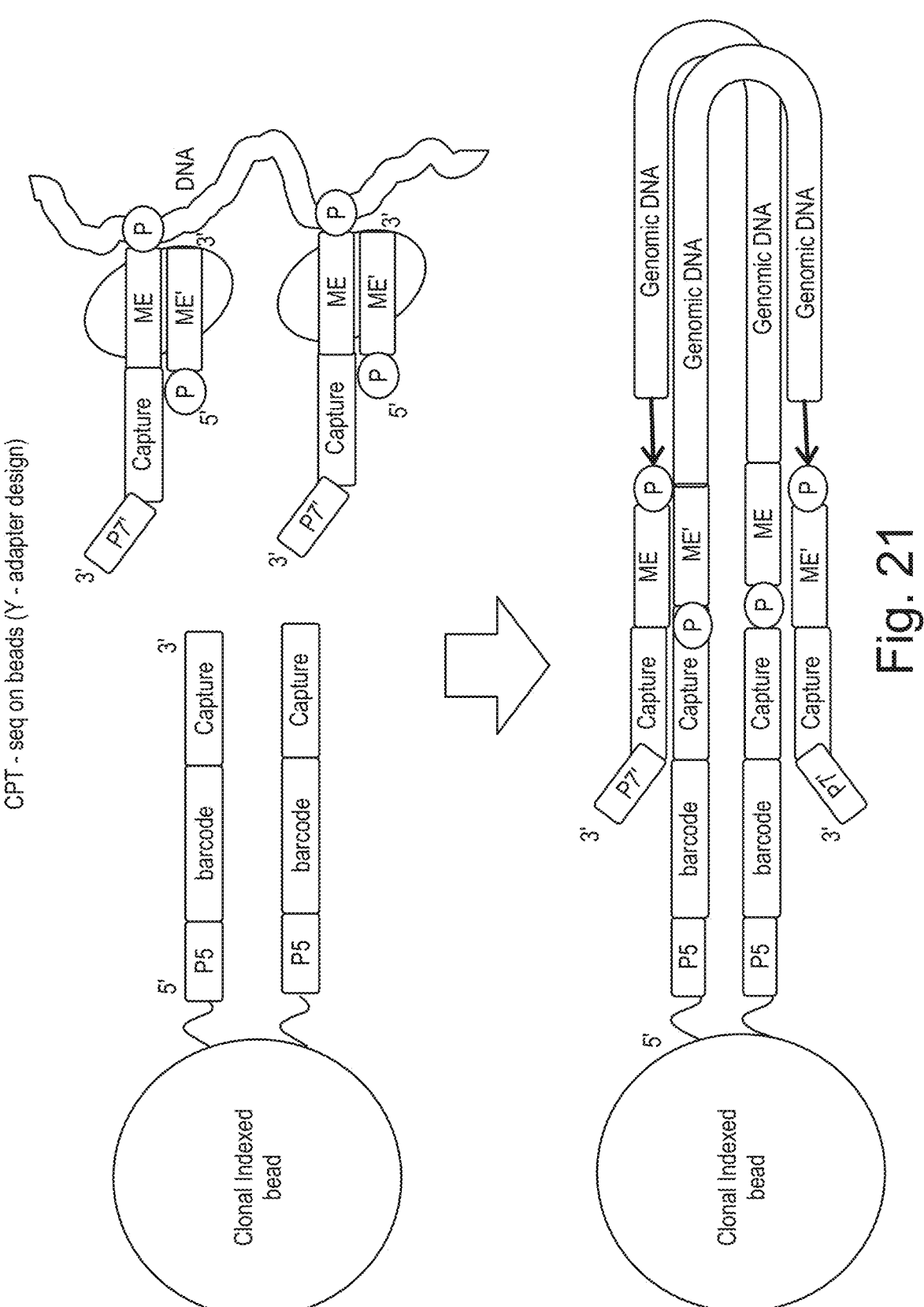
FIG. 21 shows an exemplary scheme of making such Y-adapters during the ligation of CPT-DNA to the immobilized oligonucleotides on the solid support.

In some embodiments, Y-adaptor is formed through hybridization capture of CPT-DNA with the probe/index on the solid support such as beads. FIG. 21 shows an exemplary scheme of making such Y-adapters. The use of these Y-adapters ensures that potentially every fragment can become a sequencing library. This increases the coverage per sequencing.

Figure 22:
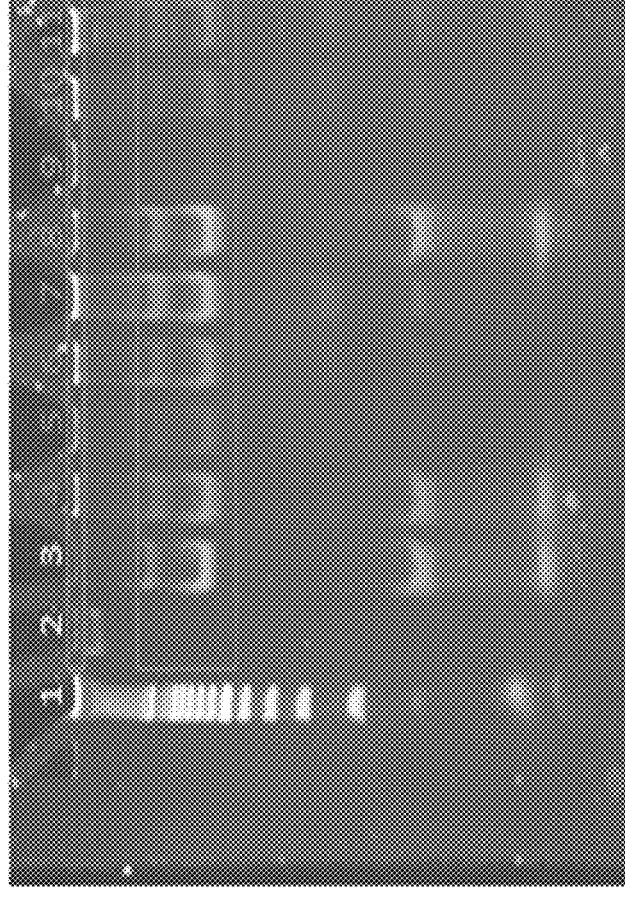
FIG. 22 depicts an agarose gel electrophoresis showing the removal of free transposome from contiguously-linked libraries by size exclusion chromatography.

In some embodiments, free transposomes may be separated from CPT-DNA. In some embodiments, the separation of the free transposomes is by size exclusion chromatography. In one embodiment, the separation may be achieved by MicroSpin S-400 HR Columns (GE Healthcare Life Sciences, Pittsburgh, PA). FIG. 22 shows an agarose gel electrophoresis of the separated of CPT-DNA from the free transposomes.

Capturing contiguously-linked, transposed, target nucleic acid onto a solid support through hybridization has several unique advantages. First, the method is based on hybridization and not transposition. Intramolecular hybridization rate>>intermolecular hybridization rate. Thus, chances of contiguously-transposed libraries on a single target DNA molecule to wrap around a uniquely indexed bead is much higher than having two or more different single target DNA molecule to wrap around a uniquely indexed bead. Second, DNA transposition and barcoding of the transposed DNA occur in two separate steps. Third, the challenges associated with active transposome assembly on beads and surface density optimization of transposons on solid-surfaces can be avoided. Fourth, self-transposition products can be removed by column purification. Fifth, as contiguously linked, transposed, DNA contains gaps, the DNA is more flexible and therefore puts less of a burden on transposition density (insert size) compared to immobilizing transposome on bead methods. Sixth, the method can be used with combinatorial barcoding schemes. Seventh, it is easy to covalently-link indexed oligos to the beads. Thus, there is less chance for index exchange. Eight, the tagmentation and subsequent PCR amplification may be multiplexed and can be performed in a single reaction compartment ("one-pot") reaction eliminating the need to carryout individual reactions for each index sequences.

In some embodiments, a plurality of unique barcodes throughout the target nucleic acid may be inserted during transposition. In some embodiments, each barcode includes a first barcode sequence and a second barcode sequence, having a fragmentation site disposed therebetween. The first barcode sequence and second barcode sequence can be identified or designated to be paired with one another. The pairing can be informative so that a first barcode is associated with a second barcode. Advantageously, the paired barcode sequences can be used to assemble sequencing data from the library of template nucleic acids. For example, identifying a first template nucleic acid comprising a first barcode sequence and a second template nucleic acid comprising a second barcode sequence that is paired with the first indicates that the first and second template nucleic acids represent sequences adjacent to one another in a sequence representation of the target nucleic acid. Such methods can be used to assemble a sequence representation of a target nucleic acid de novo, without the requirement of a reference genome.

In one aspect, the present invention relate to methods and compositions to generate shotgun sequence library of a specific DNA fragment.

Figure 23:
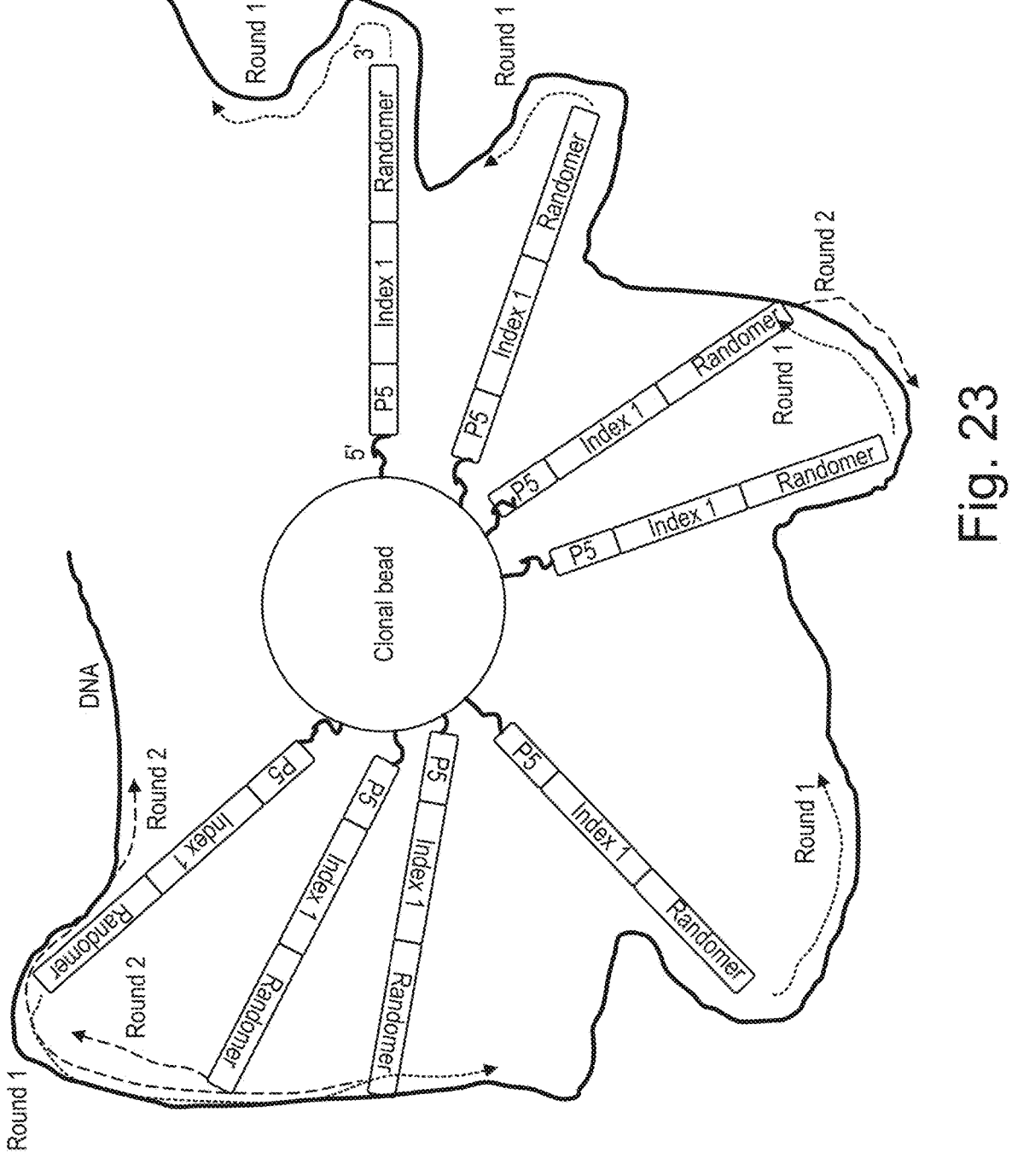
FIG. 23 shows an exemplary scheme of generating shotgun sequence library of a specific DNA fragment.
Figure 24:
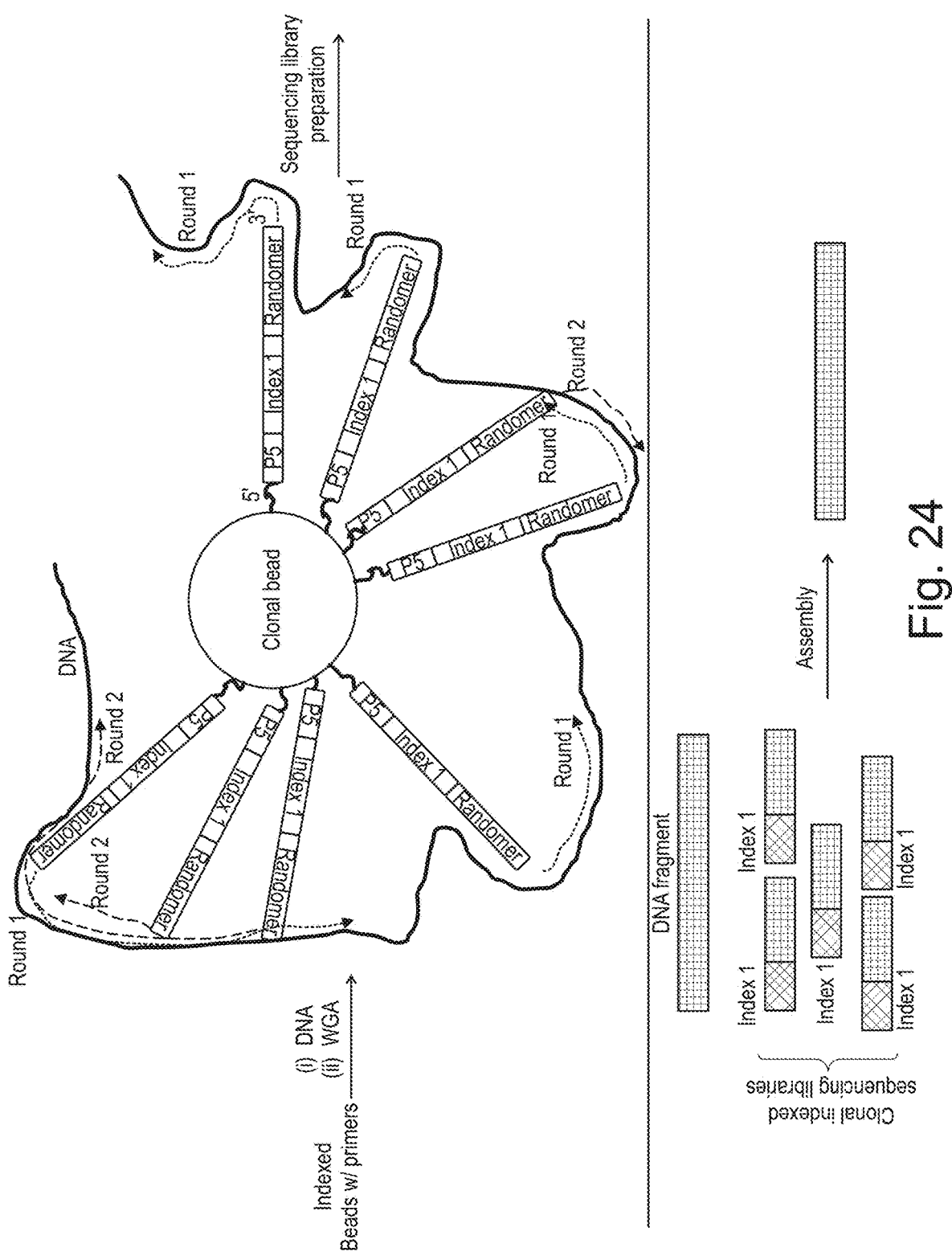
FIG. 24 shows an exemplary scheme of assembling the sequence information from clonal indexed sequencing library.

In one embodiment, clonal indexed beads are generated with immobilized oligonucleotide sequences: random or specific primer and unique indexes. Target nucleic acid is added to the clonal indexed beads. In some embodiments, the target nucleic acid is DNA. In one embodiment, the target DNA is denatured. The target DNA hybridizes with primers comprising unique indexes immobilized on the solid surface (e.g., bead) and subsequently with other primers with the same index. The primers on the bead amplify the DNA. One or more further rounds of amplification may be carried out. In one embodiment, the amplification may be carried out by whole genome amplification using bead immobilized primers with a 3' random n-mer sequence. In a preferred embodiment, the random n-mer contains pseudo-complementary bases (2-thiothymine, 2-amino dA, N4-ethyl cytosine, etc.) to prevent primer-primer interaction during amplification (Hoshika, S; Chen, F; Leal, N A; Benner, S A, Angew. Chem. Int. Ed. 49(32) 5554-5557 (2010). FIG. 23 shows an exemplary scheme of generating shotgun sequence library of a specific DNA fragment. A clonal indexed sequencing library can library of the amplified product can be generated. In one embodiment, such library can be generated by transposition. Sequence information of the clonal indexed library can be used to assemble the contiguous information using the index information as a guide. FIG. 24 shows an exemplary scheme of assembling the sequence information from clonal indexed sequencing library.

The methods of the above embodiments have several advantages. Intra-molecular amplification on a bead is much faster than inter-bead amplification. Thus, the products on a bead will have the same index. A shotgun library of a specific DNA fragment can be created. Random primers amplify the template at random locations and therefore a shotgun library with the same index can be generated from a specific molecule and the sequence information can be assembled using the indexed sequence. A significant advantage of the methods of the above embodiments is that the reactions can be multiplexed in a single reaction (one pot reaction) and will not require using many individual wells. Many index clonal beads can be prepared so many different fragments can be uniquely labeled, and discrimination can be made to the parental alleles for same genomic regions. With a high number of indexes, the chance that the DNA copy of the father and copy of the mother will receive the same index for the same genomic region is low. The method takes advantage of the fact that intra reactions are much faster than inter, the beads basically generate a virtual partition in a larger physical compartment.

In some embodiments of all of the above aspect of the inventions, the method may be used for cell free DNA (cfDNA) in cfDNA assays. In some embodiments, the cfDNA is obtained from plasma, placental fluids.

In one embodiment, the plasma can be obtained from undiluted whole blood using membrane based, sedimenta-tion assisted plasma separator (Liu et al. Anal Chem. 2013 Nov. 5; 85(21):10463-70). In one embodiment, the collection zone of the plasma of the plasma separator may comprise solid support comprising transposomes. The solid support comprising transposomes may capture the cfDNA from the isolated plasma as it is separated from the whole blood and can concentrate the cfDNA and/or tagment the DNA. In some embodiments, the tagmentation will further introduce unique barcodes to allow subsequent demultiplexing after sequencing of the pool of libraries.

In some embodiments, the collection zone of the separator may comprise PCR master mix (primers, nucleotides, buffers, metals) and polymerase. In one embodiment, the master mix can be in dry form such that it will be reconstituted as the plasma comes out of the separator. In some embodiments the primers are random primers. In some embodiments, the primers can be specific primers for a particular gene. PCR amplification of the cfDNA will result in the generation of library directly from the separated plasma.

In some embodiments, the collection zone of the separator may comprise RT-PCR master mix (primers, nucleotides, buffers, metals), reverse transcriptase and polymerase. In some embodiments the primers are random primers or oligo dT primers. In some embodiments, the primers can be specific primers for a particular gene. The resulting cDNA can be used for sequencing. Alternatively, the cDNA can be treated with transposomes immobilized on a solid support for sequence library preparation.

In some embodiments, the plasma separator may comprise barcodes (1D or 2D barcodes). In some embodiments, the separation device may comprise blood collection device. This would result in direct delivery of the blood to the plasma separator and library prep device. In some embodiments, the device may comprise a downstream sequence analyzer. In some embodiments, sequence analyzer is a single use sequencer. In some embodiments, the sequencer is capable of queuing samples before sequencing in a batch. Alternatively, the sequencer may have random access capability, where samples are delivered to their sequencing area.

In some embodiments, the collection zone for plasma may comprise silica substrates, such that the cell free DNA is concentrated.

Simultaneous Phasing and Methylation Detection

The 5-methyl Cytosine (5-Me-C) and 5-hydroxymethyl Cytosine (5-hydroxy-C), also known as epi modifications play an important role in cellular metabolism, differentiation and cancer development. Inventors of the present application has surprisingly and unexpectedly found that phasing and simultaneous methylation detection is possible using the methods and compositions of the present application. The present methods will allow to combine CPT-seq on beads (indexed contiguity linked libraries) with DNA methylation detection. For example, individual libraries generated on beads can be treated with bisulfite, converting non-methylated Cs, but not methylated Cs to Us, allowing the detection of 5-Me-C. Through additional phasing analysis using heterozygous SNPs, epi-medication-phasing blocks can be established multi megabase range.

In some embodiments, the size of the DNA analyzed can be about hundred bases to about multi mega bases. In some embodiments, the size of the DNA analyzed can be about 100, 200, 300, 400, 500, 600, 700, 800, 900, 1000, 1200, 1300, 1500, 2000, 3000, 3500, 4000, 4500, 5000, 5500, 6000, 6500, 7000, 7,500, 8000, 8500, 9000, 9500, 10,000, 10,500, 11,000, 11,500, 12,000, 12500, 13000, 14000, 14500, 15000, 15500, 16000, 16500, 17000, 17,500, 18,000, 18,500, 19,000, 19,500, 20,000, 20,500, 21,000, 21,500, 22,000, 22,500, 23,000, 23,500, 24,000, 24,500, 25,000, 25,500, 26,000, 26,500, 27,000, 27,500, 28,000, 28,500, 29,500, 30,000, 30,500, 31,000, 31,500, 32,000, 33,000, 34,000, 35,000, 36,000, 37,000, 38,000, 39,000, 40,000, 42,000, 45,000, 50,000, 55,000, 60,000, 65,000, 70,000, 75,000, 80,000, 85,000, 90,000, 95,000, 100,000, 110,000, 120,000, 130,000, 140,000, 150,000, 160,000, 170,000, 180, 000, 200,000, 225,000, 250,000, 300,000, 350,000, 400,000, 450,000, 500,000, 550,000, 600,000, 650,000, 700,000, 750, 000, 800,000, 850,000, 900,000, 1,000,000, 1,250,000, 1,500,000, 2,000,000, 2,500,000, 3,000,000, 4,000,000, 5,000,000, 6,000,000, 7,000,000, 8,000,000, 9,000,000, 10,000,000, 15,000,000, 20,000,000, 30,000,000, 40,000, 000, 50,000,000, 75,000,000, 100,000,000 or more bases.

Other epi-modifications like 5-hydroxy-C, DNA oxidation products, DNA alkylation products, histone-foot printing etc. can also be analyzed in the context of phasing using the disclosed methods and compositions of the present application.

In some embodiments, DNA is first transformed into indexed-linked libraries on a solid-support. Individual indexed libraries, much smaller than the original DNA, are less prone to fragmentation since the individual libraries are smaller. Even if a small fraction of indexed libraries are lost, phasing information is still maintained across the long span of the indexed DNA molecule. For example, if a 100 kb molecule in traditional bisulfite conversion (BSC) is fragmented in half the contiguity is now restricted to 50 kb. In the methods disclosed herein, a 100 kb library is first indexed and even if a fraction of individual libraries are lost, contiguity is still at ~100 kb (except in the unlikely event when all libraries lost are from one end of the DNA molecule. Also, methods disclosed in the present application has an additional advantage because no additional purification steps are required in contrast to those required in traditional bisulfite conversion approaches, thereby improving the yield. In the methods of the present application, the beads are simply washed after bisulfite conversion. Additionally, while DNA is bound to a solid phase, buffer exchanges can be readily performed with minimal loss of DNA (indexed libraries) and reduced hands on time.

Figure 43:
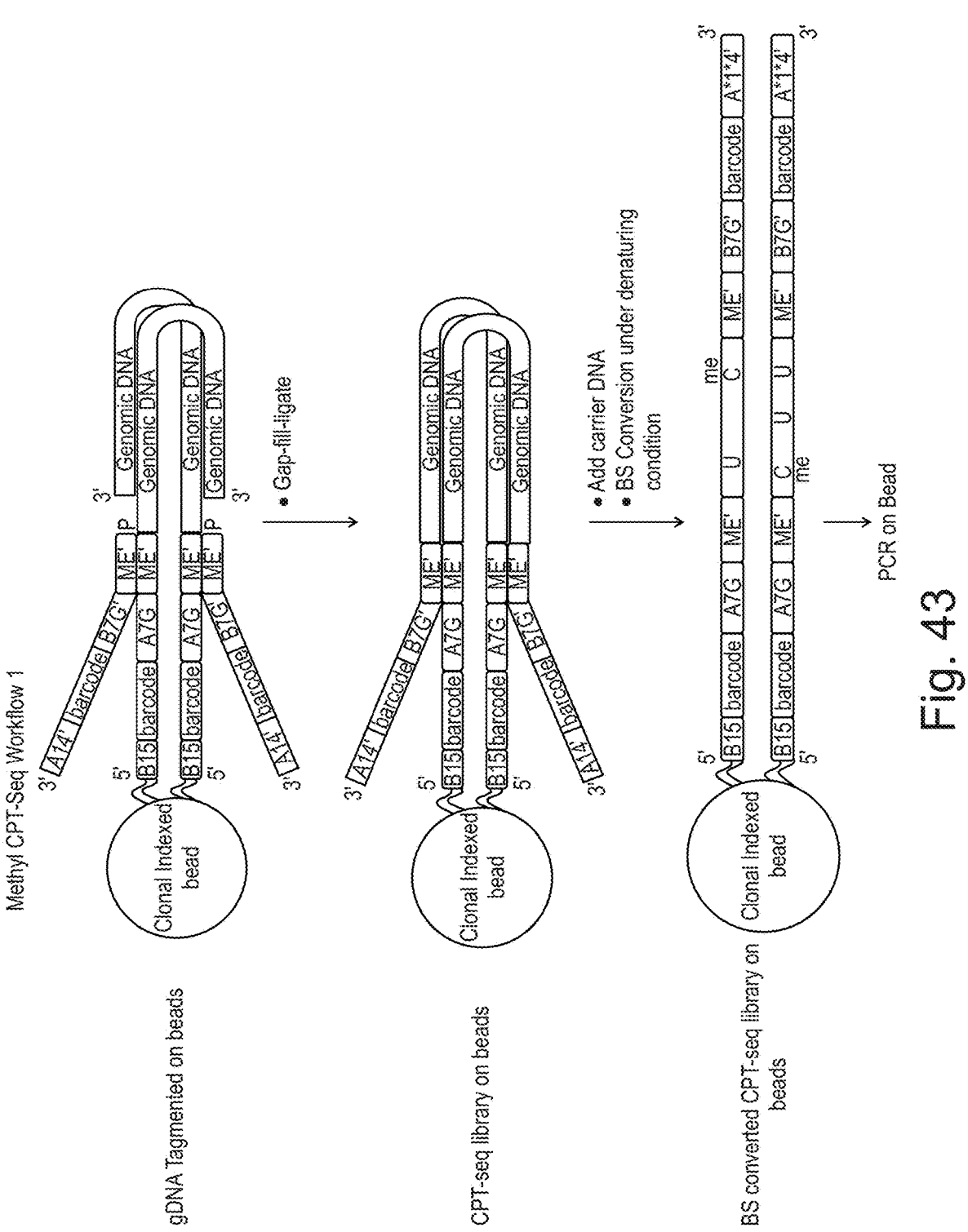
FIG. 43 shows an exemplary scheme of simultaneous phasing and methylation detection.

Exemplary scheme of simultaneous phasing and methylation detection is shown in FIG. 43. The workflow consists of tagmentation of DNA on beads, gap-fill-ligate the 9-bp repeat regions, removal of Tn5 with SDS, and bisulfite conversion of the individual libraries on the beads. The bisulfite conversion is performed under denaturing conditions to ensure that neighboring complementary libraries are not re-annealing, therefore reducing the bisulfite conversion efficiency. BCS converts non-methylated C's to U's and methylated C's are not converted.

FIG. 44 shows an alternative exemplary scheme of simultaneous phasing and methylation detection. After preparing sequencing libraries after transposition, a fraction of gap-filled-ligated libraries are degraded in order to prepare single-stranded templates. Single-stranded templates need milder conditions for bisulfite conversion since the templates are already single-stranded which could reduce library loss or improve bisulfite conversion efficiency. In one embodiment, a mixture of 3' thio-protected transposons (Exo resistant) and non-protected transposons are used on the same bead. Enzymes, for example, Exo I, can be used to digest the non-thio-protected libraries, converting them to single stranded libraries. Using a mixture of 50:50 of thio-protected transposons: non-protected transposons, 50% of the libraries will be converted to single-stranded libraries (50% have one transposon of the library is protected and one, the complement strand, is not protected), 25% will not be converted (both transposons are thio protected), and 25% are both converted removing the whole library (both transposons not protected).

One challenge to performing bisulfite conversion of DNA bound to a solid phase, such as streptavidin magnetic beads is that extended treatment of bead bound DNA with sodium bisulfite at high temperatures damages both the DNA and the beads. To help ameliorate DNA damage, carrier DNA (i.e. Lambda DNA) is added to the reaction mixture prior to bisulfite treatment. Even in presence of carrier DNA, it has been estimated that approximately 80% of starting DNA is lost. As a result, CPTSeq contiguity blocks have fewer members than those in the traditional CPTSeq protocol.

Therefore, several strategies are proposed herein to improve DNA yield of the Epi-CPTSeq protocol. The first strategy relies on decreasing library insert size by more densely populating transposome complexes to the streptavidin beads. By decreasing library size, a smaller proportion of library elements are degraded by bisulfite treatment.

Figures 68A, 68B, 68C:
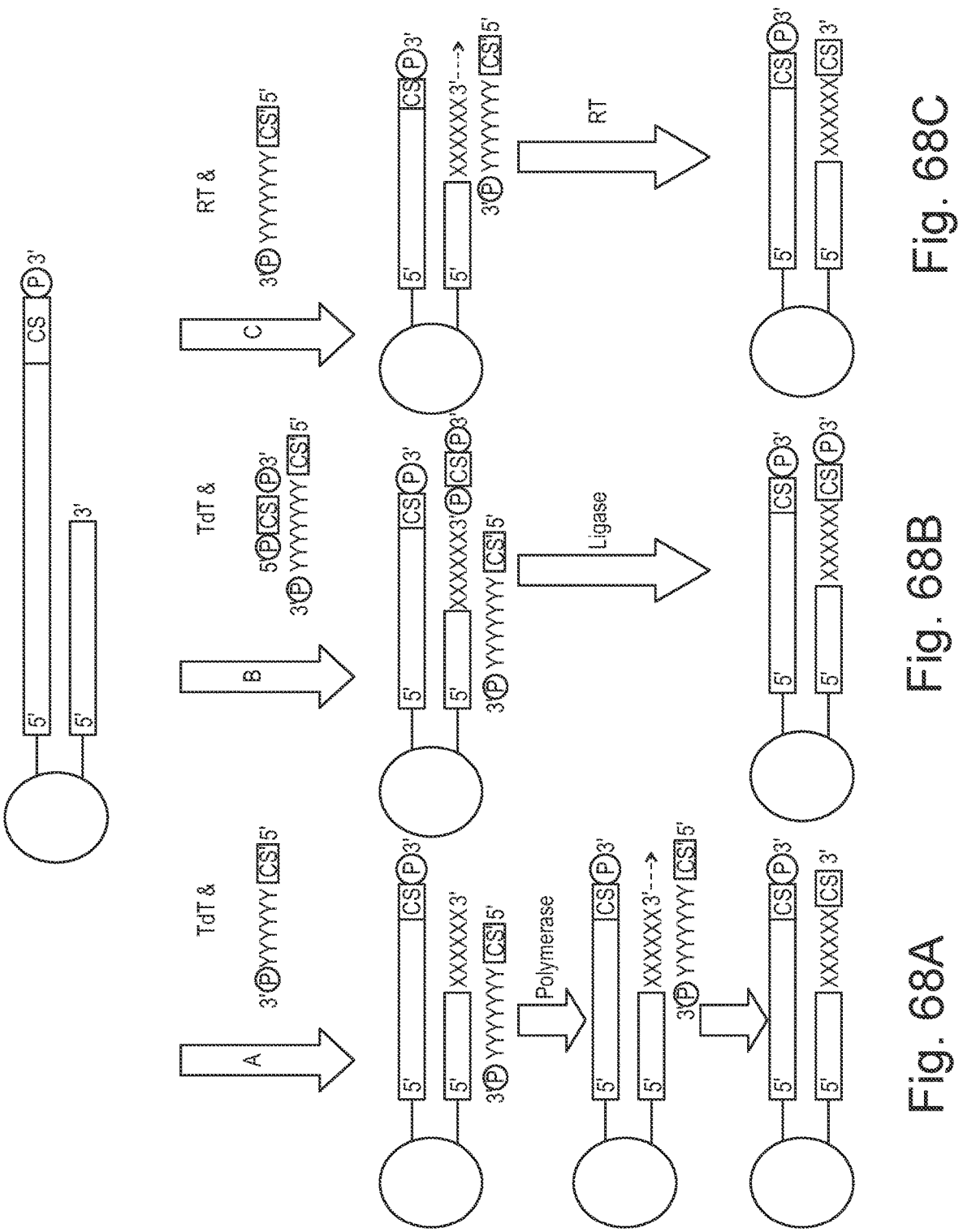
FIG. 68A is a schematic illustration of an example of a method to improve DNA yield of the Epi-CPTSeq protocol using an enzymatic method (polymerase) for recovery of broken library elements after bisulfite treatment.
FIG. 68B is a schematic illustration of an example of a method to improve DNA yield of the Epi-CPTSeq protocol using an enzymatic method (ligase) for recovery of broken library elements after bisulfite treatment.
FIG. 68C is a schematic illustration of an example of a method to improve DNA yield of the Epi-CPTSeq protocol using an enzymatic method (reverse transcriptase, RT) for recovery of broken library elements after bisulfite treatment.

The second strategy to improve DNA yield of the Epi-CPTSeq protocol is enzymatic recovery of broken library elements. The purpose of the recovery strategy is to add the 3' common sequence necessary for library amplification back to the bead bound library elements that became digested and lost their 3' portion during bisulfate treatment. After the addition of the 3' common sequence these elements can now be PCR amplified and sequenced. FIG. 67 and FIGS. 68A to 68C show an exemplary scheme of this strategy. Double stranded CPTSeq library elements have been denatured and bisulfite converted (top panel). During bisulfite conversion, one of DNA strands has been damaged (middle panel), leading to loss of the PCR common sequence on the 3' end. Template rescue strategies restore the 3' common sequence (green) necessary for PCR amplification (bottom panel). In one example, a terminal transferase in a presence of 3' phosphorylated attenuator oligo, a sequence containing a sequencing adapter followed by an oligo dT stretch is used (FIG. 68A). Briefly, TdT adds a stretch of 10 to 15 dAs to the 3' end of a broken library element, which anneals to the oligo dT portion of the attenuator oligo. Formation of this DNA hybrid stops TdT reaction and provides template for consequent extension of the 3' end of a broken library element by DNA polymerase.

In an alternative workflow (FIG. 68B), the TdT tailing reaction is performed in the presence of a partially double stranded attenuator oligo, containing a single stranded oligo dT portion and 5' phosphorylated double stranded sequencing adapter portion. Upon termination of TdT reaction, the nick between last added dA and 5' phosphorylated attenuator oligo is sealed by DNA ligase.

Both of the described workflows rely on a controllable TdT tailing reaction recently developed and described in US Patent Application Publication 20150087027. A common sequencing adapter can also be added to the 3' end of broken library elements by a recently introduced ssDNA template switching activity of MMLV RT. In short, MMLV RT and a template switch oligo (TS oligo) are added to damaged DNA (FIG. 68C). In first step of this reaction, reverse transcriptase adds a few additional nucleotides to 3' ends of a single-stranded DNA fragment, and these bases pair with an oligo (N) sequence presented at the 3' end of one of the TS oligos. Then, reverse transcriptase template switching activity adds the sequences of the annealed common primers to the 3' end of BSC broken library element, restoring its ability to get amplified in PCR with common sequencing primers.

Figure 69:
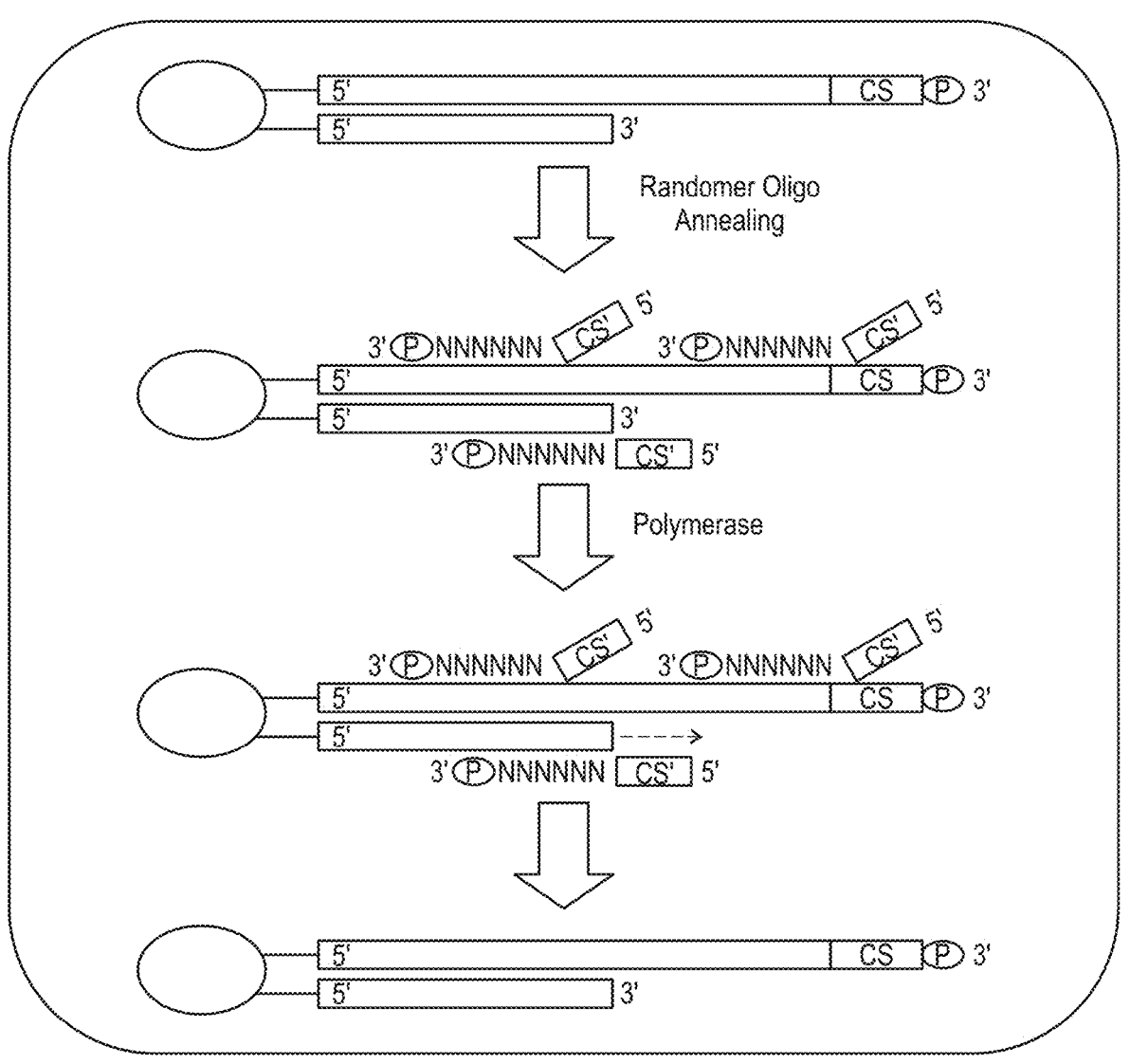
FIG. 69 shows an exemplary scheme for template rescue using random primer extension.

As a part of the third strategy, an Epicentre's EpiGenome kit "post-bisulfite conversion" library construction method can be used to rescue library elements which lost their common sequences at the 3' end during bisulfite conversion. As shown in FIG. 69, this library rescue method utilizes 3' phosphorylated oligos with common sequences followed by a short stretch of random sequence. These short random sequences hybridize to the bisulfite-treated single-stranded DNA and common sequences are subsequently copied to the broken library strand by DNA polymerase.

Figure 74:
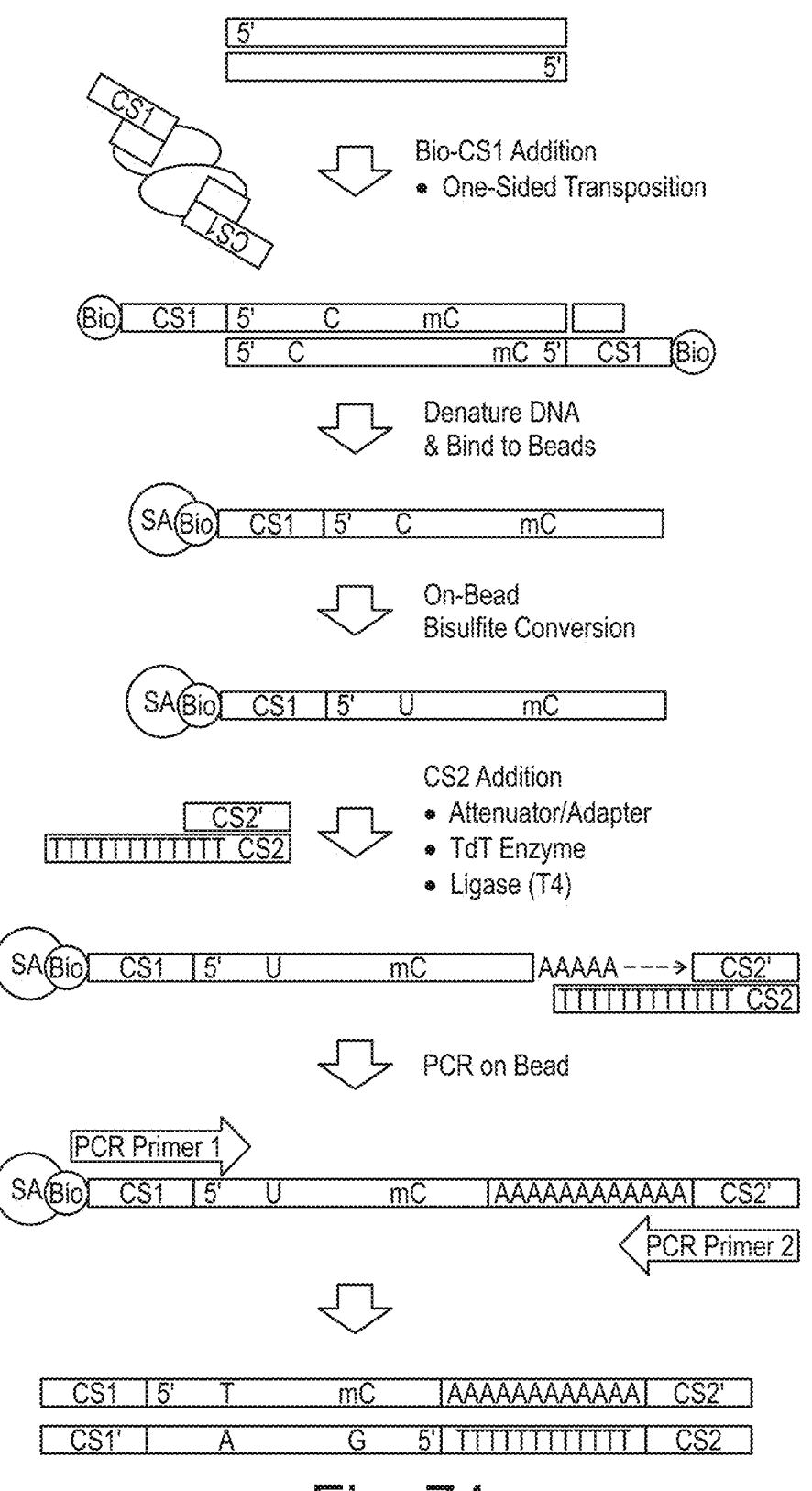
FIG. 74 shows an exemplary scheme of bead based bisulfite conversion of DNA (SEQ ID NOS 7, 7, 9, 9, and 7, respectively, in order of appearance).

FIG. 74 shows the fourth strategy to improve the bisulfite sequencing methods on beads. A first common sequence comprising a capture tag is covalently attached to the 5' ends of DNA. The first common sequence can be attached to DNA using various methods, including single-sided trans-position (as pictured), adapter ligation, or terminal transfer-ase (TdT) adapter ligation as described in US Patent Application Publication 20150087027.

Next, DNA is denatured (e.g. incubation at high heat) and bound to a solid support. If biotin is used as a capture tag on CS1, for example, DNA can be bound using streptavidin magnetic beads (as pictured). Once bound to the solid support buffer exchanges can be readily made.

In the next step, bisulfite conversion of ssDNA is performed (see FIG. 75A). In the single stranded form, DNA should be readily accessible for bisulfite conversion; up to 95% conversion efficiencies have been observed using a modified version of Promega's Methyl Edge BSC kit (see FIG. 75B). FIG. 75A shows a chart of various conditions for bisulfite conversion (BSC) and the sequences of uncon-verted mosaic ends (ME) and BSC ME (SEQ ID NOS 5 and 6, respectively, in order of appearance). FIG. 75B shows the results of bisulfite conversion efficiency optimization in an image of a gel and in a bar graph that shows varied bisulfite conversion efficiency under different conditions.

After bisulfite conversion, a second common sequence is covalently attached to the 3' end of ssDNA attached to solid support. Several methods have been described above to covalently attach oligos to ssDNA. Using the TdT attenua-tor/adapter ligation method, ligation efficiencies of >95% have been achieved. As a result, final library yields using the proposed MethylSeq workflow should be greater than exist-ing methods.

In the final step, PCR is performed to amplify the library and remove it from the solid support. PCR primers can be designed to add additional commons sequences, such as sequencing adapters, to the ends of the MethylSeq library.
Preparation of Different Size Libraries in a Single Assay The accuracy of the assembly of genomes is contingent on the use of different length scale technologies. For example, shotgun (100's of bp)-matepair (~3 Kb) to –Hi-C (Mb-scale) are all methods that sequentially improve assemblies and contig lengths. The challenge is that multiple assays are required to accomplish this, making the multi-layered approach cumbersome and costly. The compositions and methods disclosed herein can address multiple length scales in a single assay.

Figure 45:
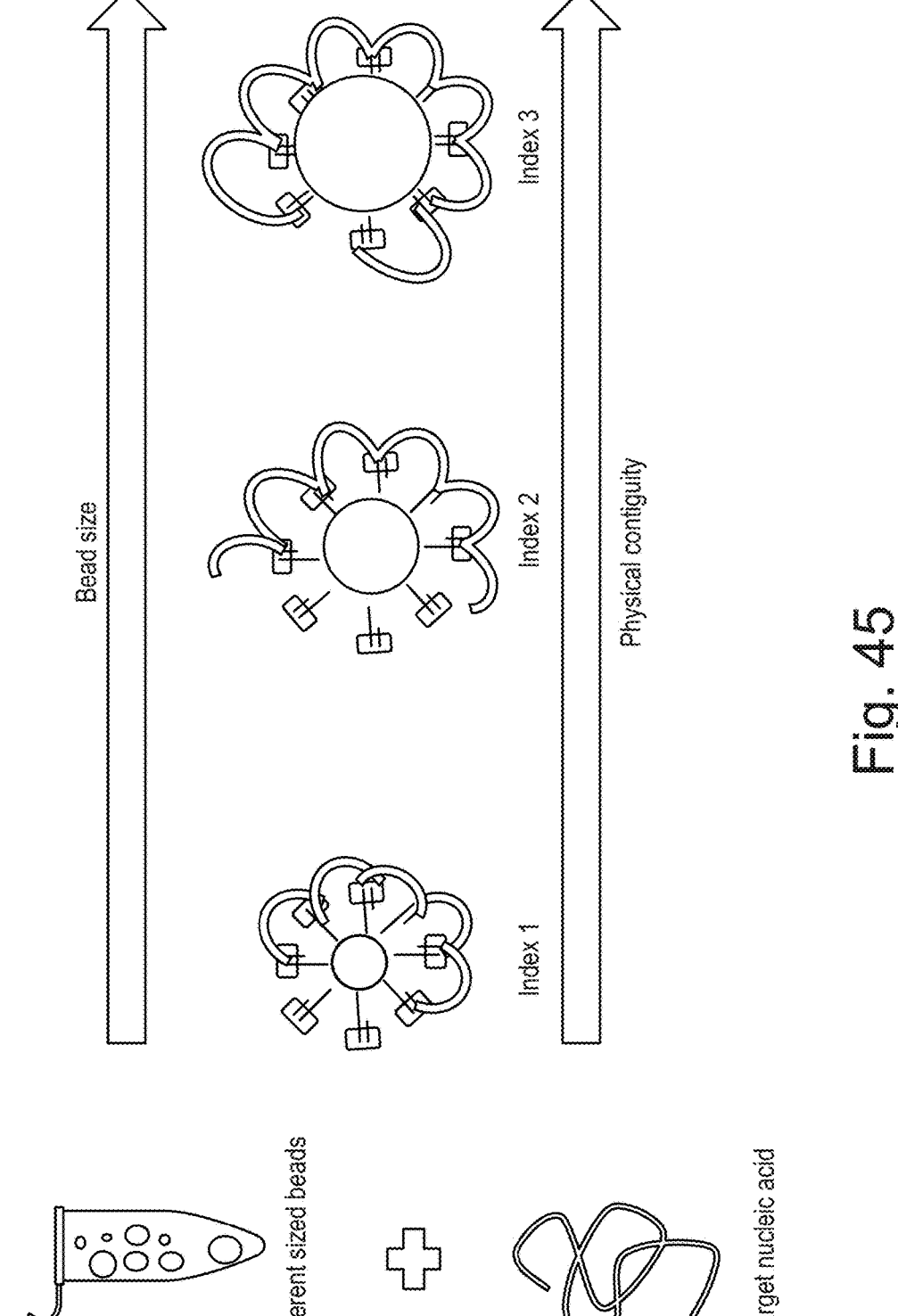
FIG. 45 shows an exemplary scheme to generate various sized libraries using various sized clonally indexed beads in a single assay.

In some embodiments, library preparation can be achieved in a single assay using differentially sized solid support, for example, beads. Each bead size will generate a specific library size or range of sizes, with the physical size of the bead determining the library size. The various sized beads all have unique clonal indices that are transferred to the library. As such, different sizes libraries are generated with each different library scale-length uniquely indexed. The various length-scale libraries are prepared simultaneously in the same physical compartment, reducing cost and improving overall work flow. In some embodiments, each specific solid support size, for example, bead size receives a unique index. In some other embodiments, multiple different indexes of the same solid support size, for example, bead size are also prepared so multiple DNA molecules can be index partitioned for that size range. FIG. 45 shows an exemplary scheme to generate various sized libraries using various sized clonally indexed beads in a single assay.

In some embodiments, the size of the libraries generated are about 50, 75, 100, 150, 200, 250, 300, 350, 400, 500, 600, 700, 800, 900, 1000, 1200, 1300, 1500, 2000, 3000, 3500, 4000, 4500, 5000, 5500, 6000, 6500, 7000, 7,500, 8000, 8500, 9000, 9500, 10,000, 10,500, 11,000, 11,500, 12,000, 12500, 13000, 14000, 14500, 15000, 15500, 16000, 16500, 17000, 17,500, 18,000, 18,500, 19,000, 19,500, 20,000, 20,500, 21,000, 21,500, 22,000, 22,500, 23,000, 23,500, 24,000, 24,500, 25,000, 25,500, 26,000, 26,500, 27,000, 27,500, 28,000, 28,500, 29,500, 30,000, 30,500, 31,000, 31,500, 32,000, 33,000, 34,000, 35,000, 36,000, 37,000, 38,000, 39,000, 40,000, 42,000, 45,000, 50,000, 55,000, 60,000, 65,000, 70,000, 75,000, 80,000, 85,000, 90,000, 95,000, 100,000, 110,000, 120,000, 130,000, 140, 000, 150,000, 160,000, 170,000, 180,000, 200,000, 225,000, 250,000, 300,000, 350,000, 400,000, 450,000, 500,000, 550, 000, 600,000, 650,000, 700,000, 750,000, 800,000, 850,000, 900,000, 1,000,000, 1,250,000, 1,500,000, 2,000,000, 2,500, 000, 3,000,000, 4,000,000, 5,000,000, 6,000,000, 7,000,000, 8,000,000, 9,000,000, 10,000,000, 15,000,000, 20,000,000, 30,000,000, 40,000,000, 50,000,000, 75,000,000, 100,000, 000 or more bases.

Figure 46:
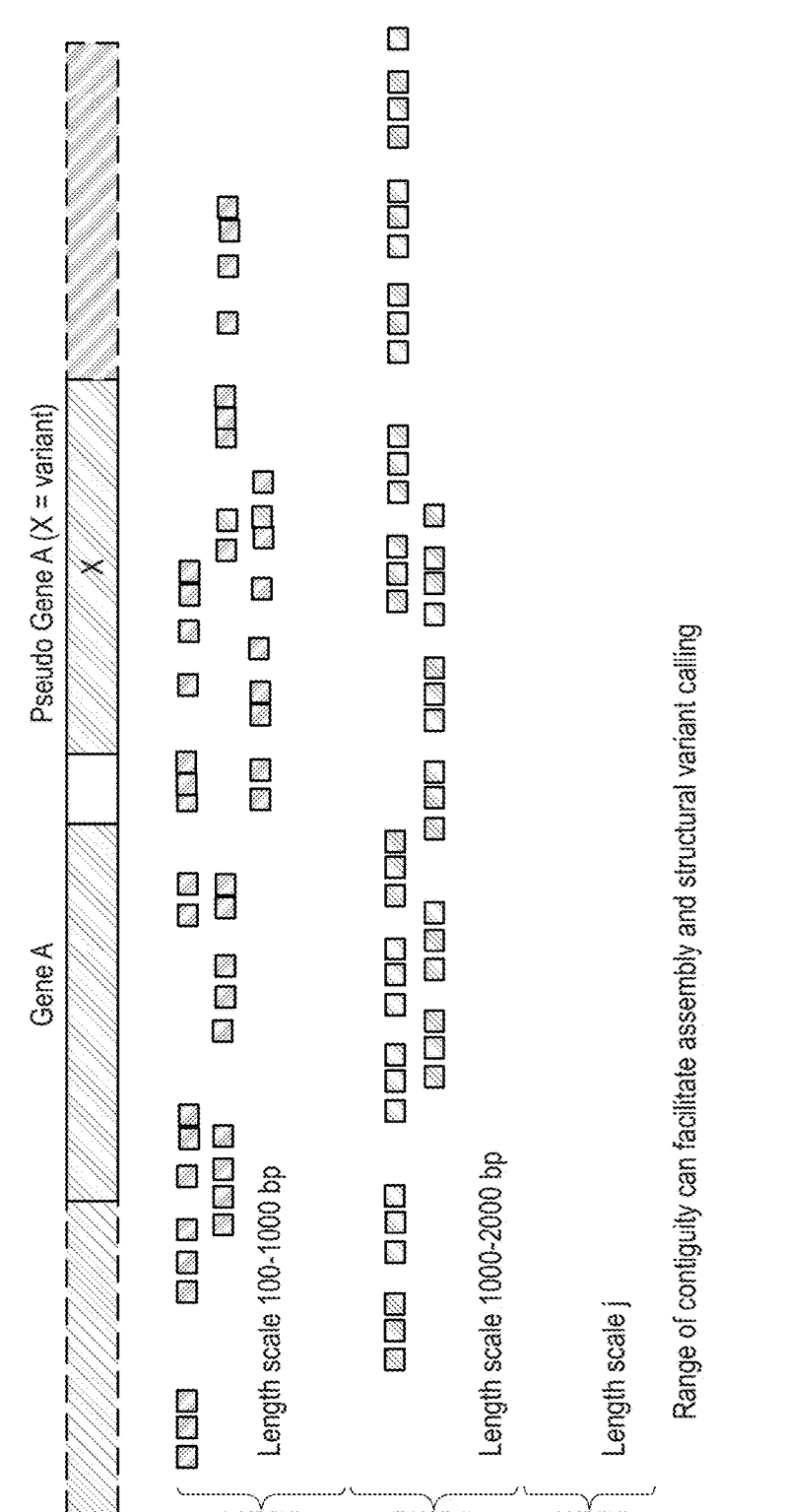
FIG. 46 shows an exemplary scheme of determining genetic variants with different length scale libraries.

In some embodiments, multiple length scale libraries discussed above can be used in the assembly of pseudo-genes, paralogs etc. instead of having one large length scale. In some embodiments, multiple length scale libraries are prepared simultaneously in a single assay. The advantage is that at least one length-scale will link a unique region with only the pseudo-gene and or gene, but not both. As such, variants detected with this length-scale can uniquely assign the variant to either the gene or the pseudo-gene. The same holds true for copy number variants, paralogs etc. The strength of assembly is the use of different length scales. Using the methods disclosed herein different length scale indexed linked libraries can be generated in a single assay instead of individual, different library preparations for dif-ferent length scales. FIG. 46 shows an exemplary scheme of determining genetic variants with different length scale libraries.

Analysis of Genomic Variants

The compositions and methods disclosed herein relate to analysis of genomic variants. Exemplary genomic variants include but are not limited to deletions, inter chromosomal translocations, duplications, paralogs, interchromosomal gene fusions. In some embodiments, the compositions and methods disclosed herein relate to determining phasing information of the genomic variants. The table below shows exemplary interchromosomal gene fusions.

TABLE 1

Interchromosomal Gene Fusions

| BP1 Chr | BP1 Start | BP1 End | Length | BP2 Chr | BP2 Start | BP2 End | Length | Supp. | CPT Detectable |
|---|---|---|---|---|---|---|---|---|---|
| chr2 | 3930448 | 3935237 | 4789 | chr12 | 124494444 | 124500974 | 6,530 | 100 | Yes |
| chr2 | 11948918 | 11954246 | 5328 | chr21 | 18143482 | 18149316 | 5,834 | 104 | Yes |
| chr3 | 73158440 | 73162742 | 4302 | chr17 | 41379324 | 41384937 | 5,613 | 80 | Yes |
| chr3 | 73158440 | 73162742 | 4302 | chr17 | 41397704 | 41403894 | 6,190 | 132 | Yes |
| chr3 | 75985574 | 75999286 | 13712 | chr20 | 2619877 | 26213907 | 15,230 | 271 | Yes |
| chr3 | 97545352 | 97548214 | 2862 | chr20 | 51820873 | 51826137 | 5,264 | 54 | No |
| chr3 | 111271573 | 111275045 | 3472 | chr8 | 128529232 | 128538779 | 9,547 | 138 | Yes |
| chr5 | 45603558 | 45620710 | 17152 | chr22 | 39709007 | 39715736 | 6,729 | 64 | No |
| chr7 | 81789161 | 81794473 | 5312 | chr10 | 60900343 | 60904922 | 4,579 | 66 | Yes |
| chr7 | 100936524 | 100940377 | 3853 | chr11 | 114417947 | 114425186 | 7,239 | 45 | Yes |
| chr7 | 111050826 | 111056166 | 5340 | chr12 | 108199590 | 108203183 | 3,593 | 55 | Yes |
| chr8 | 28431852 | 28436443 | 4591 | chr17 | 79758758 | 79762966 | 4,208 | 51 | No |
| chr9 | 12624450 | 12627475 | 3025 | chr22 | 29065133 | 29067995 | 2,862 | 11 | Yes |
| chr9 | 96381359 | 96386424 | 5065 | chr13 | 19645775 | 19650874 | 5,099 | 29 | Yes |
| chr9 | 101473886 | 101479887 | 6001 | chr22 | 32575696 | 32579748 | 4,052 | 67 | Yes |
| chr9 | 109772276 | 109777707 | 5431 | chr20 | 29873930 | 29878940 | 5,010 | 70 | Yes |
| chr9 | 121298728 | 121305690 | 6962 | chr11 | 11980608 | 12002075 | 21,467 | 178 | Yes |
| chr12 | 56987510 | 56991801 | 4291 | chr15 | 39995972 | 39999958 | 3,986 | 25 | Yes |
| chr13 | 55877158 | 55882393 | 5235 | chr19 | 12896441 | 12904258 | 7,817 | 72 | Yes |
| chr13 | 63618669 | 63624153 | 5484 | chr17 | 21666588 | 21670266 | 1,678 | 115 | Yes |

25

Table 2 shows exemplary deletions in chromosome 1:

TABLE 2

Exemplary Deletions in Chromosome 1

| Chr | BP1 Start | BP1 End | | BP2 Start | BP2 End | | Size (bp) | CPT Signal |
|---|---|---|---|---|---|---|---|---|
| chr1 | 1219982 | 1223434 | 3452 | 1225577 | 1229105 | 3528 | 2143 | Yes |
| chr1 | 95911985 | 9595341 | 3356 | 9597227 | 9600089 | 2862 | 1886 | Yes |
| chr1 | 14432636 | 14436290 | 3654 | 14437570 | 14441375 | 3805 | 1280 | Yes |
| chr1 | 25154228 | 25158576 | 4448 | 25161514 | 25165093 | 3579 | 2838 | Yes |
| chr1 | 26456898 | 26459838 | 2940 | 26463789 | 26468542 | 4753 | 3951 | Yes |
| chr1 | 34985513 | 34991181 | 5668 | 34992539 | 34995862 | 4323 | 1358 | Yes |
| chr1 | 56827433 | 55831099 | 3566 | 55834909 | 55838758 | 3849 | 3810 | No |
| chr1 | 63702441 | 63705334 | 2893 | 63708226 | 63712091 | 3865 | 2892 | ?? |
| chr1 | 71234176 | 71237339 | 3163 | 71239506 | 71243649 | 4143 | 2167 | Yes |
| chr1 | 73450444 | 73454045 | 3601 | 73454999 | 73458655 | 3656 | 954 | ?? |
| chr1 | 81400468 | 81404472 | 4004 | 81408850 | 81413863 | 5013 | 4378 | Yes |
| chr1 | 83465559 | 83469370 | 3811 | 83477194 | 83482174 | 4980 | 7824 | Yes |
| chr1 | 84513313 | 84517907 | 4594 | 84524680 | 84528485 | 3805 | 6773 | Yes |
| chr1 | 84708940 | 84711986 | 3045 | 84715625 | 84719559 | 3934 | 3639 | Yes |
| chr1 | 97657769 | 97660911 | 3142 | 97669287 | 97672164 | 2877 | 8376 | No |
| chr1 | 1.05E+08 | 1.06E+08 | 4804 | 1.06E+03 | 1.06E+08 | 3723 | 6370 | Yes |
| chr1 | 1.07E+08 | 1.07E+08 | 5095 | 1.07E+08 | 1.07E+08 | 6141 | 887 | ?? |
| chr1 | 1.09E+08 | 1.09E+08 | 2999 | 1.09E+08 | 1.09E+08 | 4018 | 3899 | Yes |
| chr1 | 1.1E+08 | 1.1E+08 | 5069 | 1.1E+08 | 1.1E+08 | 4470 | 2801 | ?? |
| chr1 | 1.13E+08 | 1.13E+08 | 5237 | 1.13E+08 | 1.13E+08 | 4626 | 3241 | Yes |
| chr1 | 1.16E+08 | 1.16E+03 | 4594 | 1.16E+08 | 1.16E+08 | 4531 | 3084 | ?? |
| chr1 | 1.45E+03 | 1.45E+08 | 5595 | 1.45E+08 | 1.45E+08 | 4721 | 3724 | Yes |
| chr1 | 1.59E+08 | 1.59E+08 | 4541 | 1.59E+08 | 1.59E+08 | 3981 | 1856 | Yes (double deletion) |
| chr1 | 1.79E+08 | 1.79E+08 | 4565 | 1.79E+08 | 1.79E+08 | 5191 | 2238 | Yes |
| chr1 | 1.79E+08 | 1.79E+08 | 4480 | 1.79E+08 | 1.79E+08 | 3917 | 2479 | Yes |
| chr1 | 1.85E+08 | 1.85E+08 | 4475 | 1.85E+08 | 1.85E+08 | 3316 | 6243 | Yes |
| chr1 | 1.97E+08 | 1.98E+08 | 4323 | 1.98E+08 | 1.98E+08 | 3694 | 2522 | No |
| chr1 | 2.06E+08 | 2.06E+08 | 4995 | 2.06E+08 | 2.06E+08 | 5216 | 3458 | Yes |
| chr1 | 2.08E+08 | 2.08E+08 | 3589 | 2.08E+08 | 2.08E+08 | 4964 | 2954 | Yes |
| chr1 | 2.1E+08 | 2.1E+08 | 2973 | 2.1E+08 | 2.1E+08 | 2943 | 7603 | Yes (double deletion) |
| chr1 | 2.3E+08 | 2.3E+08 | 3828 | 2.3E+08 | 2.3E+08 | 3079 | 8440 | Yes |
| chr1 | 2.32E+08 | 2.32E+08 | 3531 | 2.32E+08 | 2.32E+08 | 3758 | 1699 | ?? |
| chr1 | 2.38E+08 | 2.38E+08 | 3848 | 2.38E+08 | 2.38E+08 | 3920 | 2112 | Yes |
| chr1 | 2.48E+08 | 2.48E+08 | 3407 | 2.48E+08 | 2.48E+08 | 3873 | 6003 | Yes |

In some embodiments, target nucleic acid can be fragmented prior to exposing it to transposomes. Exemplary fragmentation methods include, but are not limited to sonication, mechanical shearing, and restriction digestion. Fragmentation of target nucleic acid prior to tagmentation (fragmentation and tagging) is advantageous for assembly/phasing of pseudogenes (e.g., CYP2D6). Long islands (>30 kb) of indexed linked reads will span the pseudogenes A and A' as shown in FIG. 64. Due to high sequence homology, it will be challenging to determine which variant belongs to Gene A and Gene A'. Shorter variants will link one variant of the pseudogenes with unique surrounding sequences. Such shorter islands can be achieved by fragmenting the target nucleic acid prior to tagmentation.

Linked Transposomes

Figure 58:
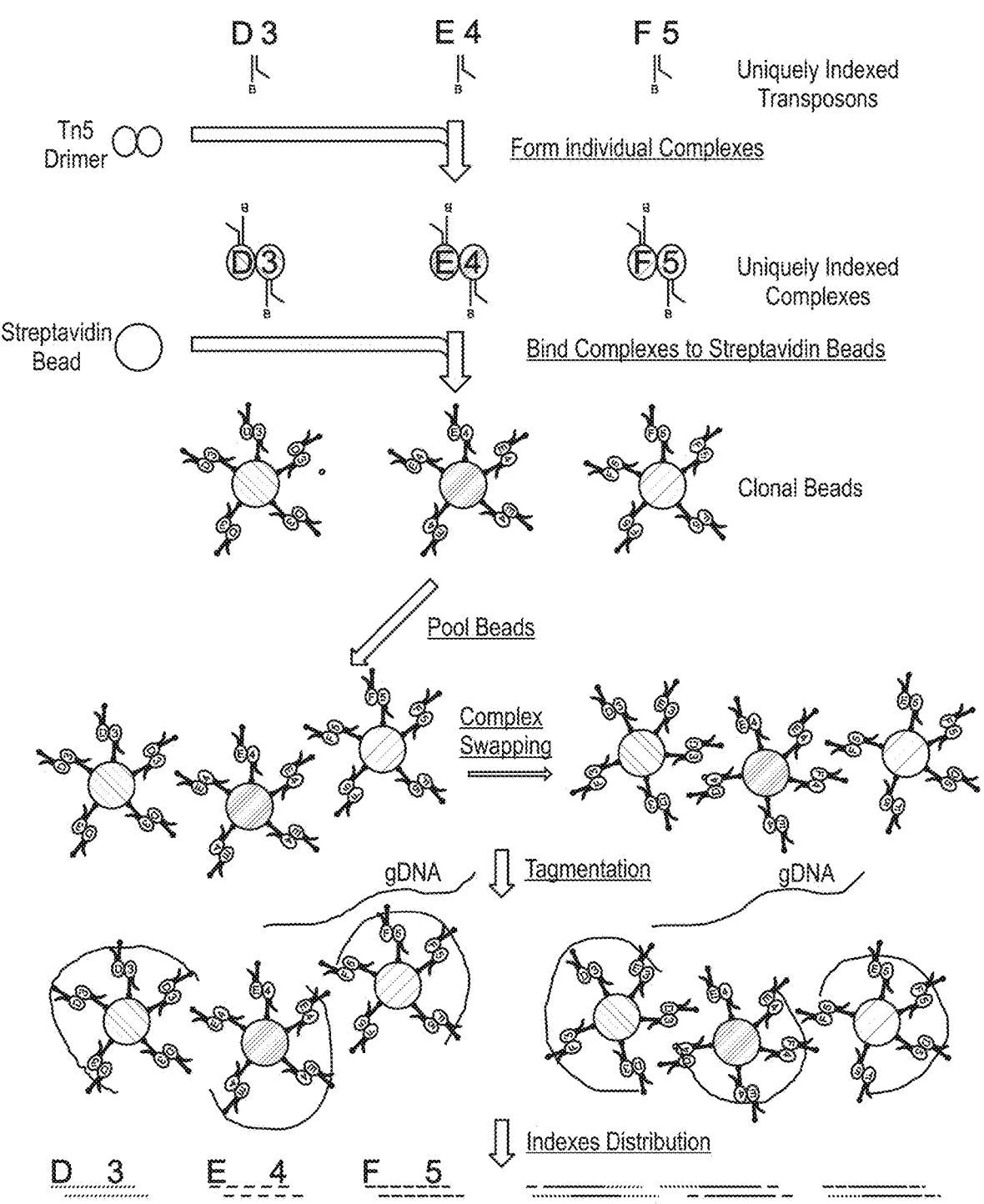
FIG. 58 shows some possible mechanisms of ME swapping.

In some embodiments, transposases are multimeric in a transposome complex, e.g., they form dimers, tetramers etc. in a transposome complex. Inventors of the present application have surprisingly and unexpectedly found that linking the monomer transposases in multimeric transposome complex or linking the transposon ends of a transposome monomer in multimeric transposome complex has several advantages. First, the linking of the transposases or the transposons leads to the complexes that are more stable and a large fraction is in an active state. Second, lower concentrations of transposomes can potentially be used in the fragmentation by transposition reaction. Third, the linking leads to lower exchange of the mosaic ends (ME) of transposome complexes, thus less mixing of barcodes or adaptor molecules. Such swapping of ME ends are possible if the complexes fall apart and reform, or in case where transposomes are immobilized on solid support by streptavidin/biotin, the streptavidin/biotin interaction can break and reform, or when there is a possible contamination. Inventors of the present application noted that there is a significant swap or exchange of ME ends under various reaction conditions. In some embodiments, the exchange can be as high as 15%. The exchange is pronounced in high salt buffer and the exchange is reduced in glutamate buffer. FIGS. 57 and 58 shows some possible mechanisms of ME swapping.

In some embodiments, the transposase subunits in the transposome complex can be linked to each other by covalent and non-covalent means. In some embodiments, transposase monomers can be linked before making the transposome complex (before addition of the transposons). In some embodiments, transposase monomers can be linked after transposome formation.

Figure 59:
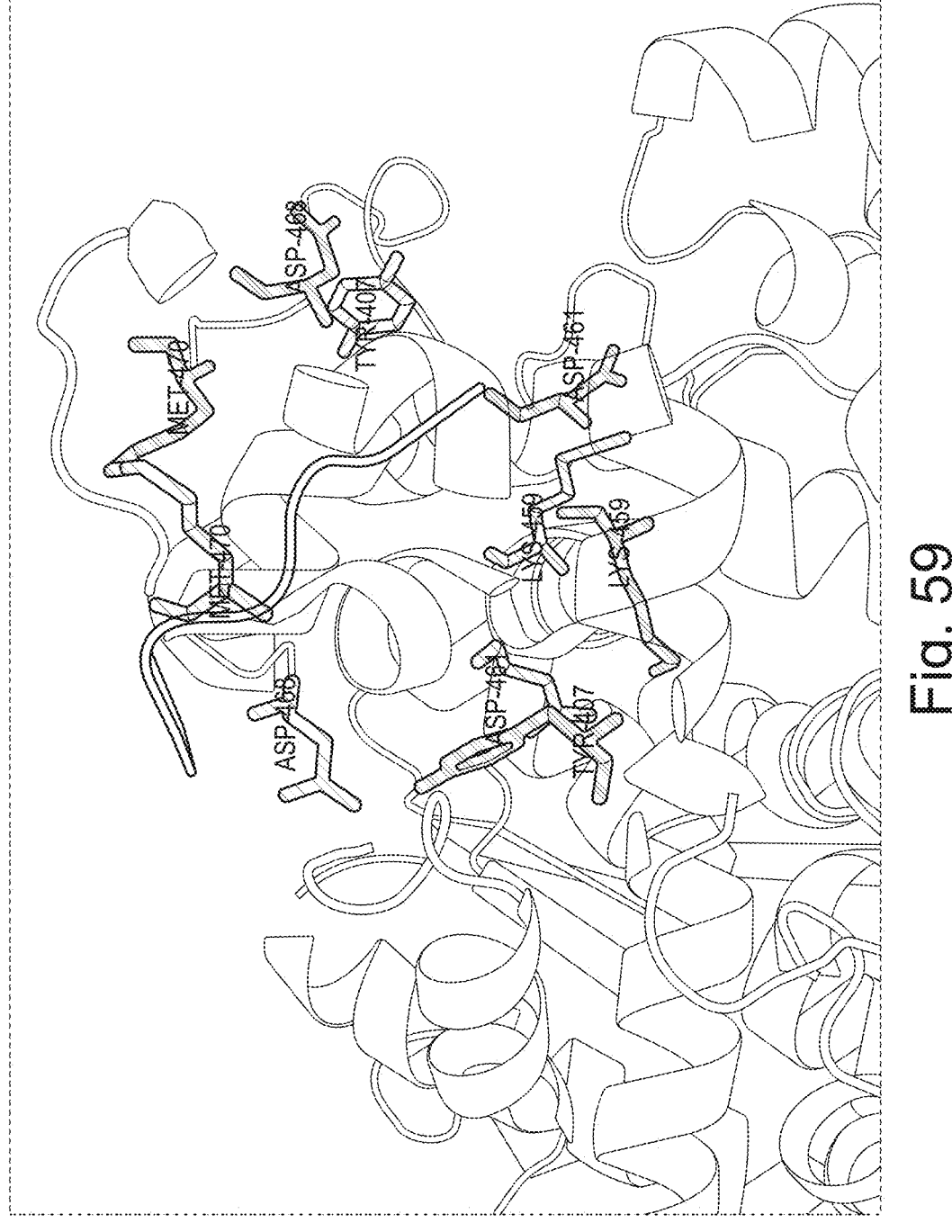
FIG. 59 shows a portion of Tn5 transposase with exemplary amino acid residues Asp468, Tyr407, Asp461, Lys459, Ser458, Gly462, Ala466, Met470 that can be substituted with Cys.
Figure 60:
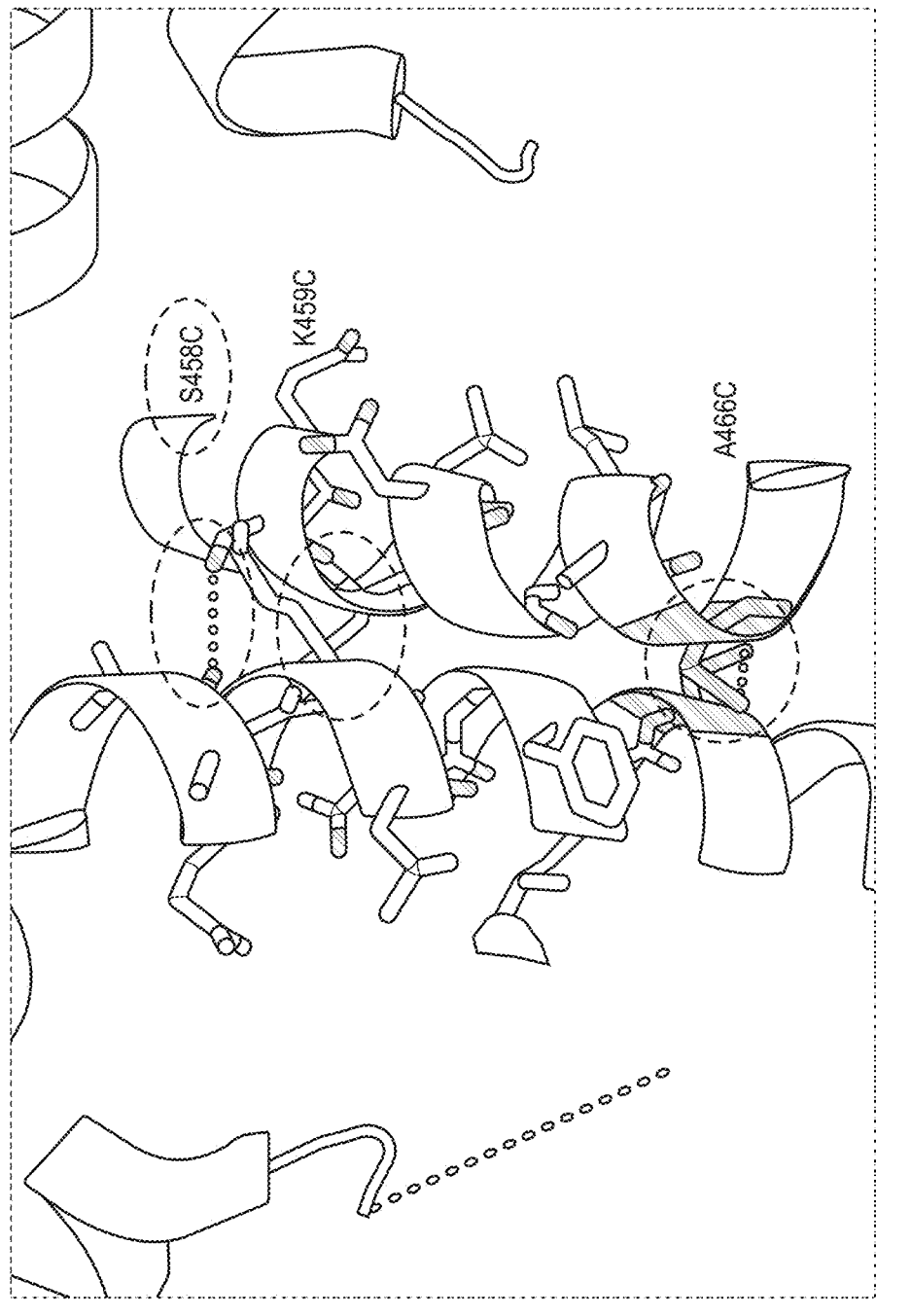
FIG. 60 shows a portion of Tn5 transposase with amino acid substitution of S458C, K459C and A466C, such that cysteine residues can form disulfide bond between two monomeric units.
Figure 61:
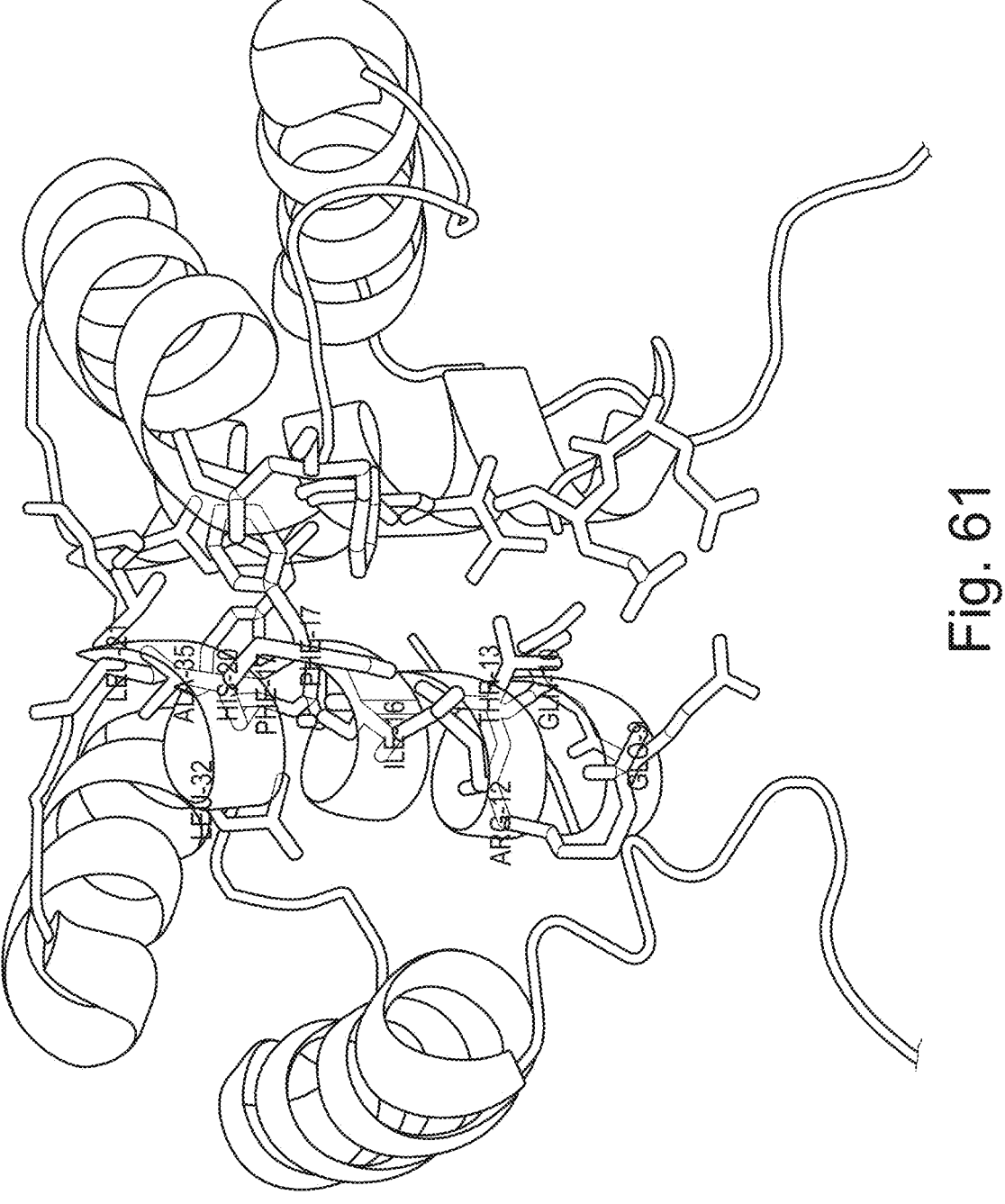
FIG. 61 shows an exemplary scheme of making and using a dimer transposase (dTnp)-nanoparticle (NP) bioconjugate (dTnp-NP) using amine coated nanoparticle.

In some embodiments, native amino acid residues may be substituted with Cysteine (Cys) amino acids at the multimeric interface to promote disulfide bond formation. For example, in Tn5 transposase, Asp468, Tyr407, Asp461, Lys459, Ser458, Gly462, Ala466, Met470 may be substituted with Cys to promote disulfide bond between the monomer subunits and shown in FIGS. 59 and 60. For Mos-1 transposase, exemplary amino acids that can be substituted with cysteine include, but are not limited to Leu21, Leu32, Ala35, His20, Phe17, Phe36, Ile16, Thr13, Arg12, Gln10, Glu9 and shown in FIG. 61. In some embodiments, the modified transposase with amino acid residues substituted with cysteine can chemically cross-linked to each other using a chemical cross-linker using maleimide or pyridyldithiol reactive groups. Exemplary chemical cross-linkers are available commercially from Pierce Protein Biology/ThermoFisher Scientific (Grand Island, NY, USA).

In some embodiments, transposome multimer complexes can be covalently linked to solid support. Exemplary solid supports include but are not limited to nanoparticles, beads, flow cell surfaces, column matrices. In some embodiments, solid surfaces may be coated with amine groups. Modified transposase with amino acid residues substituted with cysteine can be chemically cross-linked to such amine groups using an amine-to-sulfhydryl crosslinker (i.e., succinimidyl-4-(N-maleimidomethyl)cyclohexane-1-carboxylate (SMCC)). Exemplary scheme is shown in FIG. 62. In some embodiments, a maleimide-PEG-biotin crosslinker may be used to couple dTnp to a streptavidin coated solid surface.

In some embodiments, transposase gene can be modified to express multimeric protein in a single polypeptide. For example, Tn5 or Mos-1 genes can be modified to express two Tn5 or Mos-1 proteins in a single polypeptide. Similarly Mu transposase gene can be modified to encode four mu transposase units in a single polypeptide.

Figure 63:
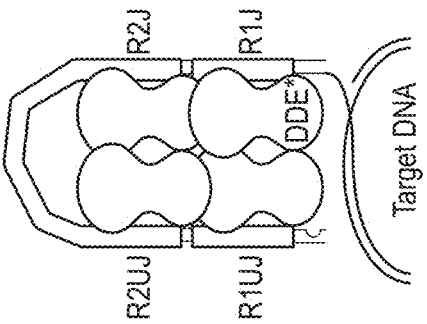
FIG. 63 shows a Mu transposome complex where transposon ends are linked.

In some embodiments, the transposon ends of a transposome monomer unit can be linked to form a linked transposome multimer complex. Linking the transposon ends allow insertion of primer sites, sequencing primers, amplification primers or any role DNA can play into gDNA without fragmenting the target DNA. Insertion of such functionality are advantages in haplotyping assays or junction tagging assays in which information needs to be extracted from intact molecules or in which sub-sampling are important. In some embodiments, transposon ends of Mu transposomes can be linked to a "looped" Mu transposase/transposon configuration. Since Mu is a tetramer, various configurations are possible but not limited by linking either R2UJ and/or R1UJ with R2J and/or R1J. In these configurations R2UJ and R1UJ can/are not connected with R2J and R1J, respectively. FIG. 63 shows a Mu transposome complex where transposon ends are linked. In some embodiments, transposon ends of Tn5 or transposon ends of Mos-1 transposomes can be linked.

As used herein the term "transposon" means a double-stranded DNA that exhibits only the nucleotide sequences (the "transposon end sequences") that are necessary to form the complex with the transposase or integrase enzyme that is functional in an in vitro transposition reaction. A transposon forms a "complex" or a "synaptic complex" or a "transposome complex" or a "transposome composition with a transposase or integrase that recognizes and binds to the transposon, and which complex is capable of inserting or transposing the transposon into target DNA with which it is incubated in an in vitro transposition reaction. A transposon exhibits two complementary sequences consisting of a "transferred transposon sequence" or "transferred strand" and a "non-transferred transposon sequence," or "non transferred strand". For example, one transposon that forms a complex with a hyperactive Tn5 transposase (e.g., EZ-Tn5™ Transposase, EPICENTRE Biotechnologies, Madison, Wis., USA) that is active in an in vitro transposition reaction comprises a transferred strand that exhibits a "transferred transposon sequence" as follows:

(SEQ ID NO: 3)
5' AGATGTGTATAAGAGACAG 3'_ and a non-transferred strand that exhibits a "non-transferred transposon sequence" as follows:

(SEQ ID NO: 4)
5' CTGTCT CTTATACACATCT 3'.

The 3'-end of a transferred strand is joined or transferred to target DNA in an in vitro transposition reaction. The non-transferred strand, which exhibits a transposon sequence that is complementary to the transferred transposon end sequence, is not joined or transferred to the target DNA in an in vitro transposition reaction. In some embodiments, the transposon sequences may comprise one or more of the following: a barcode, an adaptor sequence, a tag sequence, a primer binding sequence, a capture sequence, unique molecular identifier (UMI) sequence.

As used herein the term "adaptor" means a nucleic acid sequence that can comprise a barcode, a primer binding sequence, a capture sequence, a sequence complementary to a capture sequence, unique molecular identifier (UMI) sequence, an affinity moiety, restriction site.

As used herein the term "contiguity information" refers to a spatial relationship between two or more DNA fragments based on shared information. The shared aspect of the information can be with respect to adjacent, compartmental and distance spatial relationships. Information regarding these relationships in turn facilitates hierarchical assembly or mapping of sequence reads derived from the DNA fragments. This contiguity information improves the efficiency and accuracy of such assembly or mapping because traditional assembly or mapping methods used in association with conventional shotgun sequencing do not take into account the relative genomic origins or coordinates of the individual sequence reads as they relate to the spatial relationship between the two or more DNA fragments from which the individual sequence reads were derived. Therefore, according to the embodiments described herein, methods of capturing contiguity information may be accomplished by short range contiguity methods to determine adjacent spatial relationships, mid-range contiguity methods to determine compartmental spatial relationships, or long range contiguity methods to determine distance spatial relationships. These methods facilitate the accuracy and quality of DNA sequence assembly or mapping, and may be used with any sequencing method, such as those described above.

Contiguity information includes the relative genomic origins or coordinates of the individual sequence reads as they relate to the spatial relationship between the two or more DNA fragments from which the individual sequence reads were derived. In some embodiments, contiguity information includes sequence information from non-overlapping sequence reads.

In some embodiments, the contiguity information of a target nucleic acid sequence is indicative of haplotype information. In some embodiments, the contiguity information of a target nucleic acid sequence is indicative of genomic variants.

As used herein the term "maintaining the contiguity of the target nucleic acid" in the context of fragmenting a nucleic acid means maintaining the order of the nucleic acid sequence of the fragments from the same target nucleic acid.

As used herein the term "at least a portion" and/or grammatical equivalents thereof can refer to any fraction of a whole amount. For example, "at least a portion" can refer to at least about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 99%, 99.9% or 100% of a whole amount.

As used herein the term "about" means +/−10%.

As used herein, the term "sequencing read" and/or grammatical equivalents thereof can refer to a repetitive process of physical or chemical steps that is carried out to obtain signals indicative of the order of monomers in a polymer. The signals can be indicative of an order of monomers at single monomer resolution or lower resolution. In particular embodiments, the steps can be initiated on a nucleic acid target and carried out to obtain signals indicative of the order of bases in the nucleic acid target. The process can be carried out to its typical completion, which is usually defined by the point at which signals from the process can no longer distinguish bases of the target with a reasonable level of certainty. If desired, completion can occur earlier, for example, once a desired amount of sequence information has been obtained. A sequencing read can be carried out on a single target nucleic acid molecule or simultaneously on a population of target nucleic acid molecules having the same sequence, or simultaneously on a population of target nucleic acids having different sequences. In some embodiments, a sequencing read is terminated when signals are no longer obtained from one or more target nucleic acid molecules from which signal acquisition was initiated. For example, a sequencing read can be initiated for one or more target nucleic acid molecules that are present on a solid phase substrate and terminated upon removal of the one or more target nucleic acid molecules from the substrate. Sequencing can be terminated by otherwise ceasing detection of the target nucleic acids that were present on the substrate when the sequencing run was initiated. Exemplary methods of sequencing are described in U.S. Pat. No. 9,029,103, which is incorporated herein by reference in its entirety.

As used herein, the term "sequencing representation" and/or grammatical equivalents thereof can refer to information that signifies the order and type of monomeric units in the polymer. For example, the information can indicate the order and type of nucleotides in a nucleic acid. The information can be in any of a variety of formats including, for example, a depiction, image, electronic medium, series of symbols, series of numbers, series of letters, series of colors, etc. The information can be at single monomer resolution or at lower resolution. An exemplary polymer is a nucleic acid, such as DNA or RNA, having nucleotide units. A series of "A," "T," "G," and "C" letters is a well-known sequence representation for DNA that can be correlated, at single nucleotide resolution, with the actual sequence of a DNA molecule. Other exemplary polymers are proteins having amino acid units and polysaccharides having saccharide units.

Solid Support

Throughout this application, solid support and solid surface are used interchangeably. In some embodiments, the solid support or its surface is non-planar, such as the inner or outer surface of a tube or vessel. In some embodiments, the solid support comprises microspheres or beads. By "microspheres" or "beads" or "particles" or grammatical equivalents herein is meant small discrete particles. Suitable bead compositions include, but are not limited to, plastics, ceramics, glass, polystyrene, methylstyrene, acrylic polymers, paramagnetic materials, thoria sol, carbon graphite, titanium dioxide, latex or cross-linked dextrans such as Sepharose, cellulose, nylon, cross-linked micelles and Teflon, as well as any other materials outlined herein for solid supports may all be used. "Microsphere Detection Guide" from Bangs Laboratories, Fishers Ind. is a helpful guide. In certain embodiments, the microspheres are magnetic microspheres or beads. In some embodiments, the beads can be color coded. For example, MicroPlex® Microspheres from Luminex, Austin, TX may be used.

The beads need not be spherical; irregular particles may be used. Alternatively or additionally, the beads may be porous. The bead sizes range from nanometers, i.e. about 10 nm, to millimeters in diameter, i.e. 1 mm, with beads from about 0.2 micron to about 200 microns being preferred, and from about 0.5 to about 5 micron being particularly preferred, although in some embodiments smaller or larger beads may be used. In some embodiments, beads can be about 0.1, 0.2, 0.3, 0.4, 0.5, 0.6, 0.7, 0.8, 0.9, 1, 1.5, 2, 2.5, 2.8, 3, 3.5, 4, 4.5, 5, 5.5, 6, 6.5, 7, 7.5, 8, 8.5, 9, 9.5, 10, 10.5, 15, 20, 25, 30, 35, 40, 45, 50, 55, 60, 65, 70, 75, 80, 85, 90, 95, 100, 150, or 200 µm in diameter.

Transposomes

A "transposome" comprises an integration enzyme such as an integrase or transposase, and a nucleic acid comprising an integration recognition site, such as a transposase recognition site. In embodiments provided herein, the transposase can form a functional complex with a transposase recognition site that is capable of catalyzing a transposition reaction. The transposase may bind to the transposase recognition site and insert the transposase recognition site into a target nucleic acid in a process sometimes termed "tagmentation". In some such insertion events, one strand of the transposase recognition site may be transferred into the target nucleic acid. In one example, a transposome comprises a dimeric transposase comprising two subunits, and two non-contiguous transposon sequences. In another example, a transposome comprises a transposase comprises a dimeric transposase comprising two subunits, and a contiguous transposon sequence.

Some embodiments can include the use of a hyperactive Tn5 transposase and a Tn5-type transposase recognition site (Goryshin and Reznikoff, J. Biol. Chem., 273:7367 (1998)), or MuA transposase and a Mu transposase recognition site comprising R1 and R2 end sequences (Mizuuchi, K., Cell, 35: 785, 1983; Savilahti, H, et al., EMBO J., 14: 4893, 1995). An exemplary transposase recognition site that forms a complex with a hyperactive Tn5 transposase (e.g., EZ-Tn5™ Transposase, Epicentre Biotechnologies, Madison, Wisconsin) comprises the following 19b transferred strand (sometimes "M" or "ME") and non-transferred strands: 5' AGATGTGTATAAGAGACAG 3' (SEQ ID NO: 3), 5' CTGTCT CTTATACACATCT 3' (SEQ ID NO: 4), respectively. ME sequences can also be used as optimized by a skilled artisan.

More examples of transposition systems that can be used with certain embodiments of the compositions and methods provided herein include *Staphylococcus aureus* Tn552 (Colegio et al., J. Bacteriol., 183: 2384-8, 2001; Kirby C et al., Mol. Microbiol., 43: 173-86, 2002), Ty1 (Devine & Boeke, Nucleic Acids Res., 22: 3765-72, 1994 and International Publication WO 95/23875), Transposon Tn7 (Craig, N L, Science. 271: 1512, 1996; Craig, N L, Review in: Curr Top Microbiol Immunol., 204:27-48, 1996), Tn/O and IS10 (Kleckner N, et al., Curr Top Microbiol Immunol., 204:49-82, 1996), Mariner transposase (Lampe D J, et al., EMBO J., 15: 5470-9, 1996), Tc1 (Plasterk R H, Curr. Topics Microbiol. Immunol., 204: 125-43, 1996), P Element (Gloor, G B, Methods Mol. Biol., 260: 97-114, 2004), Tn3 (Ichikawa & Ohtsubo, J Biol. Chem. 265:18829-32, 1990), bacterial insertion sequences (Ohtsubo & Sekine, Curr. Top. Microbiol. Immunol. 204: 1-26, 1996), retroviruses (Brown, et al., Proc Natl Acad Sci USA, 86:2525-9, 1989), and retrotransposon of yeast (Boeke & Corces, Annu Rev Microbiol. 43:403-34, 1989). More examples include IS5, Tn10, Tn903, IS911, Sleeping Beauty, SPIN, hAT, PiggyBac, Hermes, TcBuster, AeBuster1, Tol2, and engineered versions of transposase family enzymes (Zhang et al., (2009) PLoS Genet. 5:e1000689. Epub 2009 Oct. 16; Wilson C. et al (2007) J. Microbiol. Methods 71:332-5).

More examples of integrases that may be used with the methods and compositions provided herein include retroviral integrases and integrase recognition sequences for such retroviral integrases, such as integrases from HIV-1, HIV-2, SIV, PFV-1, RSV.

Barcodes

Generally, a barcode can include one or more nucleotide sequences that can be used to identify one or more particular nucleic acids. The barcode can be an artificial sequence, or can be a naturally occurring sequence generated during transposition, such as identical flanking genomic DNA sequences (g-codes) at the end of formerly juxtaposed DNA fragments. In some embodiments, the barcodes are artificial sequences that are absent in the target nucleic acid sequence and can be used to identify one or more target nucleic acid sequences.

A barcode can comprise at least about 1, 2, 3, 4, 5, 6, 7, 8, 9, 10, 11, 12, 13, 14, 15, 16, 17, 18, 19, 20 or more consecutive nucleotides. In some embodiments, a barcode comprises at least about 10, 20, 30, 40, 50, 60, 70 80, 90, 100 or more consecutive nucleotides. In some embodiments, at least a portion of the barcodes in a population of nucleic acids comprising barcodes is different. In some embodiments, at least about 10%, 20%, 30%, 40%, 50%, 60%, 70%, 80%, 90%, 95%, 99% of the barcodes are different. In more such embodiments, all of the barcodes are different. The diversity of different barcodes in a population of nucleic acids comprising barcodes can be randomly generated or non-randomly generated.

In some embodiments, a transposon sequence comprises at least one barcode. In some embodiments, such as transposomes comprising two non-contiguous transposon sequences, the first transposon sequence comprises a first barcode, and the second transposon sequence comprises a second barcode. In some embodiments, a transposon sequence comprises a barcode comprising a first barcode sequence and a second barcode sequence. In some of the foregoing embodiments, the first barcode sequence can be identified or designated to be paired with the second barcode sequence. For example, a known first barcode sequence can be known to be paired with a known second barcode sequence using a reference table comprising a plurality of first and second bar code sequences known to be paired to one another.

In another example, the first barcode sequence can comprise the same sequence as the second barcode sequence. In another example, the first barcode sequence can comprise the reverse complement of the second barcode sequence. In some embodiments, the first barcode sequence and the second barcode sequence are different. The first and second barcode sequences may comprise a bi-code.

In some embodiments of compositions and methods described herein, barcodes are used in the preparation of template nucleic acids. As will be understood, the vast number of available barcodes permits each template nucleic acid molecule to comprise a unique identification. Unique identification of each molecule in a mixture of template nucleic acids can be used in several applications. For example, uniquely identified molecules can be applied to identify individual nucleic acid molecules, in samples having multiple chromosomes, in genomes, in cells, in cell types, in cell disease states, and in species, for example, in haplotype sequencing, in parental allele discrimination, in metagenomic sequencing, and in sample sequencing of a genome.

Exemplary barcode sequences include, but are not limited to TATAGCCT, ATAGAGGC, CCTATCCT, GGCTCTGA, AGGCGAAG, TAATCTTA, CAGGACGT, and GTACTGAC.

Primer Sites

In some embodiments, a transposon sequence can include a "sequencing adaptor" or "sequencing adaptor site", that is to say a region that comprises one or more sites that can hybridize to a primer. In some embodiments, a transposon sequence can include at least a first primer site useful for amplification, sequencing, and the like. Exemplary sequences of sequence binding sites include, but are not limited to AATGATACGGCGACCACCGAGATCTACAC (SEQ ID NO: 1) (P5 sequence) and CAAGCAGAA-GACGGCATACGAGAT (SEQ ID NO: 2) (P7 sequence).

Target Nucleic Acids

A target nucleic acid can include any nucleic acid of interest. Target nucleic acids can include DNA, RNA, peptide nucleic acid, morpholino nucleic acid, locked nucleic acid, glycol nucleic acid, threose nucleic acid, mixed samples of nucleic acids, polyploidy DNA (i.e., plant DNA), mixtures thereof, and hybrids thereof. In a preferred embodiment, genomic DNA or amplified copies thereof are used as the target nucleic acid. In another preferred embodiment, cDNA, mitochondrial DNA or chloroplast DNA is used. In some embodiments, the target nucleic acid is mRNA.

In some embodiments, target nucleic acid is from a single cell or from fractions of a single cell. In some embodiments, the target nucleic acid is from a single organelle. Exemplary single organelle includes but is not limited to single nuclei, single mitochondria, and a single ribosome. In some embodiments, target nucleic acid is from formalin fixed paraffin embedded (FFPE) sample. In some embodiments, target nucleic acid is cross-linked nucleic acid. In some embodiments, the target nucleic acid is cross-linked with protein. In some embodiments, the target nucleic acid is cross-linked DNA. In some embodiments, the target nucleic acid is histone protected DNA. In some embodiments, histones are removed from the target nucleic acid. In some embodiments, target nucleic acid is from nucleosomes. In some embodiments, target nucleic acid is from nucleosomes from which nuclear proteins are removed.

A target nucleic acid can comprise any nucleotide sequence. In some embodiments, the target nucleic acid comprises homopolymer sequences. A target nucleic acid can also include repeat sequences. Repeat sequences can be any of a variety of lengths including, for example, 2, 5, 10, 20, 30, 40, 50, 100, 250, 500 or 1000 nucleotides or more. Repeat sequences can be repeated, either contiguously or non-contiguously, any of a variety of times including, for example, 2, 3, 4, 5, 6, 7, 8, 9, 10, 15 or 20 times or more.

Some embodiments described herein can utilize a single target nucleic acid. Other embodiments can utilize a plurality of target nucleic acids. In such embodiments, a plurality of target nucleic acids can include a plurality of the same target nucleic acids, a plurality of different target nucleic acids where some target nucleic acids are the same, or a plurality of target nucleic acids where all target nucleic acids are different. Embodiments that utilize a plurality of target nucleic acids can be carried out in multiplex formats so that reagents are delivered simultaneously to the target nucleic acids, for example, in one or more chambers or on an array surface. In some embodiments, the plurality of target nucleic acids can include substantially all of a particular organism's genome. The plurality of target nucleic acids can include at least a portion of a particular organism's genome including, for example, at least about 1%, 5%, 10%, 25%, 50%, 75%, 80%, 85%, 90%, 95%, or 99% of the genome. In particular embodiments the portion can have an upper limit that is at most about 1%, 5%, 10%, 25%, 50%, 75%, 80%, 85%, 90%, 95%, or 99% of the genome.

Target nucleic acids can be obtained from any source. For example, target nucleic acids may be prepared from nucleic acid molecules obtained from a single organism or from populations of nucleic acid molecules obtained from natural sources that include one or more organisms. Sources of nucleic acid molecules include, but are not limited to, organelles, cells, tissues, organs, or organisms. Cells that may be used as sources of target nucleic acid molecules may be prokaryotic (bacterial cells, for example, *Escherichia, Bacillus, Serratia, Salmonella, Staphylococcus, Streptococcus, Clostridium, Chlamydia, Neisseria, Treponema, Mycoplasma, Borrelia, Legionella, Pseudomonas, Mycobacterium, Helicobacter, Envinia, Agrobacterium, Rhizobium,* and *Streptomyces* genera); archeaon, such as crenarchaeota, nanoarchaeota or euryarchaeotia; or eukaryotic such as fungi, (for example, yeasts), plants, protozoans and other parasites, and animals (including insects (for example, *Drosophila* spp.), nematodes (e.g., *Caenorhabditis elegans*), and mammals (for example, rat, mouse, monkey, non-human primate and human). Target nucleic acids and template nucleic acids can be enriched for certain sequences of interest using various methods well known in the art. Examples of such methods are provided in Int. Pub. No. WO2012/108864, which is incorporated herein by reference in its entirety. In some embodiments, nucleic acids may be further enriched during methods of preparing template libraries. For example, nucleic acids may be enriched for certain sequences, before insertion of transposomes after insertion of transposomes and/or after amplification of nucleic acids.

In addition, in some embodiments, target nucleic acids and/or template nucleic acids can be highly purified, for example, nucleic acids can be at least about 70%, 80%, 90%, 95%, 96%, 97%, 98%, 99%, or 100% free from contaminants before use with the methods provided herein. In some embodiments, it is beneficial to use methods known in the art that maintain the quality and size of the target nucleic acid, for example isolation and/or direct transposition of target DNA may be performed using agarose plugs. Transposition can also be performed directly in cells, with population of cells, lysates, and non-purified DNA.

In some embodiments, target nucleic acid may be obtained from a biological sample or a patient sample. The term "biological sample" or "patient sample" as used herein includes samples such as tissues and bodily fluids. "Bodily fluids" may include, but are not limited to, blood, serum, plasma, saliva, cerebral spinal fluid, pleural fluid, tears, lactal duct fluid, lymph, sputum, urine, amniotic fluid, and semen. A sample may include a bodily fluid that is "acellular." An "acellular bodily fluid" includes less than about 1% (w/w) whole cellular material. Plasma or serum are examples of acellular bodily fluids. A sample may include a specimen of natural or synthetic origin (i.e., a cellular sample made to be acellular).

In some embodiments of the above disclosed methods, target nucleic acid can be fragmented (e.g., by sonication, by restriction digestion, other mechanical means) prior to exposing the target nucleic acid to the transposomes.

The term "Plasma" as used herein refers to acellular fluid found in blood. "Plasma" may be obtained from blood by removing whole cellular material from blood by methods known in the art (e.g., centrifugation, filtration, and the like).

Unless otherwise specified, the terms "a" or "an" mean "one or more" throughout this application.

When the terms "for example", "e.g.", "such as", "include", "including" or variations thereof are used herein, these terms will not be deemed to be terms of limitation, and will be interpreted to mean "but not limited to" or "without limitation."

The following Examples provide illustrative embodiments and do not in any way limit the inventions provided herein.

EXAMPLES

Example 1—DNA Cluster Yield from the Bead-Based Tagmentation Process

Figure 4:
FIG. 4 shows a data table of an example of the DNA yield in terms of cluster number from the bead-based tagmentation process of FIG. 3.

DNA cluster yield from the bead-based tagmentation process of FIG. 3 were evaluated and shown in the table of FIG. 4. In this example, 50, 250, and 1000 ng of human NA12878 DNA were tagmented using the same batch of tagmentation beads (2.8 µm beads). A second 50 ng aliquot of NA12878 DNA was tagmented using a second batch of tagmentation beads (full repeat; 2.8 µm beads). The bead-bound tagmented DNA samples were PCR amplified and purified. An aliquot (5.4 µL) of each purified PCR product (unquantified) was diluted 270 fold to make stock sample solutions of about 50 µM. For each sample, the 50 µM stock solution was diluted to 15, 19, 21, and 24 µM. The diluted samples were loaded onto a flow cell for cluster generation and sequencing. The data show that starting from the same dilution (~50 µM), cluster numbers are between 100-114% for the three different input levels (i.e., 50, 250, and 1000 ng) using the same set of beads. The cluster number for the 50 ng full repeat (with a different batch of beads) was 81%. Different dilutions (15, 19, 21, and 24 µM) yield the same number of clusters within about 10%. The data indicates that the beads are largely controlling the yield and yield is reproducible for different DNA inputs and different repeats.

Example 2—Reproducibility of the Bead-Based Tagmentation Process

The reproducibility of the bead-based tagmentation process of FIG. 3 is shown in FIG. 5. In this example, six different preparations of indexed beads (indexes 1 through 6; 2.8 µm beads) made at the "same" transposome density were used to prepare tagmented DNA using 50 and 500 ng of input NA12878 DNA. The tagmented DNA was PCR amplified and purified. The 12 purified PCR products were pooled into two mixtures (pool 1 and pool 2) of six for two HiSeq lanes. Each pool includes 3-50 ng and 3-500 ng samples per lane. Data table 500 shows the median insert size and the mean insert size for each indexed sample.

Example 3—Insert Size of Pool 1 and the Insert Size of Pool 2

Figures 6A, 6B:
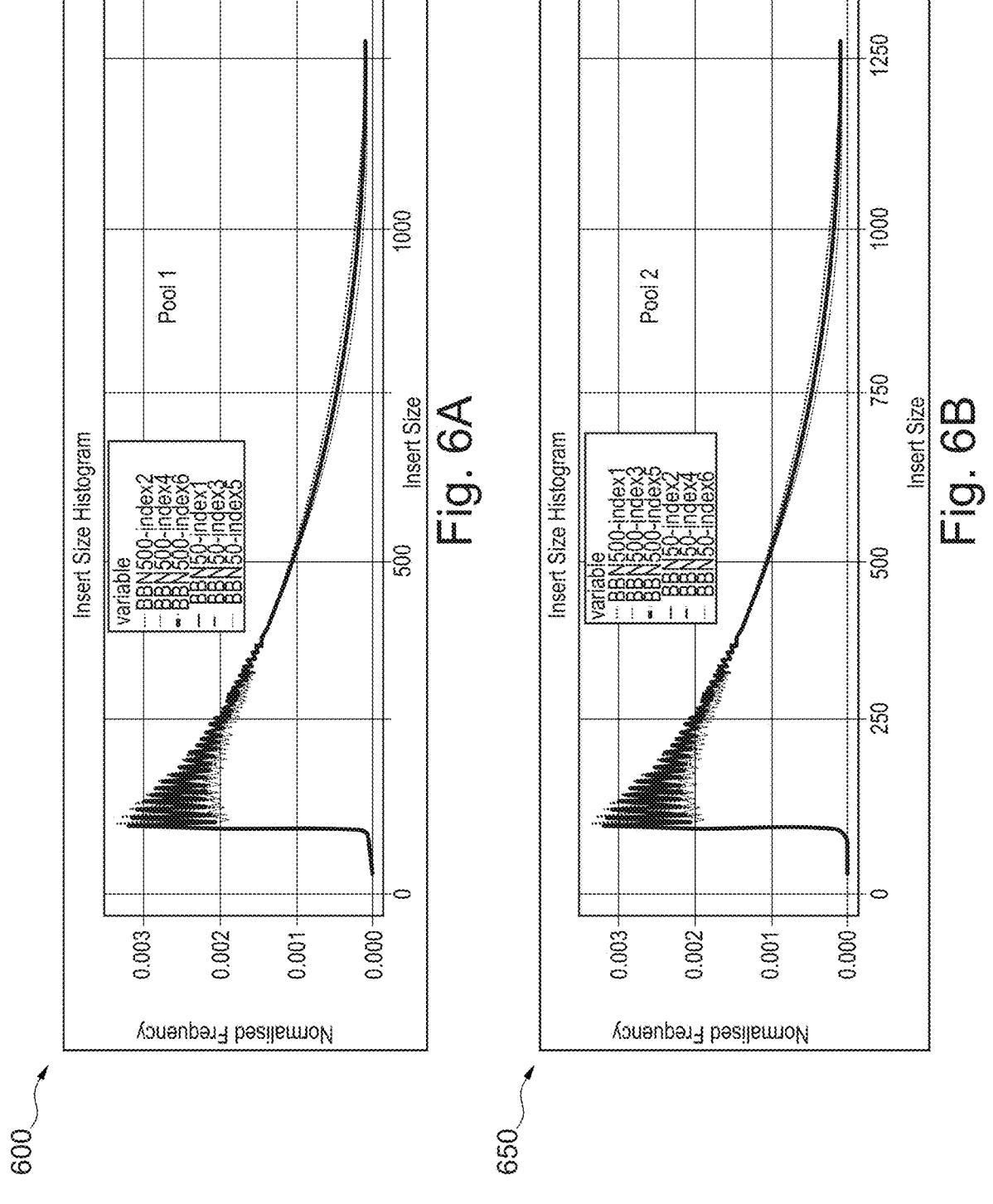
FIGS. 6A and 6B show a plot of the insert size of pool 1 and a plot of the insert size of pool 2, respectively, of the indexed samples of FIG. 5.

The insert size of pool 1 and the insert size of pool 2 are shown in FIG. 6A (Plot 600) and FIG. 6B (Plot 650), respectively, of the indexed samples of FIG. 5. The data also shows that the insert size is uniform between the six different preparations of indexed beads. Bead-based tagmentation provides a mechanism to control the size of the inserts and DNA yield.

Example 4—Reproducibility of Total Number of Reads

Figure 7:
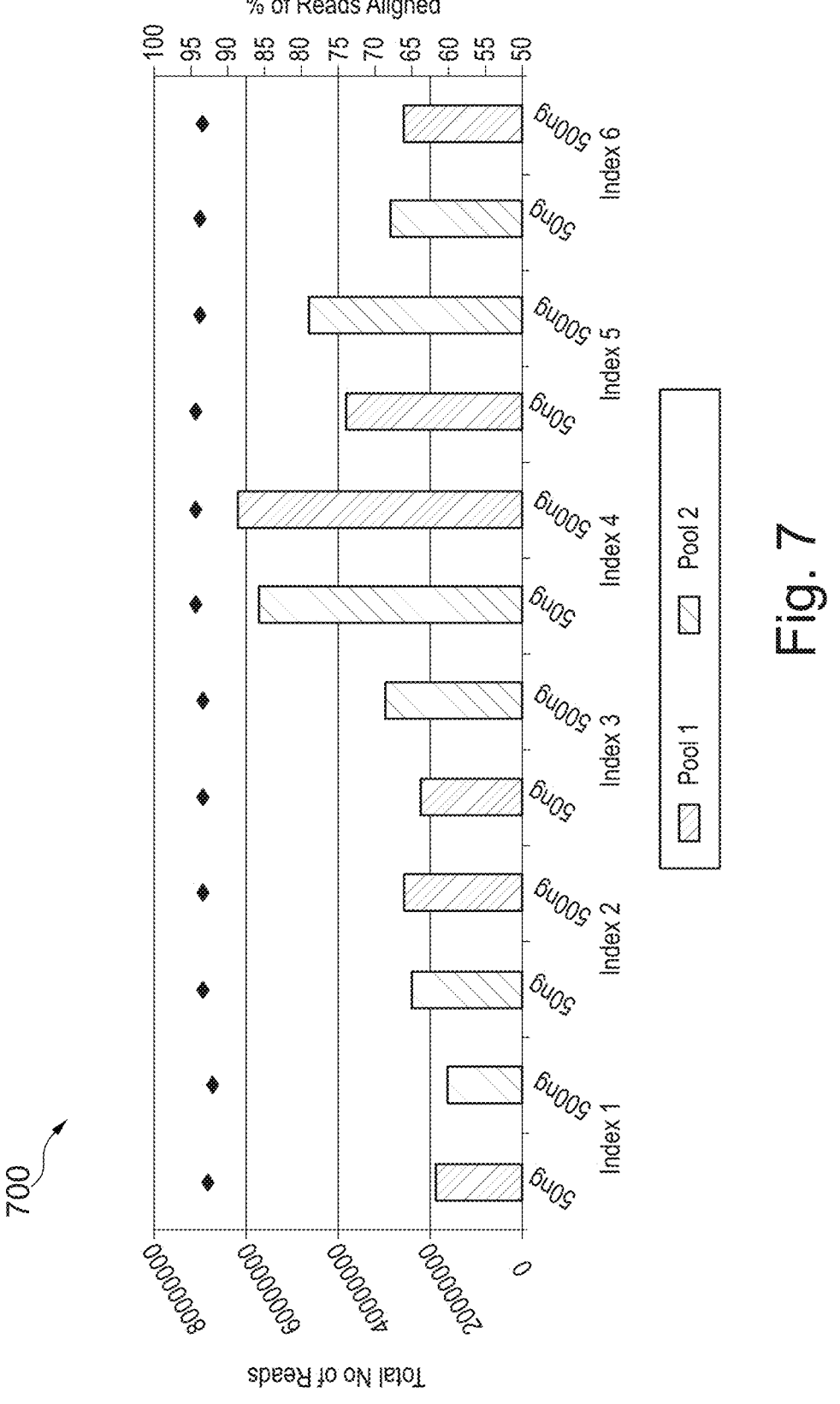
FIG. 7 shows a bar graph of the reproducibility of total number of reads and percent reads aligned for the experiment described in FIG. 5.

The reproducibility of total number of reads and percent reads aligned for the experiment described in FIG. 5 is shown in FIG. 7 (Bar graph 700). At both inputs (50 ng and 500 ng) the total number of reads is similar for the same indexed bead preparation. Four of the six indexed bead preparations (index 1, 2, 3, and 6) have very similar yields; indexed bead preparations 4 and 5 shown some variability which may be due to the index sequence.

In one application, the bead-based tagmentation process may be used in an exome enrichment assay which includes a tagmentation step, e.g., Illumina's Nextera® Rapid Capture Enrichment protocol. In the current exome enrichment assay (i.e., Illumina's Nextera® Rapid Capture Enrichment protocol), solution-based tagmentation (Nextera) is used to fragment the genomic DNA. Gene specific primers are then used to pull down specific gene fragments of interest. Two enrichment cycles are performed and fragments pulled down are then enriched by PCR and sequenced.

To evaluate the use of the bead-based tagmentation process in the exome enrichment assay, human NA12878 DNA was tagmented using 25, 50, 100, 150, 200, and 500 ng of input DNA. A control library (NA00536) was prepared from 50 ng input DNA according to the standard protocol. Each DNA input had a different index (unique identifier). Ten cycles of PCR using enhanced polymerase mastermix (EPM) were used to match standard methods and to ensure a sufficient amount of fragments were present for pulldown. The amplification protocol was 3 minutes at 72° C., 30 seconds at 98° C., followed by 10 cycles of 10 seconds at 98° C., 30 seconds at 65° C., and 1 minute at 72° C. The samples were then held at 10° C. The samples were then processed through the exome enrichment pulldown process and sequenced.

Figures 8A, 8B, 8C:
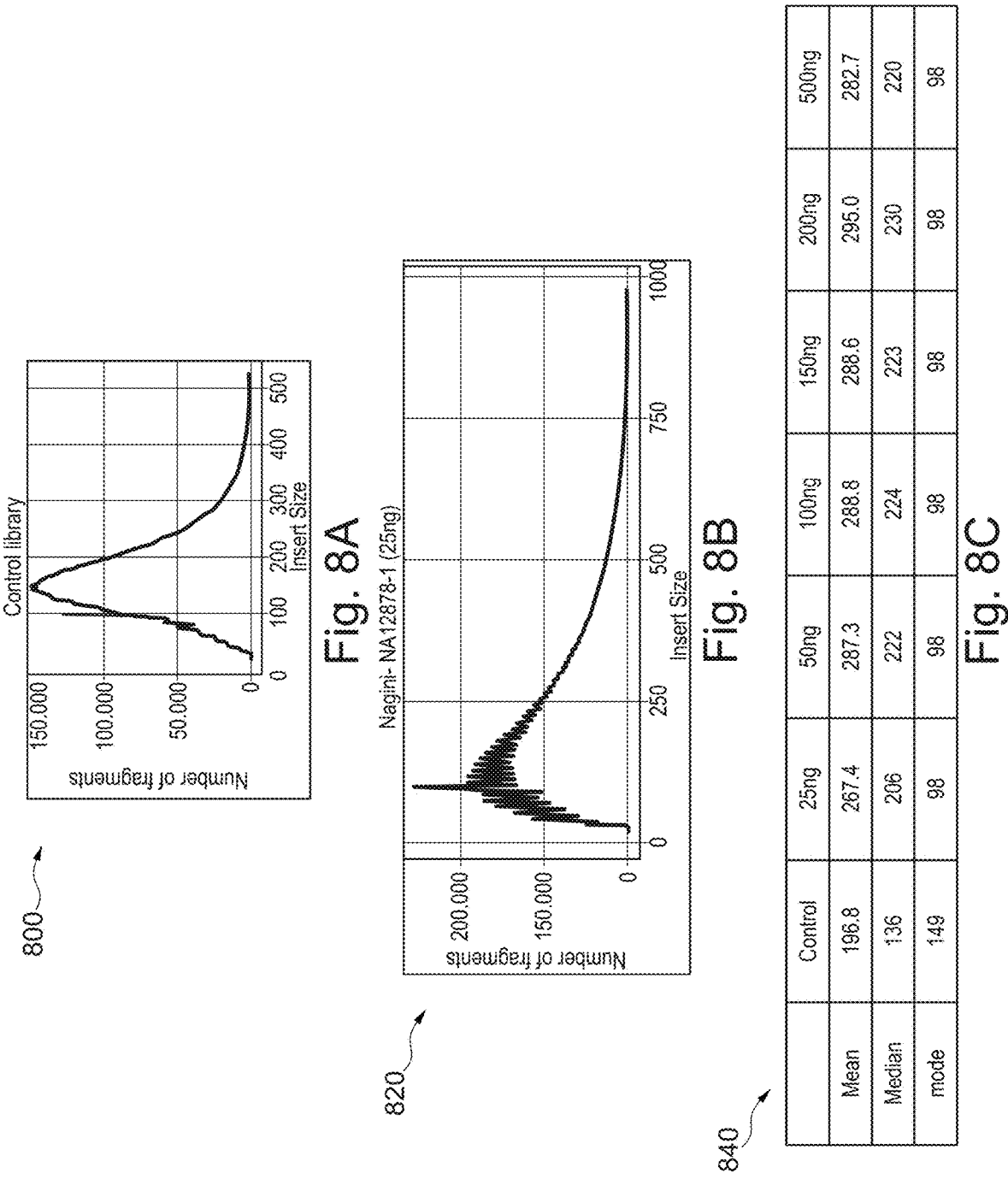
FIGS. 8A, 8B, and 8C show a plot of insert size in a control library, a plot of insert size in a bead-based tagmented library, and a summary data table, respectively, in the exome enrichment assay.

Example 5—Insert Size in a Control and Bead-Based Tagmented Library in the Exome Enrichment Assay FIGS. 8A, 8B, and 8C show a plot 800 of insert size in a control library, a plot 820 of insert size in a bead-based tagmented library, and a summary data table 840, respectively, in the exome enrichment assay. The data show that the bead-based tagmentation libraries have a wider insert size spread compared to the control library, but the insert size is very similar irrespective of the DNA input for the samples.

Example 6—Quality of the Read Sequences

Figure 9A:
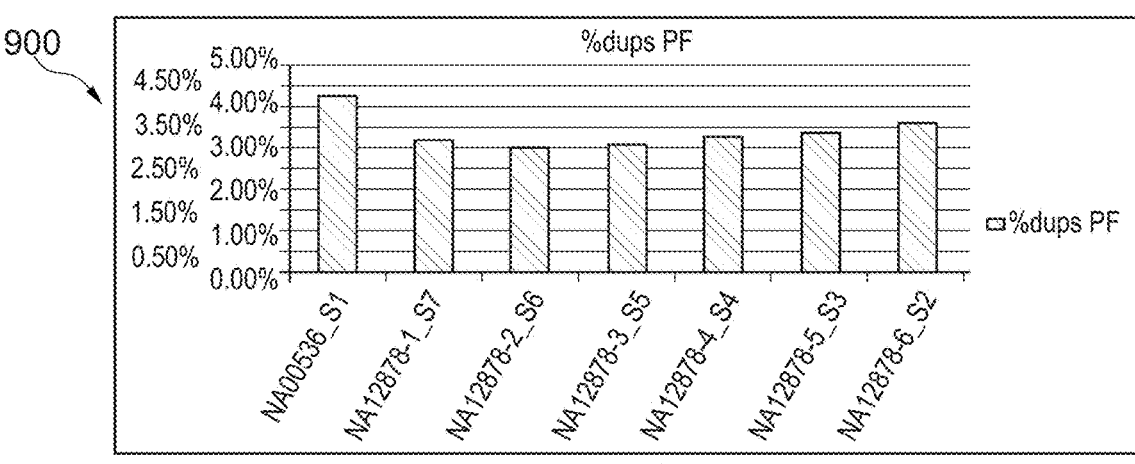
FIGS. 9A, 9B, and 9C show a bar graph of the fraction of dups PF, a bar graph of the fraction of selected bases, and bar graph of PCT usable bases on target, respectively, in the exome enrichment assay.
Figure 9B:
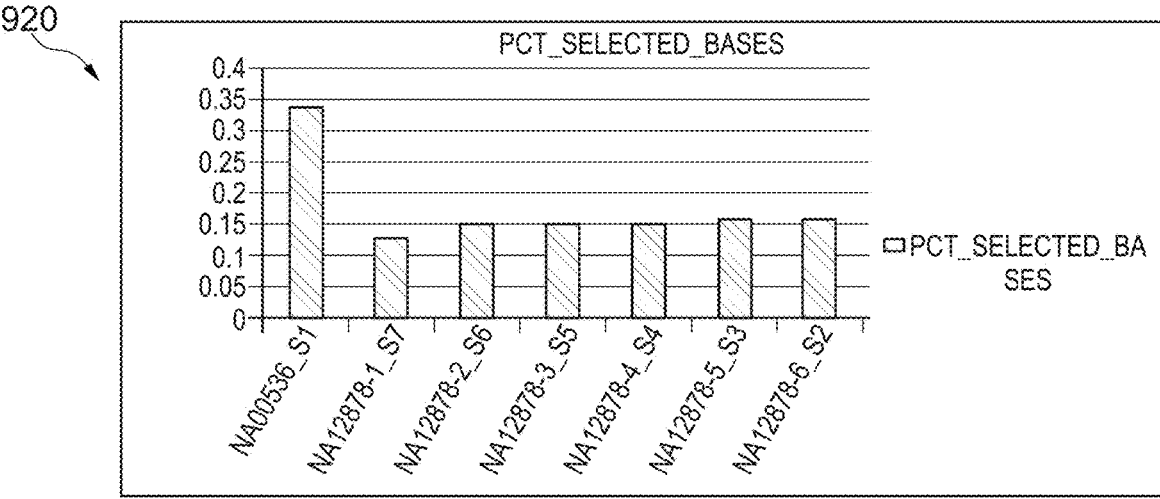
Figure 9C:
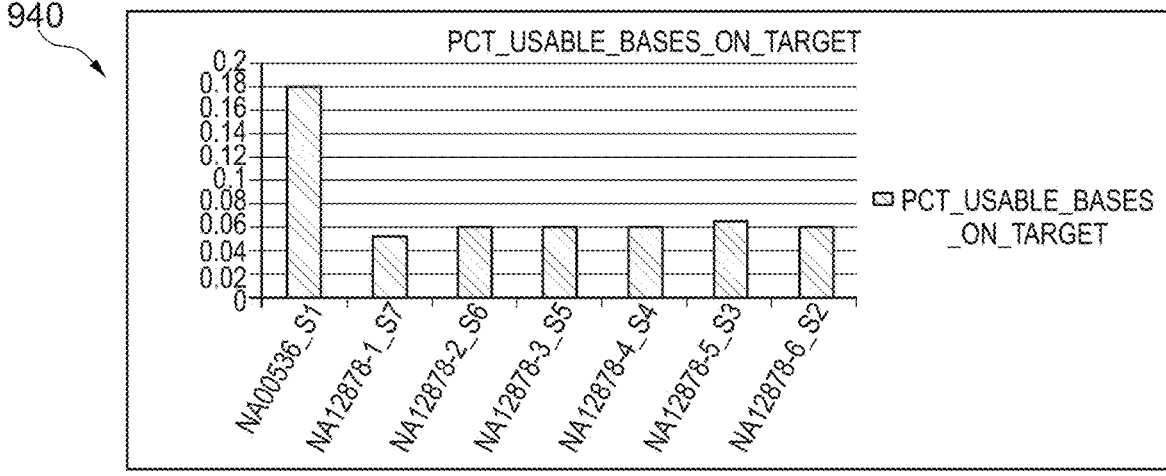

FIGS. 9A, 9B, and 9C show a bar graph 900 of percent duplicates passing filters (dups PF), a bar graph 920 of PCT selected bases, and bar graph 940 of PCT usable bases on target, respectively, in the exome enrichment assay of FIGS. 8A, 8B, and 8C. Referring to FIG. 9A, the percent dups PF is a measure of how many reads are duplicated elsewhere on the flow cell. This number will ideally be low (as here) to ensure that all clusters are bringing useful data to the results.

FIG. 9B shows PCT selected bases, which is a measure of the ratio of reads that sequence at or near the site of interest which should have been enriched during the enrichment process. Ideally this number will be close to 1 to reflect the success of the enrichment process and show that reads that should not be enriched do not get through the process.

FIG. 9C shows the PCT usable bases on target, which is a measure of the ratio of reads that actually sequence over the particular base of interest within the enriched region. Ideally all enriched reads would sequence over the base of interest within the enriched read, but due to the random nature of the tagmentation and the variable length of the inserts, reads may be enriched that do not end up being sequenced over the area of interest.

Two techniques may be used to optimize the insert size distribution. In one example, an SPRI clean-up may be used to remove fragments that are too small or too large. SPRI clean-up is a process of removing fragments that are larger or smaller than the desired size, by selective DNA precipitation based on size and either retention of the precipitated or non-precipitated DNA as desired (i.e., a first step is to precipitate only DNA that is larger than the desired size and retain the soluble smaller fragments). The smaller fragments are then further precipitated and this time the very small fragments that are not wanted (still in solution) are removed and the precipitated DNA is retained, washed and then resolubilized to give a desired size range of DNA. In another example, the spacing of active transposomes on the bead surface may be used to control the insert size distribution. For example, gaps on the bead surface may be filled with inactive transposomes (e.g., transposomes with inactive transposons).

Contiguity of the bead-based tagmentation process was assessed. Table 3 shows the number of times 0, 1, 2, or 3 reads occur within a 1000 bp windows sharing an index. Beads were generated with 9 different indexed transposomes and used to tagment a small amount of human DNA. Reads were generated, aligned, and analyzed for the number of reads within a 1000 bp or 10 Kb window that shared the same index. Some reads within a small window sharing an index may be generated by chance and a prediction of how many times this is likely to occur is given in the "Random" row of Table 3 and Table 4. The numbers in the "Bead" row show the actual number of 1000 bp (Table 3) or 10 Kb (Table 4) windows that share an index. As shown in Table 3 and Table 4, the actual number of times the same index was found within 1000 bp or 10 Kb window is significantly greater than expected in the random case. "0" windows show all the times a particular 1000 bp window had no indexed reads mapping to it. The number is largest here because only a very small amount of the human genome was sequence and most windows have no reads aligning to them. "1" is the number of times just one read maps to a 1000 bp (or 10 Kb) window; "2" the number of times 2 reads share an index within a 1000 bp (or 10 KB) window, etc. This data suggests that in over 1400 cases the same piece of DNA (over 10 Kb) is being tagmented by the same bead at least twice and up to 5 times, out of about 15000 tagmentation events. Since the fragments share an index, they are unlikely to be there by chance, but are coming from the same bead.

TABLE 3

| Number of reads in a 1000 bp windows sharing an index | | | | |
|---|---|---|---|---|
| | 0 | 1 | 2 | 3 |
| Bead | 25913666 | 15220 | 305 | 7 |
| Random | 25913334 | 15855 | 9 | 0 |

Table 4 shows the number of reads (up to 5) within a 10 kb windows sharing an index.

TABLE 4

| Number of reads in a 10 kb windows sharing an index | | | | | |
|---|---|---|---|---|---|
| | 0 | 1 | 2 | 3 | 4 | 5 |
| Bead | 2578669 | 12683 | 1267 | 169 | 28 | 3 |
| Random | 2577012 | 15742 | 64 | 1 | 0 | 0 |

Example 7—Separation of Free Transposomes from CPT-DNA

Following transposition, the reaction mixture comprising CPT-DNA and free transposomes were subjected to column chromatography using Sephacryl S-400 and Sephacryl S-200 size exclusion chromatography and shown in FIG. 22. CPT-DNA is indicated as NCP DNA.

Example 8—Optimization of Capture Probe Density on Beads

Figure 25:
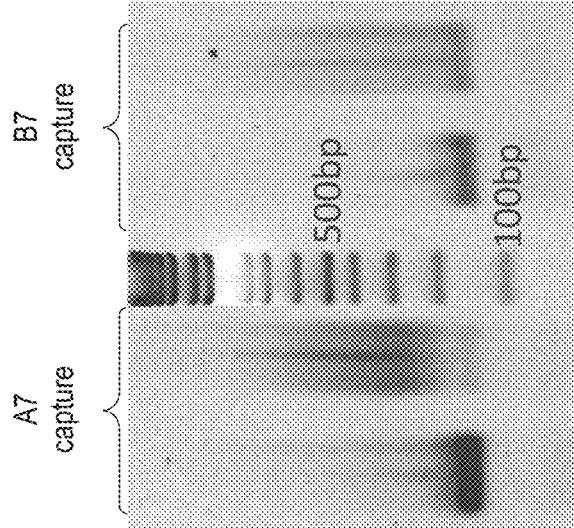
FIG. 25 shows the results of optimization of capture probe density on beads.

Densities of capture probes A7 and B7 were optimized on 1 μm beads and the results were shown in FIG. 25. Lanes 1 (A7) and 3 (B7) had higher probe densities and lanes 2 (A7) and 4 (B7) had probe density of estimated 10,000-100,000 per 1um bead. The ligation product of the capture probe to the target molecule was evaluated in a agarose gel. Probe density of approximately 10,000-100,000 per bead had better ligation efficiency than those with higher probe densities.

Example 9—Testing the Feasibility of Preparing Indexed Sequencing Libraries of CPT-DNA on Beads by Intra-Molecular Hybridization Transposomes were prepared by mixing transposons having A7' and B7' capture sequences, that are complementary to A7 and B7 capture sequences on beads, with hyperactive Tn5 transposase. High molecular weight genomic DNA is mixed with the transposomes to generate CPT-DNA. Separately, beads are prepared with immobilized oligonucleotides: P5-A7, P7-B7, or P5-A7+P7-B7, where P5 and P7 are primer binding sequences and A7 and B7 are capture sequences complementary to A7' and B7' sequences respectively. Beads comprising P5-A7 alone, P7-B7 alone, P5-A7+ P7-B7, or a mixture of P5-A7 and P7-B7 beads are treated with CPT-DNA and ligase was added to the reaction mixture to determine the efficiency of the hybridization of the immobilized oligos to the transposed DNA. The results are shown in FIG. 26. Sequencing libraries are only made when P5-A7 & P7-B7 are immobilized together on one bead (lane 4) as shown by high molecular weight bands on an agarose gel. The results indicate a high efficiency of intra-molecular hybridization and prove the feasibility of the preparing indexed sequencing libraries of CPT-DNA on beads by intra-molecular hybridization.

Example 10—Testing the Feasibility of Clonal Indexing

Several sets of transposomes were prepared. In one set, hyperactive Tn5 transposase is mixed with transposon sequences Tnp1 with 5' biotin to prepare transposome 1. In another set, Tnp2 having unique index2 with 5' biotin to prepare a transposome 2. In another set, hyperactive Tn5 transposase is mixed with transposon sequences Tnp3 with 5' biotin to for transposome 3. In another Tnp4 having

US 12,570,971 B2

Figure 27:
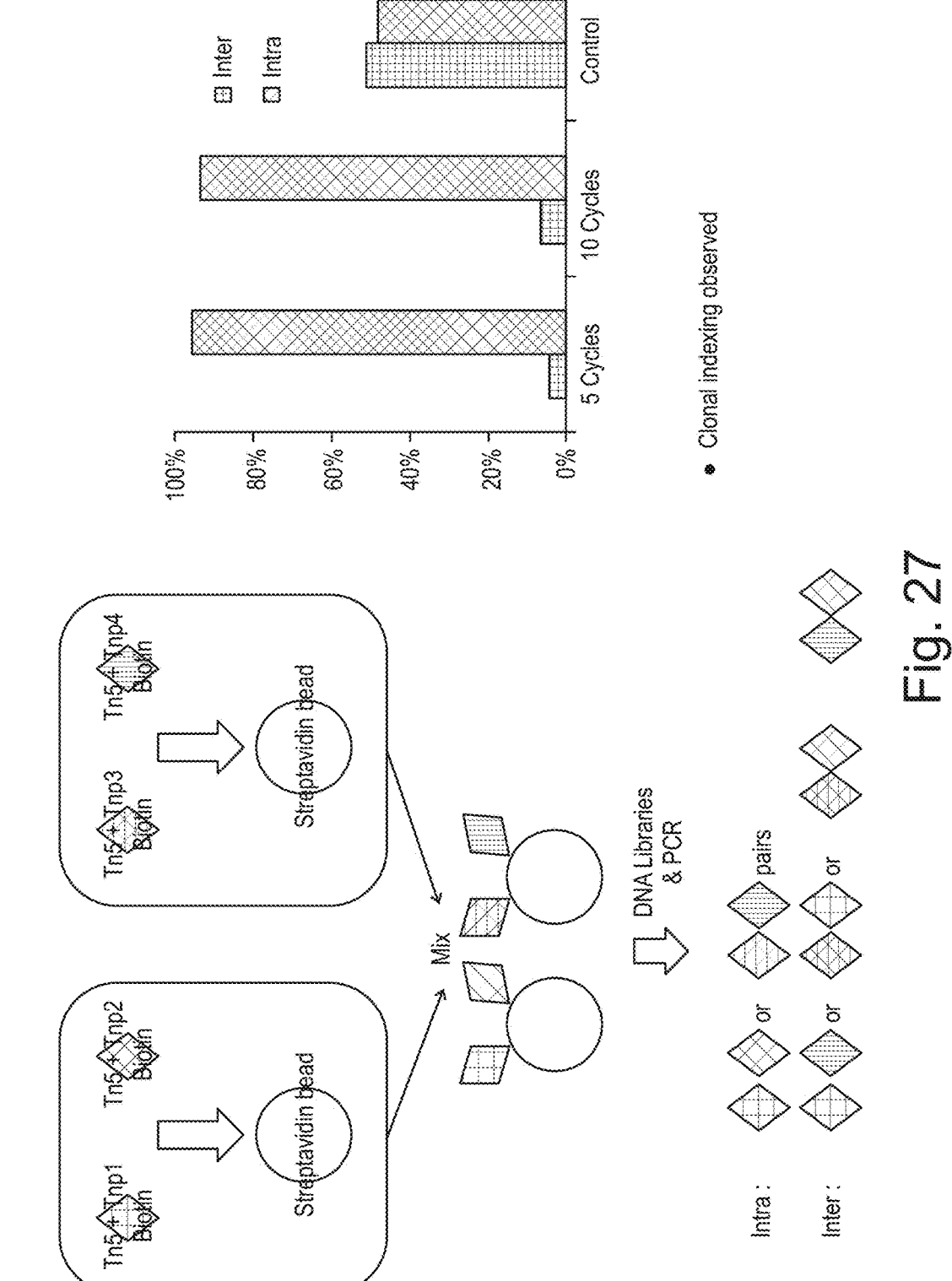
FIG. 27 shows the results of testing the feasibility of clonal indexing.
Figure 28:
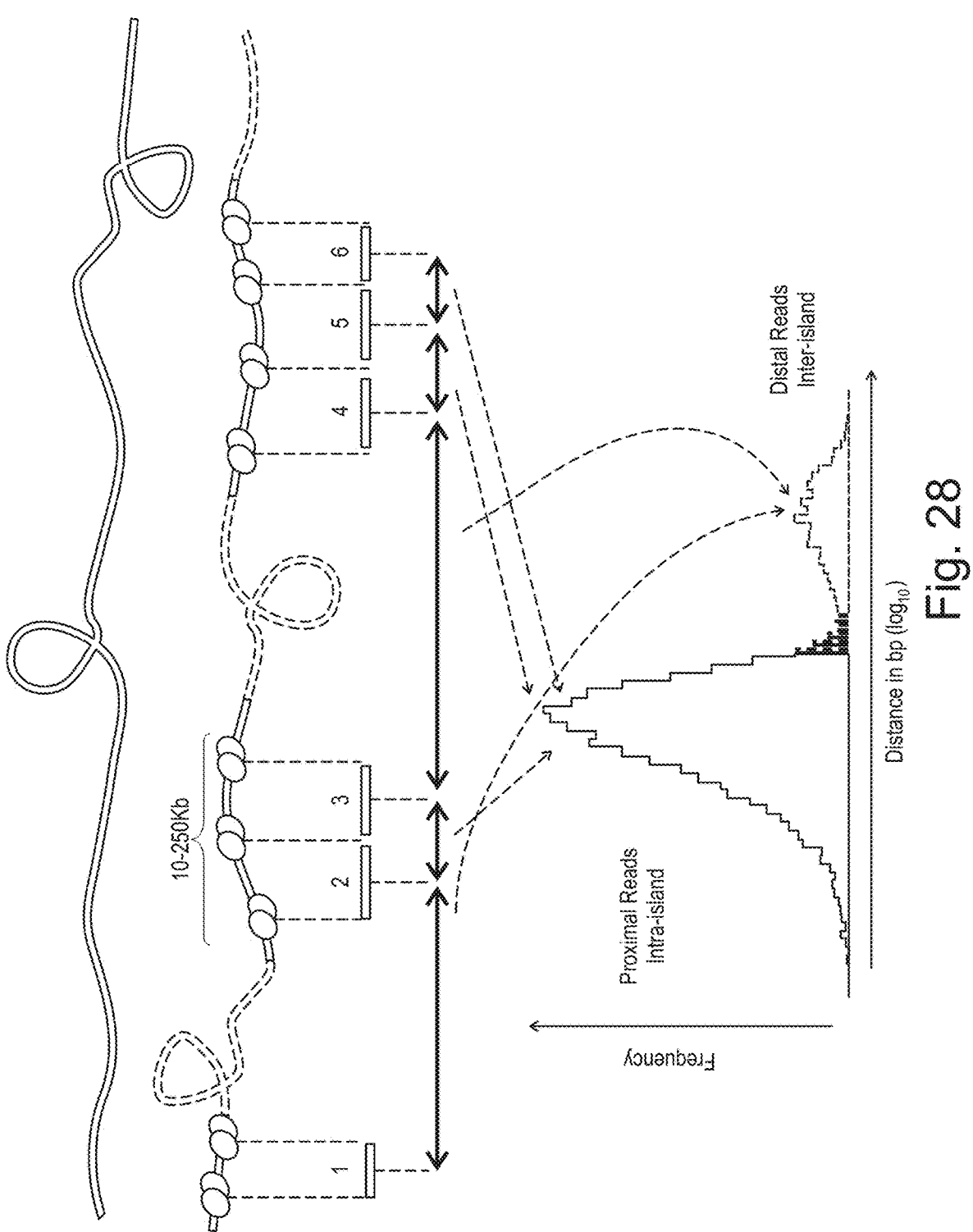
FIG. 28 depicts a graph showing the frequencies of sequencing reads for particular distances within (intra) and also between (intra) neighboring aligned islands of reads for template nucleic acid following tagmentation.

37 unique index 4 and 5'-biotin to prepare a transposome 4. Each of transposome 1&2 and transposome 3&4 are mixed separately with streptavidin beads to generate bead set 1 and bead set 2. The two set of beads are then mixed together and incubated with genomic DNA and tagmentation buffer to promote tagmentation of the genomic DNA. This is then followed by PCR amplification of the tagmented sequences. The amplified DNA is sequenced to analyze the insertion of the index sequences. If tagmentation is confined to the beads, majority of fragments will be coded with Tnp1/Tnp2 and Tnp3/Tnp4 indexes. If there is intra-molecular hybridization, the fragments may be coded with Tnp1/Tnp4, Tnp2/Tnp3, Tnp1/Tnp3, and Tnp2/Tnp4 indexes. Sequencing results after 5 and 10 cycles of PCR were shown in FIG. 27. The control has all four transposons mixed together and immobilized on a bead. Results indicate that the majority of the sequences had Tnp1/Tnp2 or Tnp3/Tnp4 indexes indicating that clonal indexing is feasible. The control shows no distinction between the indexes.

Example 11—Indexed Clonal Bead Transposition in a Single Reaction

Ninety six indexed transposome bead sets are prepared. Individual indexed transposomes were prepared by mixing transposon comprising an oligonucleotide comprising a Tn5 mosaic end sequence (ME) at the 5'-end and index sequence. Individually indexed transposomes were immobilized on beads through streptavidin-biotin interaction. Transposomes on beads were washed and all 96 individually indexed transposomes on beads were pooled. Oligonucleotides complimentary to the ME sequence and comprising an index sequence is annealed to the immobilized oligonucleotide creating transposons with unique indexes. The ninety six clonal indexed transposome bead sets are combined and incubated with high molecular weight (HMW) genomic DNA in presence of Nextera tagmentation buffer in a single tube.

The beads are washed and the transposase are removed by treating the reaction mixture with 0.1% SDS. The tagmented DNA is amplified with indexed primers and sequenced with PE HiSeq flow cell v2 using TruSeq v3 cluster kit and sequencing data are analyzed.

Figure 31:
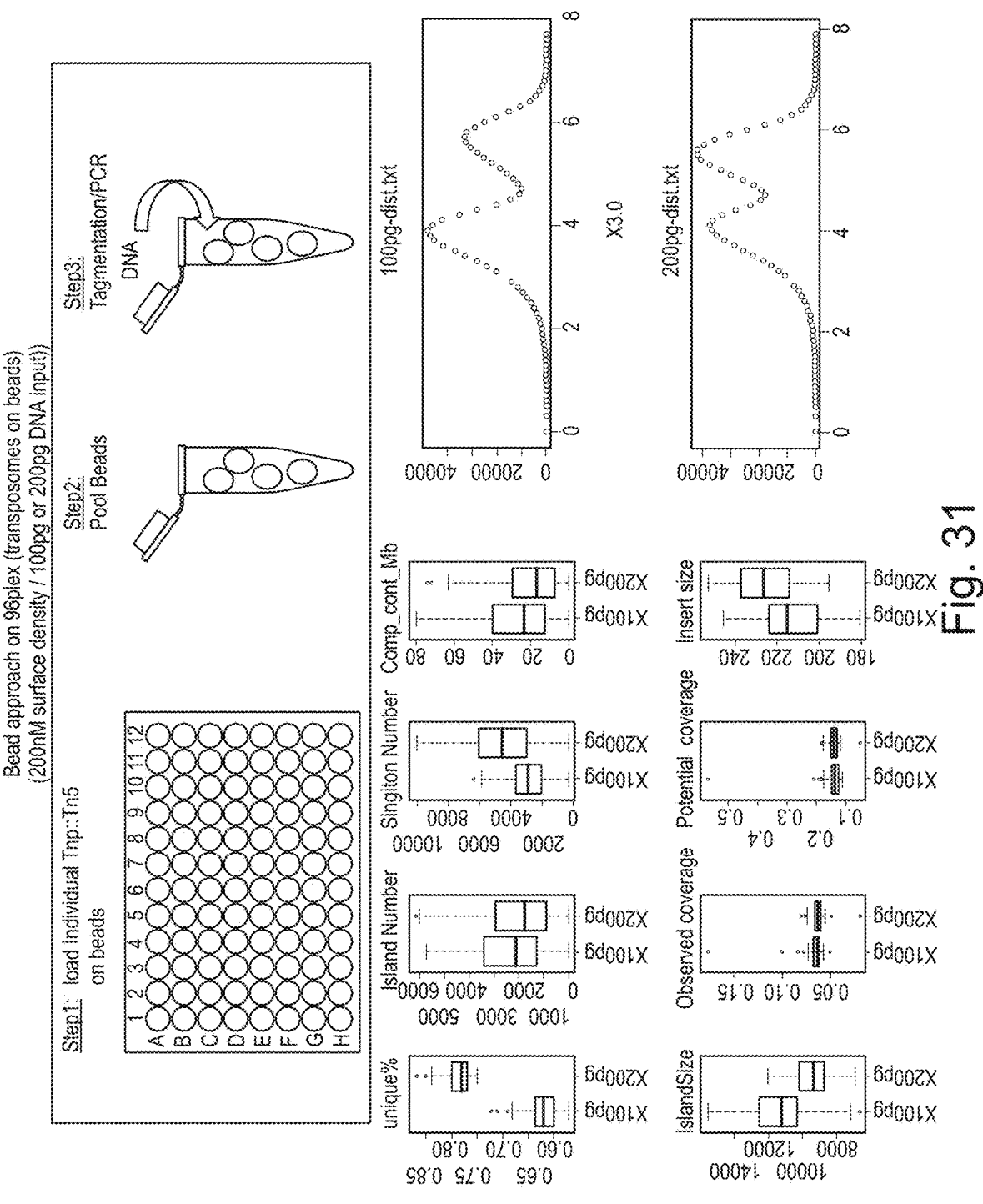

Clusters or islands of reads are observed. A plot of the nearest neighbor distances between the reads for each sequence shows essentially to major peaks, one from within the cluster (proximal) and another from between clusters (distal). A schematic of the method and the results are shown in FIGS. 30 and 31. The island sizes ranged from approximately between 3-10 kb. Percent of bases covered are approximately 5% to 10%. The insert sizes of the genomic DNA are approximately 200-300 bases.

Example 12—Library Sizes for Transposomes on Beads

Transposomes are first assembled in solution by mixing a first oligonucleotide having ME' sequence, a second oligonucleotide having ME-barcode-P5/P7 sequence, and Tn5 transposase. In first set, the first oligonucleotide having ME' sequence is biotinylated at the 3'-end. In second case the oligonucleotide having ME-barcode-P5/P7 sequence is biotinylated at the 5'-end. To various concentrations (10 nM, 50 nM, and 200 NM) of each of the resulting transposome sets streptavidin beads are added such that the transposomes are immobilized on the streptavidin beads. The beads are washed and HMW genomic DNA is added and tagmentation is carried out. In some cases, the tagmented DNA is treated with 0.1% SDS and in other cases the tagmented DNA are untreated. The tagmented DNA is PCR amplified for 5-8 cycles and sequenced. The schematic is shown in FIG. 32.

Figure 33:
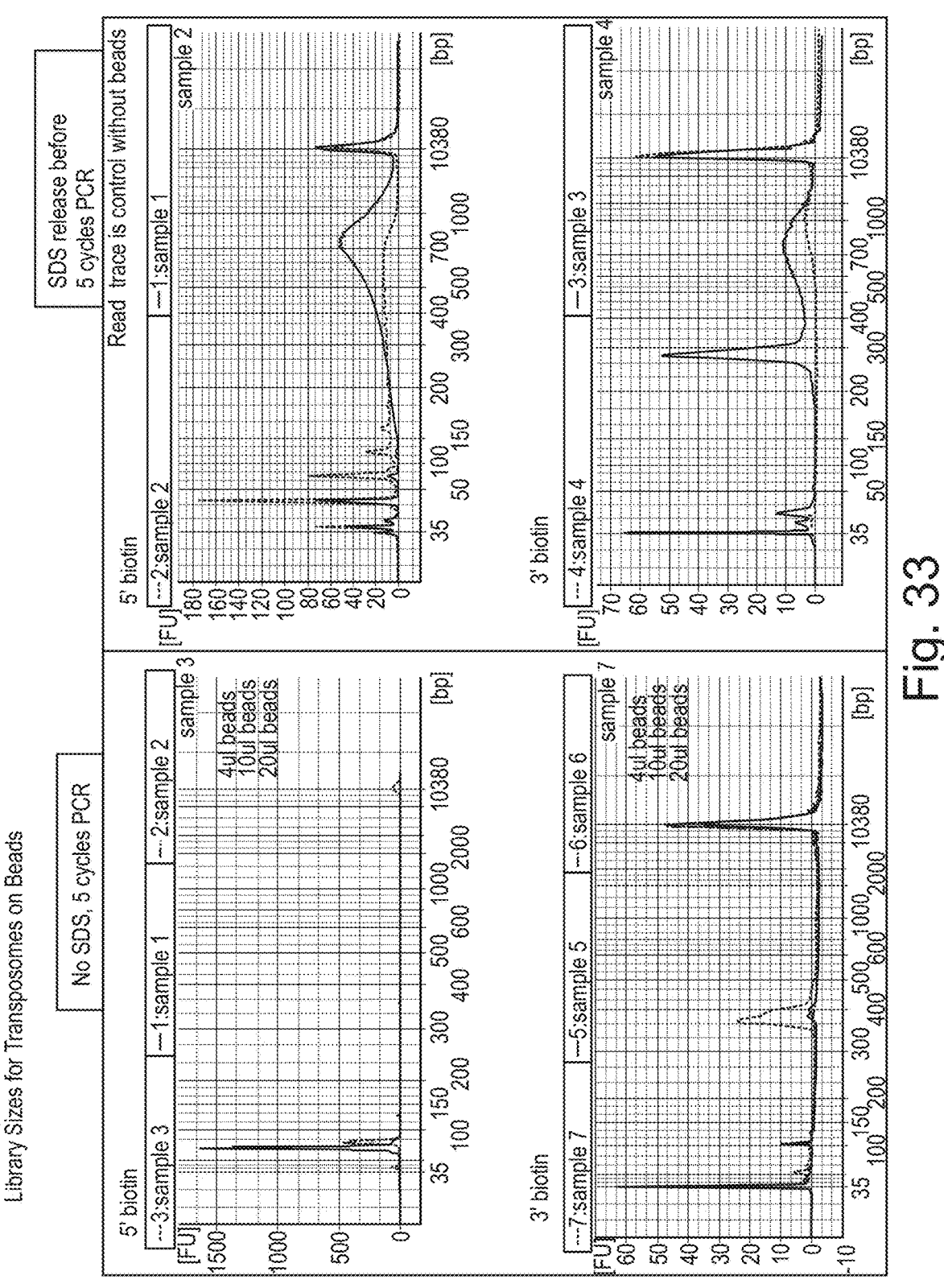
FIG. 33 shows the library sizes for transposomes on beads.
Figure 34:
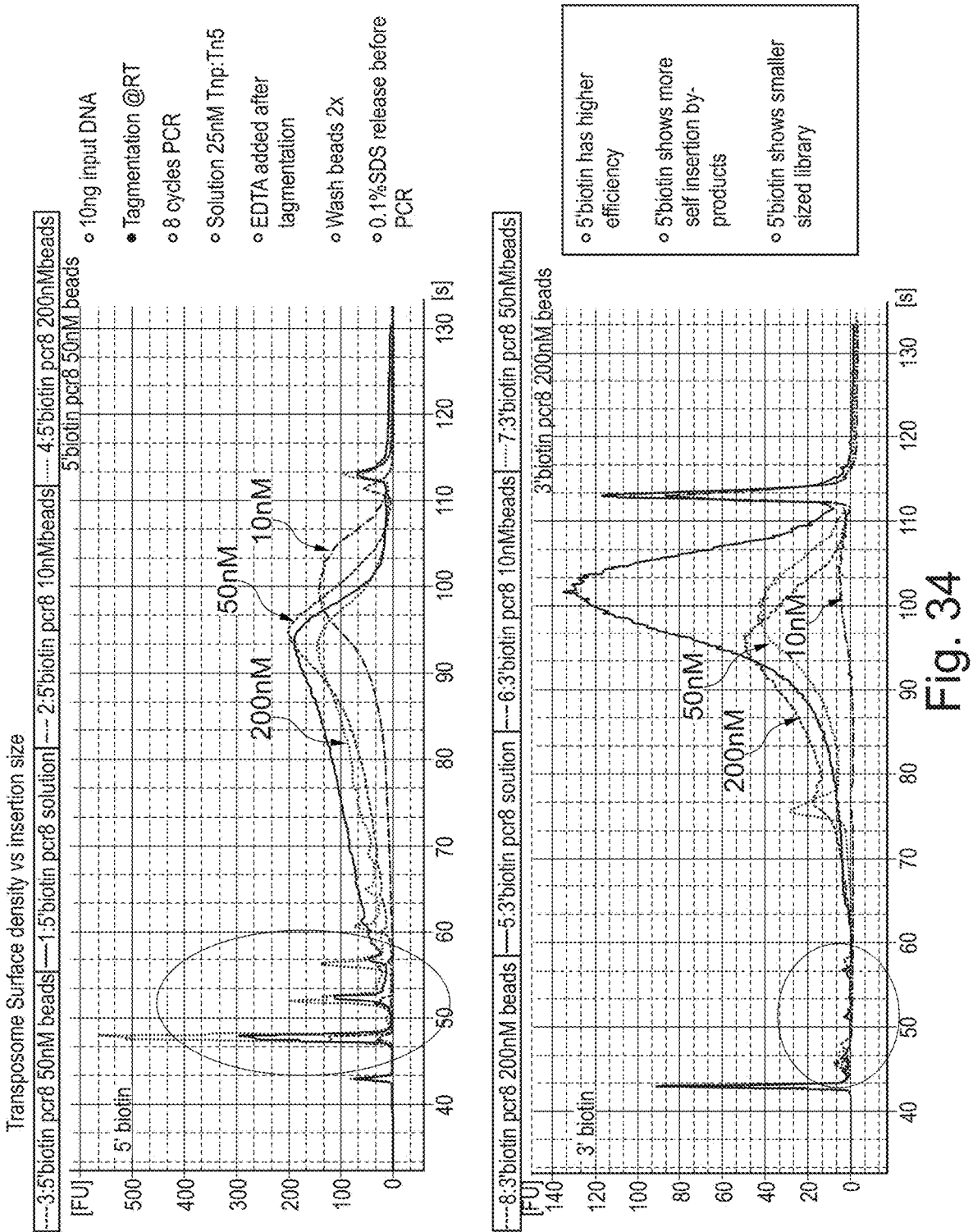
FIG. 34 shows the effect of transposome surface density on insertion size.

As shown in FIG. 33, treatment of SDS improves the amplification efficiency and sequencing quality. Oligonucleotides with 3'-biotin has better library sizes for transposomes. FIG. 34 shows the effect of transposome surface density on the insertion size.

Transposomes with 5'-biotin shows smaller sized library and more self-insertion by-products.

Example 13—Titration of Input DNA

Figure 35:
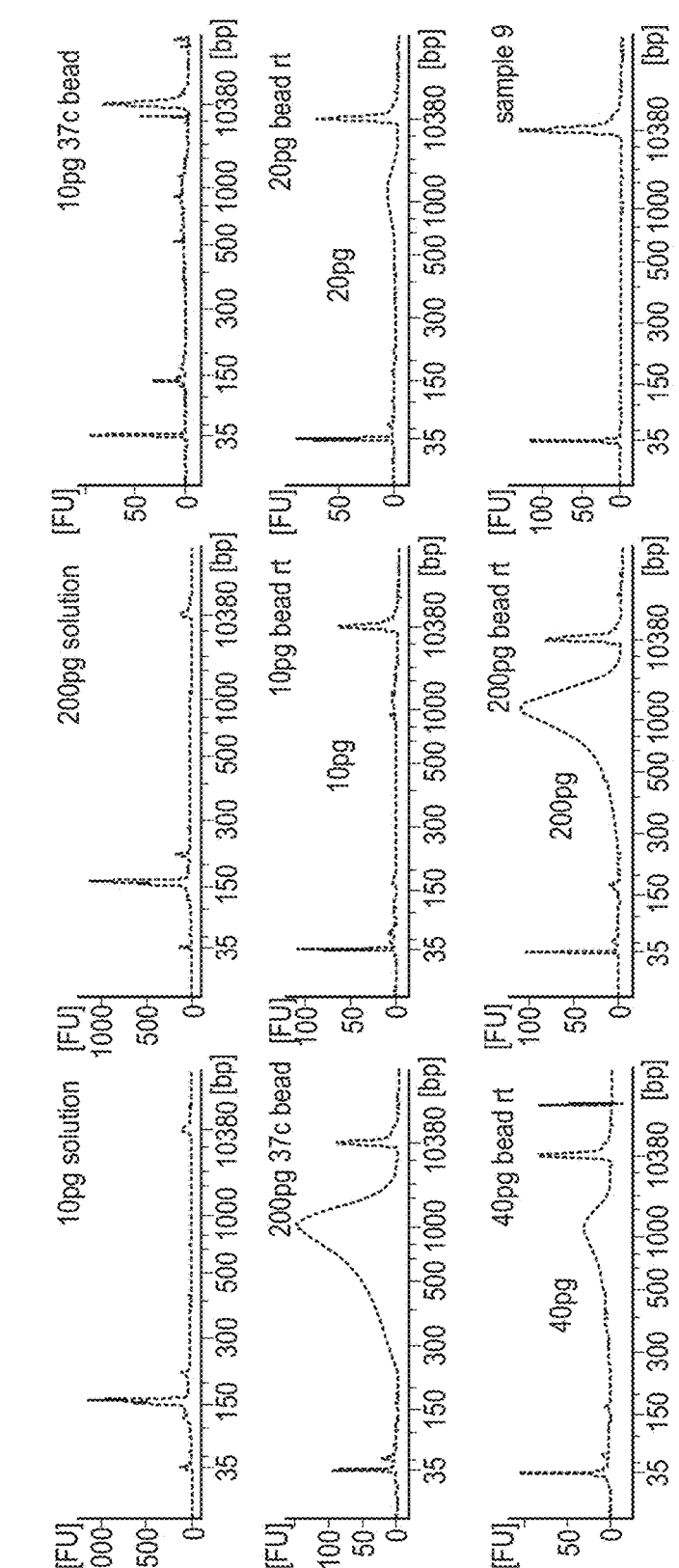
FIG. 35 shows the effect of input DNA on the size distribution.

Various amounts of target HMW DNA was added to clonally indexed beads with 50 mM Tn5: Transposon density and incubated for 15 or 60 min at 37 degree C. or for 60 min at room temperature. The transposomes comprised oligonucleotides with 3'-biotin. The tagmentation was carried out, the reaction mixture was treated with 0.1% SDS, and PCR amplified. The amplified DNA was sequenced. FIG. 35 shows the effect of input DNA on the size distribution. Reactions with 10 pg of input DNA showed the least signal. Size distribution pattern was similar for DNA inputs ranging from 20, 40, and 200 pg.

Example 14—Island Size and Distribution Using Solution Based and Bead Based Methods Island size and distribution using solution based and bead based methods are compared. In a solution based approach, 96 transposomes each with unique index in the transposons are assembled in a 96 well plate. HMW genomic DNA is added, and the tagmentation reaction is carried out. The reaction product is treated with 0.1% SDS and PCR amplified. The amplified products were sequenced.

In a bead based approach, 96 transposomes each with unique index in the transposons are assembled in a 96 well plate. The oligonucleotides comprised 3'-end biotin. Streptavidin beads are added to each of the 96 well plate and incubated such that the transposomes are immobilized on the streptavidin beads. The beads are individually washed and pooled, HMW genomic DNA is added, and the tagmentation reaction is carried out in a single reaction vessel (one pot). The reaction product is treated with 0.1% SDS and PCR amplified. The amplified products were sequenced.

In the negative control, all 96 transposon sequences, each with unique index, are mixed together first. The oligonucleotides comprised 3'-end biotin. Transposomes are prepared from the individually mixed indexed transposons. Streptavidin beads are added to the mixture. HMW genomic DNA is added, and the tagmentation reaction is carried out. The reaction product is treated with 0.1% SDS and PCR amplified. The amplified products were sequenced.

Figure 36:
FIG. 36 shows the island size and distribution using bead based and solution based tagmentation reactions.
Figure 37:
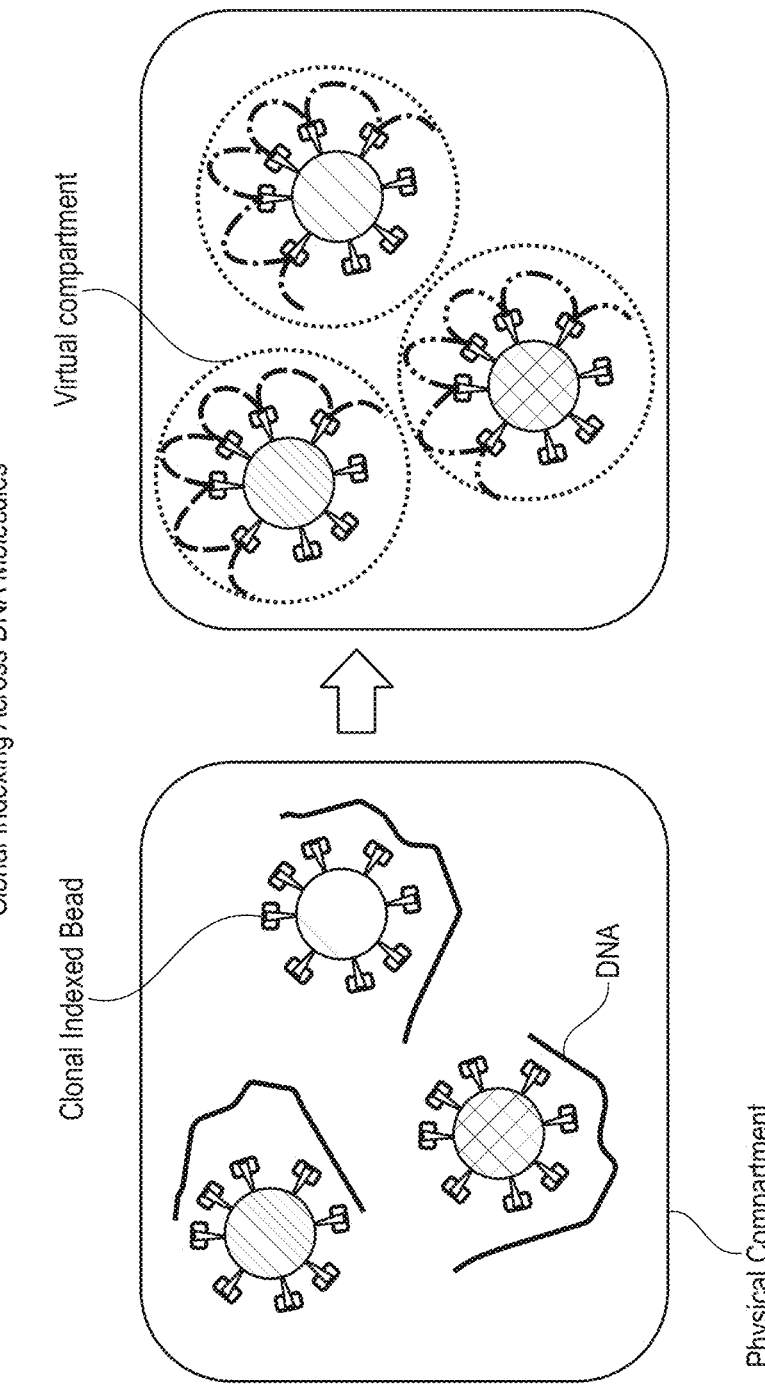
FIG. 37 shows clonal indexing of several individual DNA molecules, each receiving unique indexes.
Figure 38:
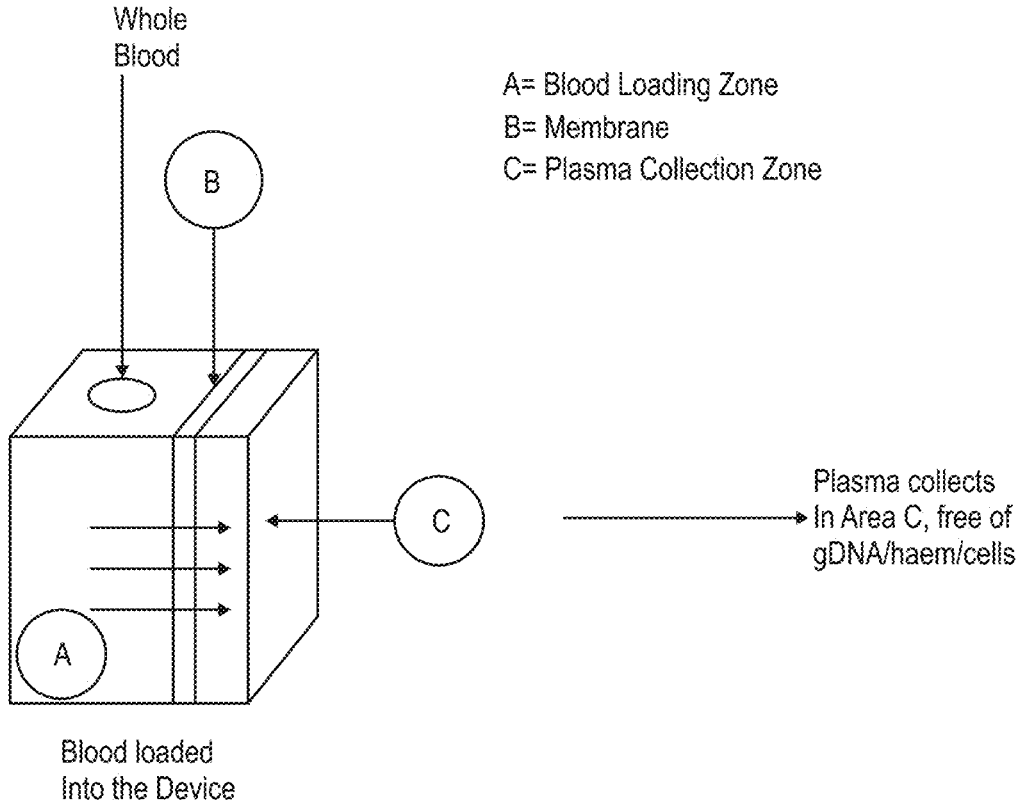
FIG. 38 shows a diagram of a device for separating plasma from whole blood.
Figure 39:
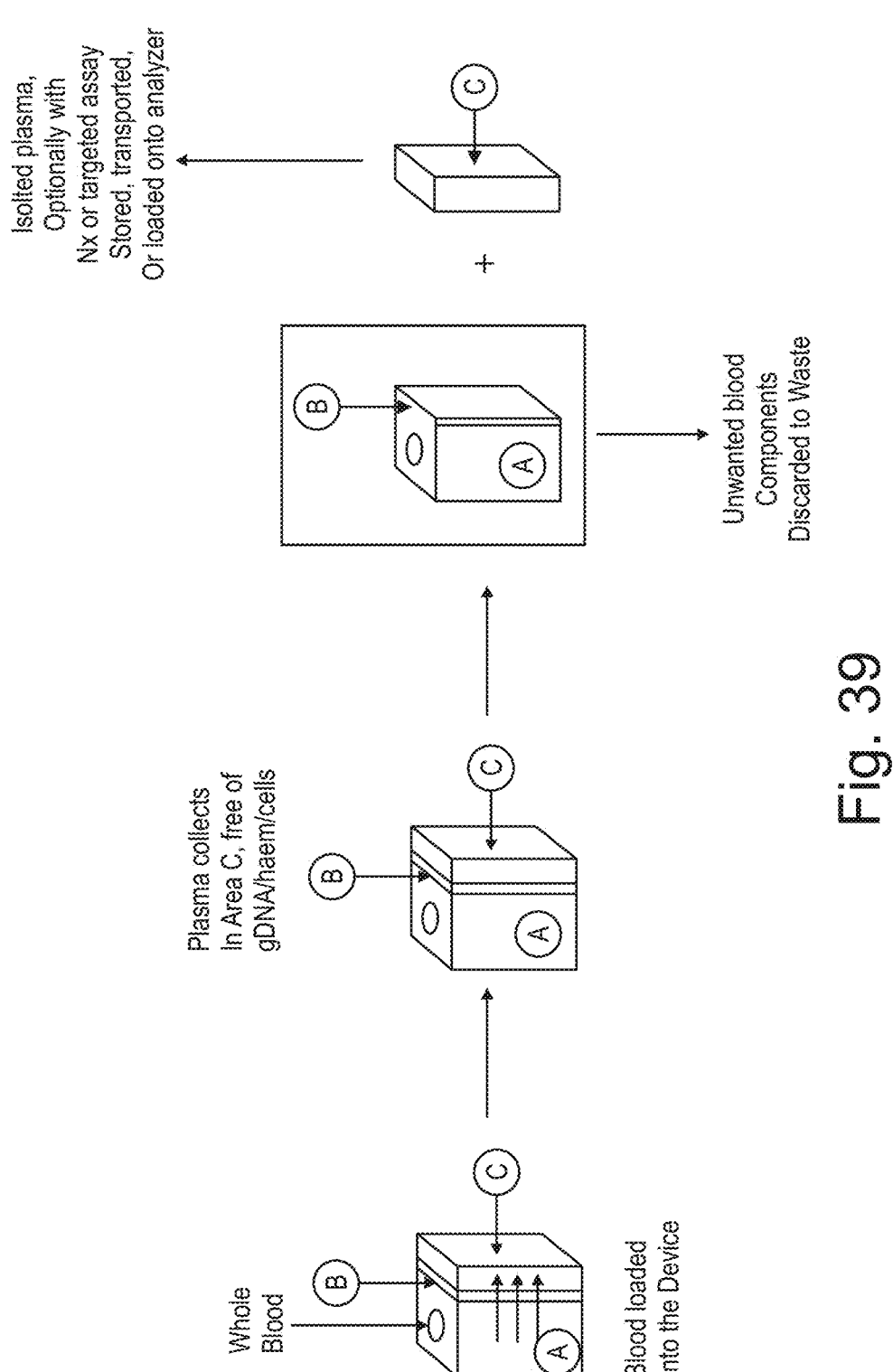
FIGS. 39 and 40 show a diagram of a device for separating plasma and subsequent use of the separated plasma.
Figure 40:
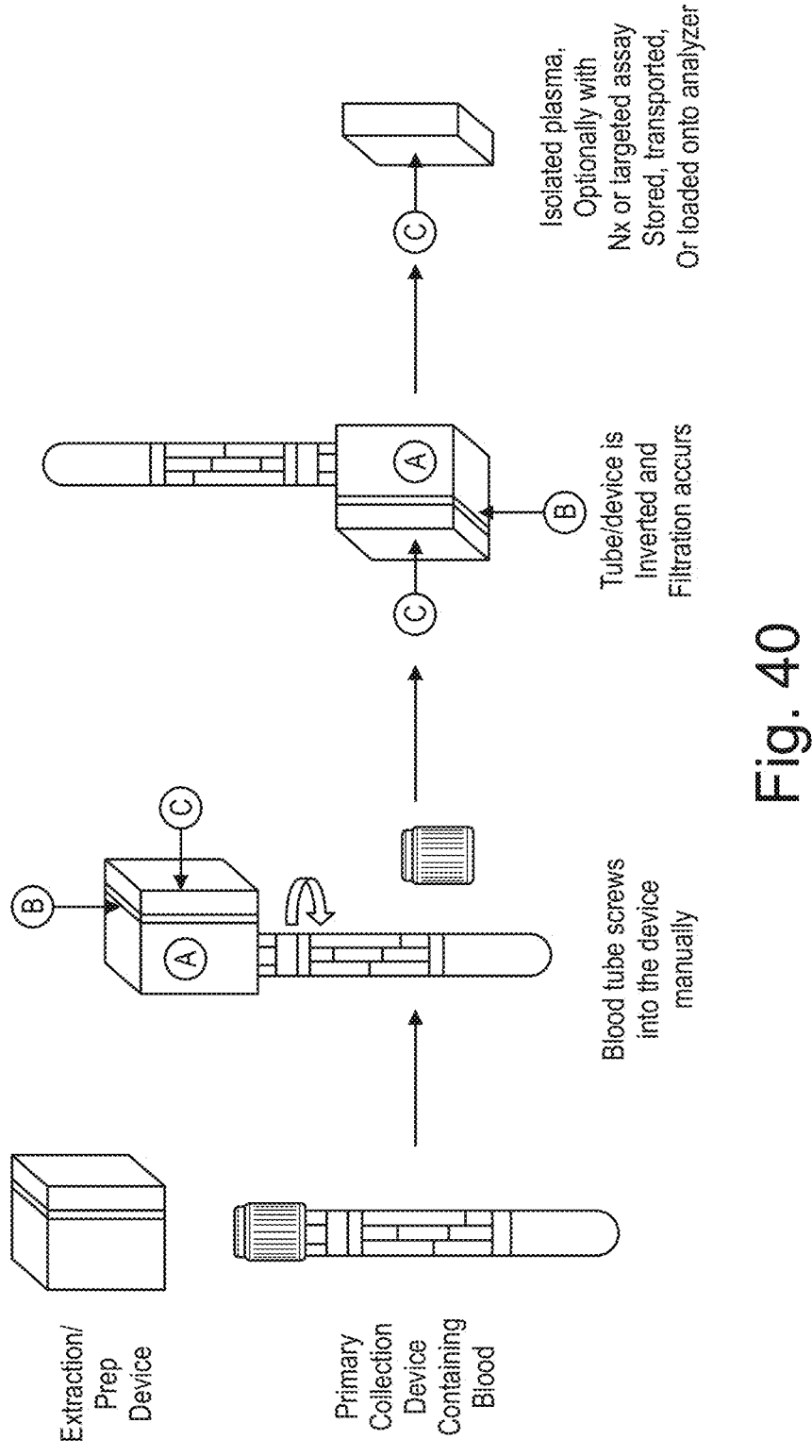

The number of intra island reads is plotted versus the island size. The results as shown in FIG. 36 indicate that islands (proximity reads) are observed with the one-pot clonal indexed beads, similar to the solution based method. When indexed transposons were mixed before transposome formation, no island (proximity reads) were observed. Mixing transposons before transposome formation gives beads with different indexes/transposomes per bead, i.e. not clonal.

Example 15—Structural Variant Analysis with CPT-Seq

Detection of 60 kb Heterozygous Deletion

Figure 47A:
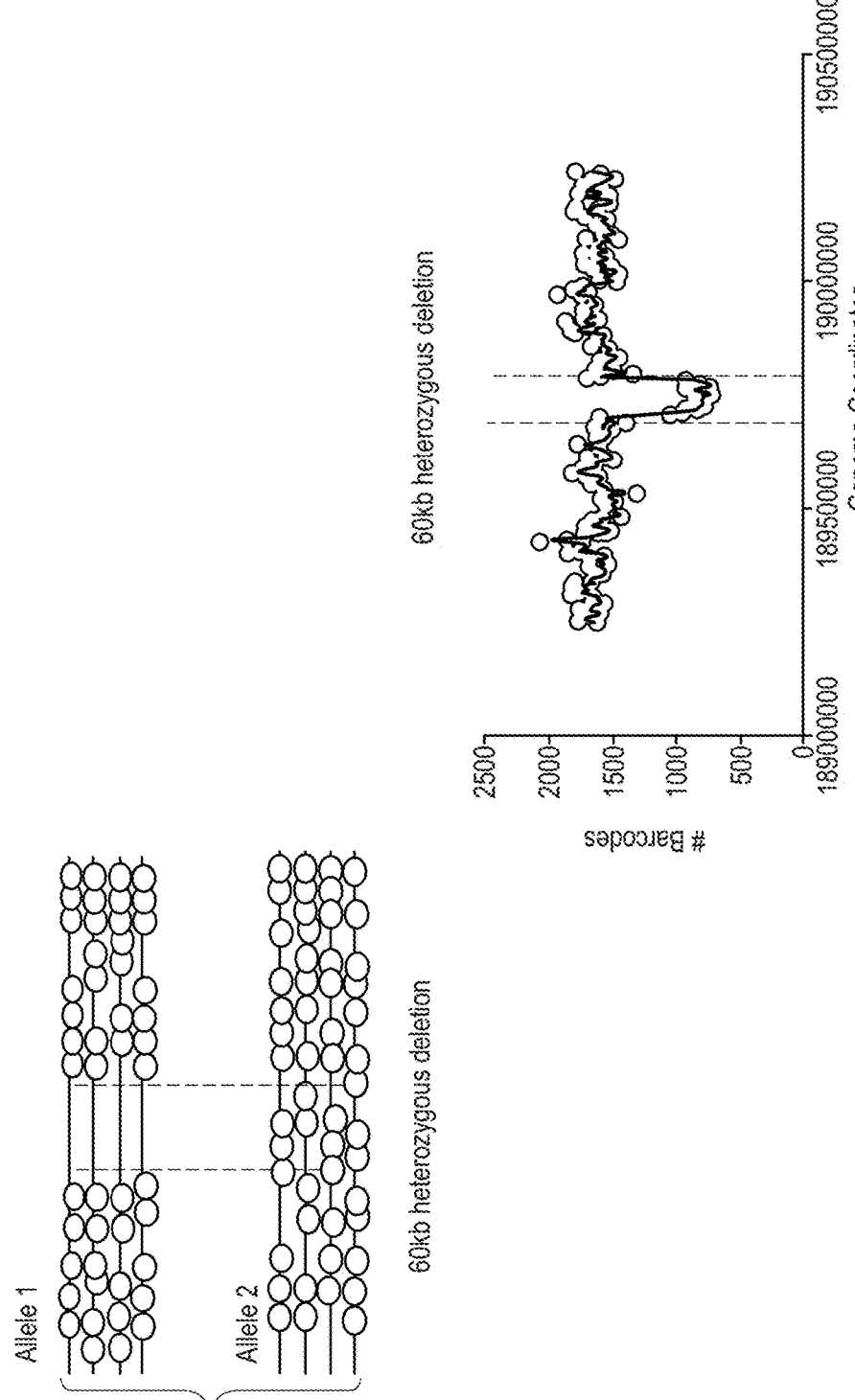
FIGS. 47A and 47B show the result of detection of 60 kb heterozygous deletion in chromosome 1.
Figure 47B:
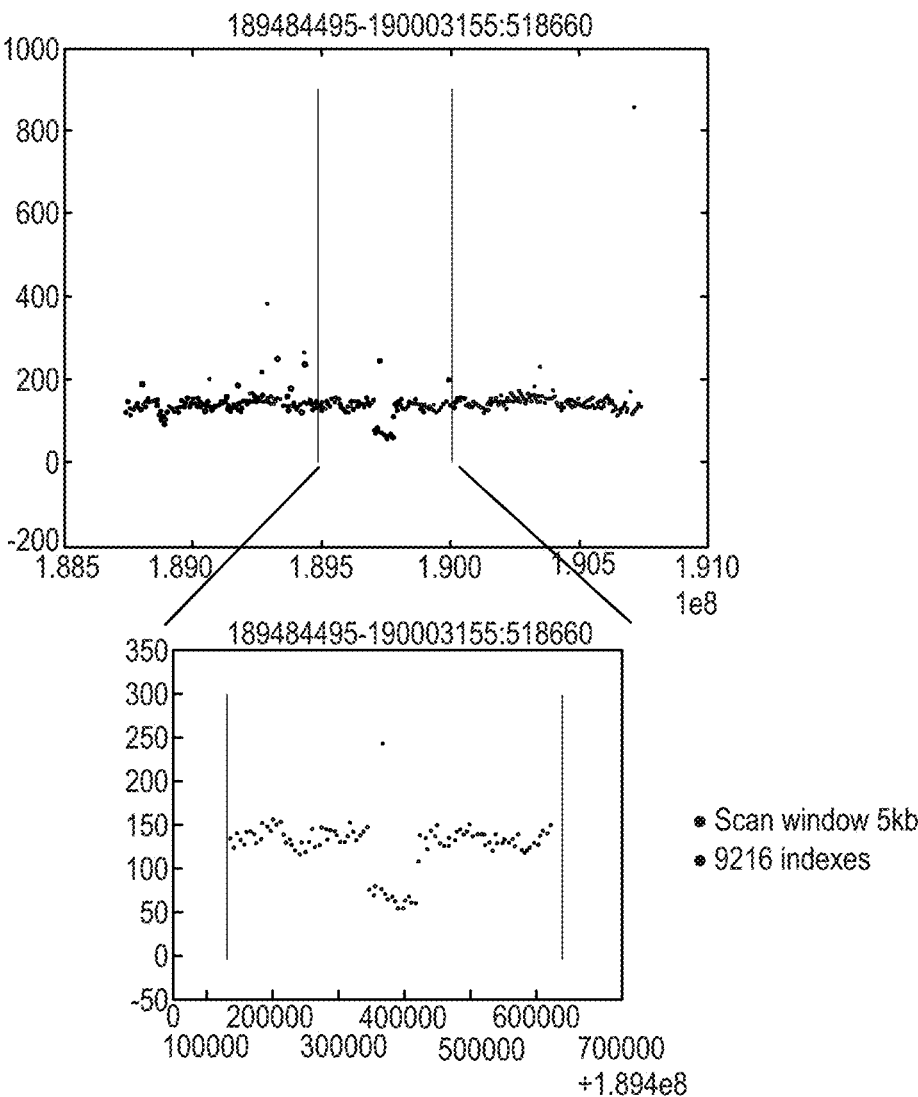

The sequencing data are extracted as fastq files and go through the demultiplexing process to generate individual fastq file for each barcode. The fastq files from the CPT sequencing are demultiplexed according to their indexes and aligned to the reference genome with the duplicates removed. The chromosomes are scanned by 5 kb/1 kb window, in which the number of the indexes showing any reads within the scanning window is recorded. Statistically for heterozygous deletion region only half amount of DNA is available for the library generation compared to its neighboring regions, therefore the number of indexes should be roughly half as its neighbors' as well. The NA12878 chr1 60 kb heterozygous deletion are shown in FIGS. 47A and 47B by scanning in 5 kb window from 9216 indexed CPT sequencing data.

Detection of Gene Fusion

Figure 48:
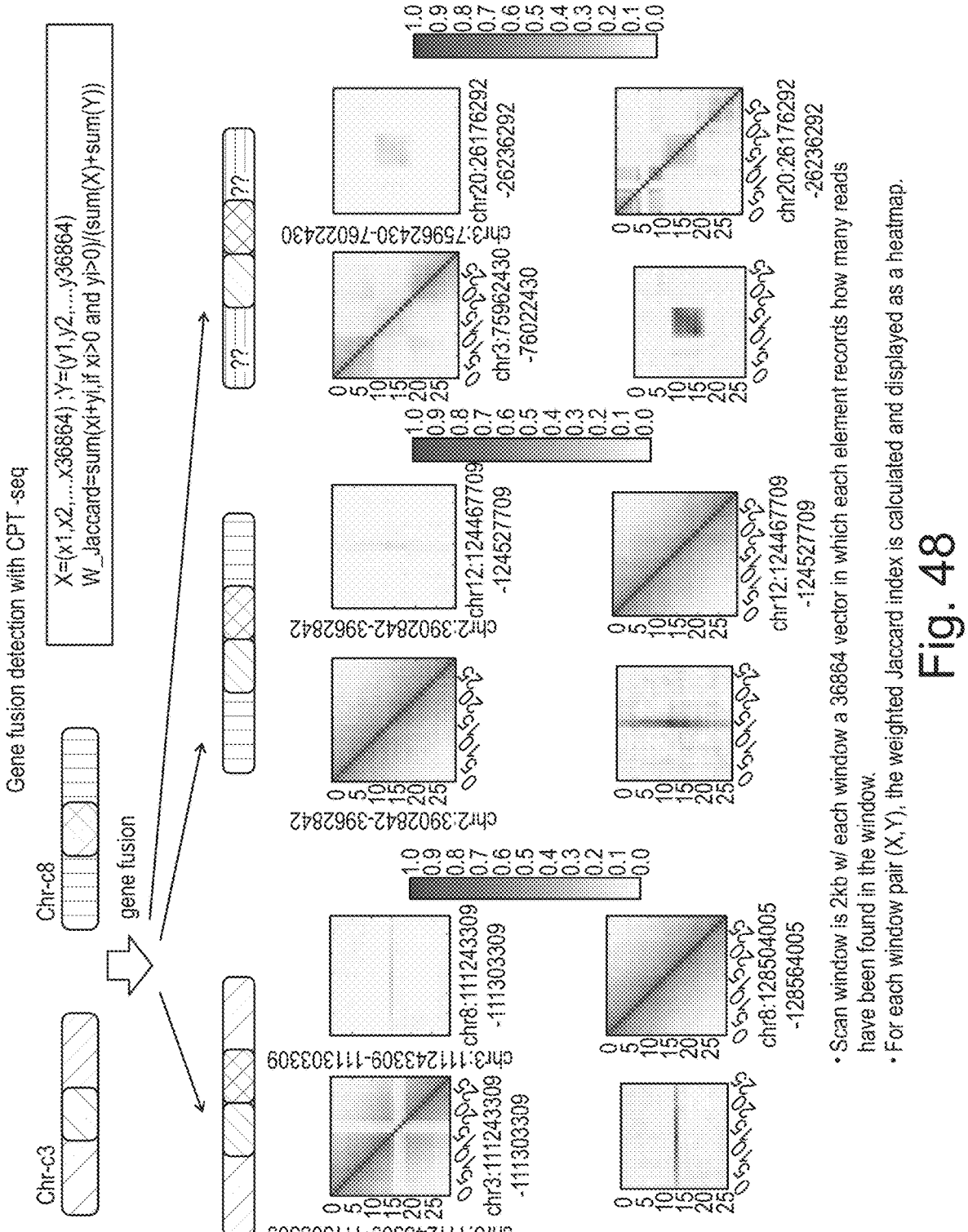
FIG. 48 shows results of detection of gene fusion using the methods of the present application.

The fastq files from the CPT sequencing are demultiplexed according to their index and aligned to the reference genome with the duplicates removed. Chromosomes are scanned in 2 kb window. Each 2 kb window is a 36864 vector in which each element records how many reads from a unique index have been found in this 2 kb window. For every 2 kb window pair (X,Y) across the genome, the weighted-Jaccard index is calculated. This index indicates the de facto distance between (X,Y) in the sample. Those indexes are displayed as the heatmap shown in FIG. 48, each data point representing a pair of 2 kb scanning window; the top left square is for X,Y both from region1, bottom right is for X,Y both from region2 and top right is for the X,Y from region1 cross region2. The gene fusion signal is revealed as the horizontal line in the middle in this case.

Detection of Deletions

Figure 49:
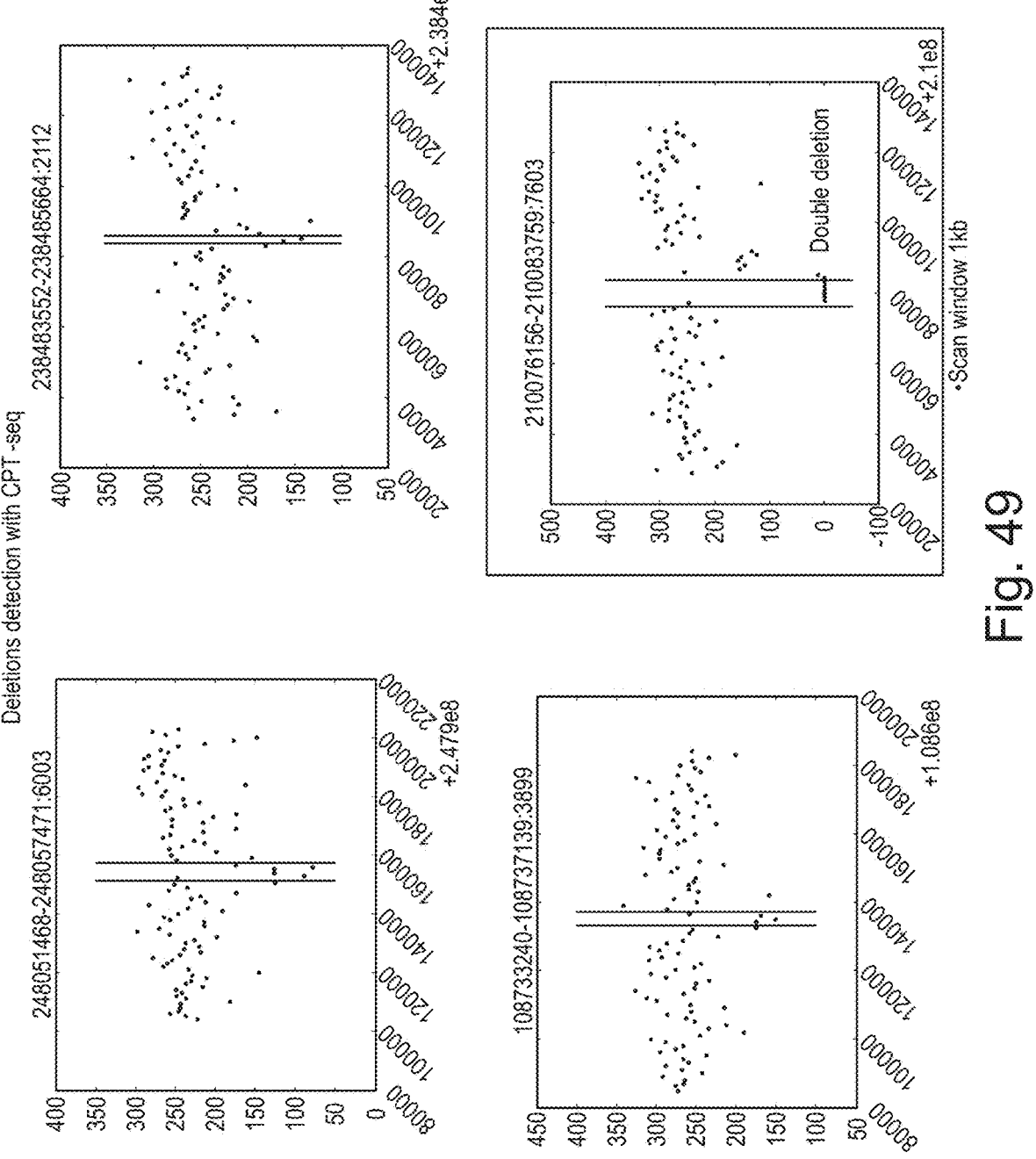
FIG. 49 shows results of detection of genetic deletions using the methods of the present application.

The fastq files from the CPT sequencing are demultiplexed according to their index and aligned to the reference genome with the duplicates removed. Chromosomes are scanned in 1 kb window. FIG. 49 shows results of detection of genetic deletions.

Example 16—Phasing and Methylation Detection

Bisulfite Conversion Efficiency Optimization Conversion was assessed at the ME (mosaic element region) and gDNA region for index linked CPT-Seq libraries on beads. Promega's MethylEdge Bisulfite Conversion system was optimized to improve efficiency.

| Cond | DNA | Beads | BSC Treatment |
|---|---|---|---|
| 1 | 10 ng | No | 1 hr @ 60 °C./0.3M NaOH |
| 2 | 10 ng | Yes | 1 hr @ 60 °C./0.3M NaOH |
| 3 | 10 ng | Yes | 1 hr @ 60 °C./1M NaOH |
| 4 | 10 ng | Yes | 1 hr @ 65 °C./0.3M NaOH |

Figure 51:
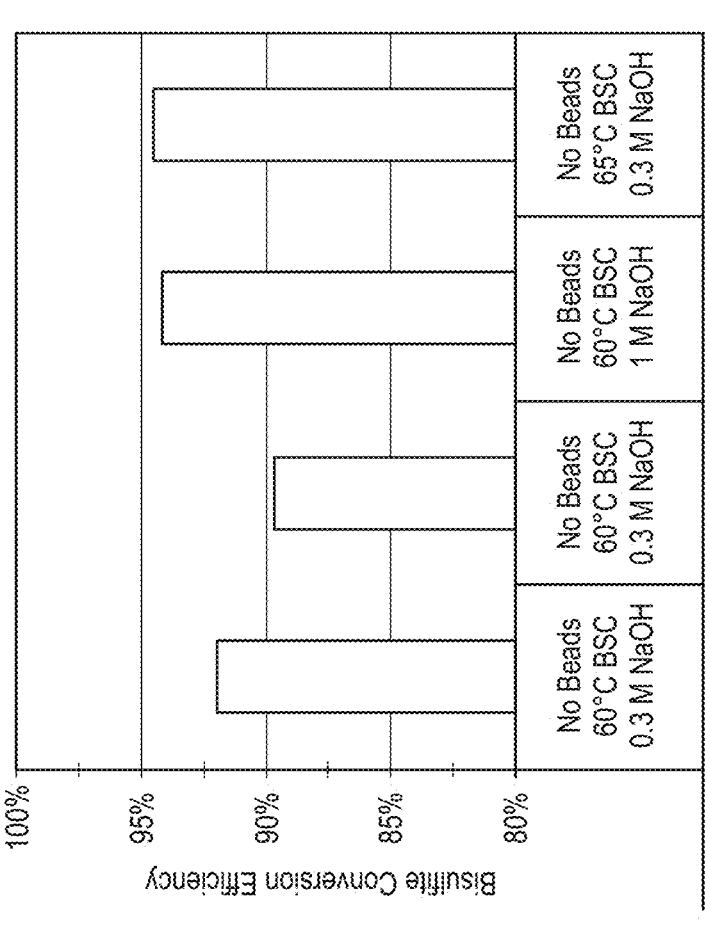
FIG. 51 shows the results of bisulfite conversion efficiency optimization.

ME sequences were analyzed to determine efficiency of bisulfite conversion treatments and shown in FIG. 50. 95% bisulfite conversion (BSC) of indexed-linked libraries attached to beads. Similar PCR yields observed between bisulfite conditions>Harsher bisulfite treatment did not appear to degrade libraries and shown in FIG. 51. Approximately 95% BSC of indexed linked libraries on beads were observed. Variables investigated to improve BSC (C's→U's) were temperature and NaOH concentration (denaturation). 60° C. and 1M NaOH or ° C. and 0.3 M NaOH performed well.

Figure 52:
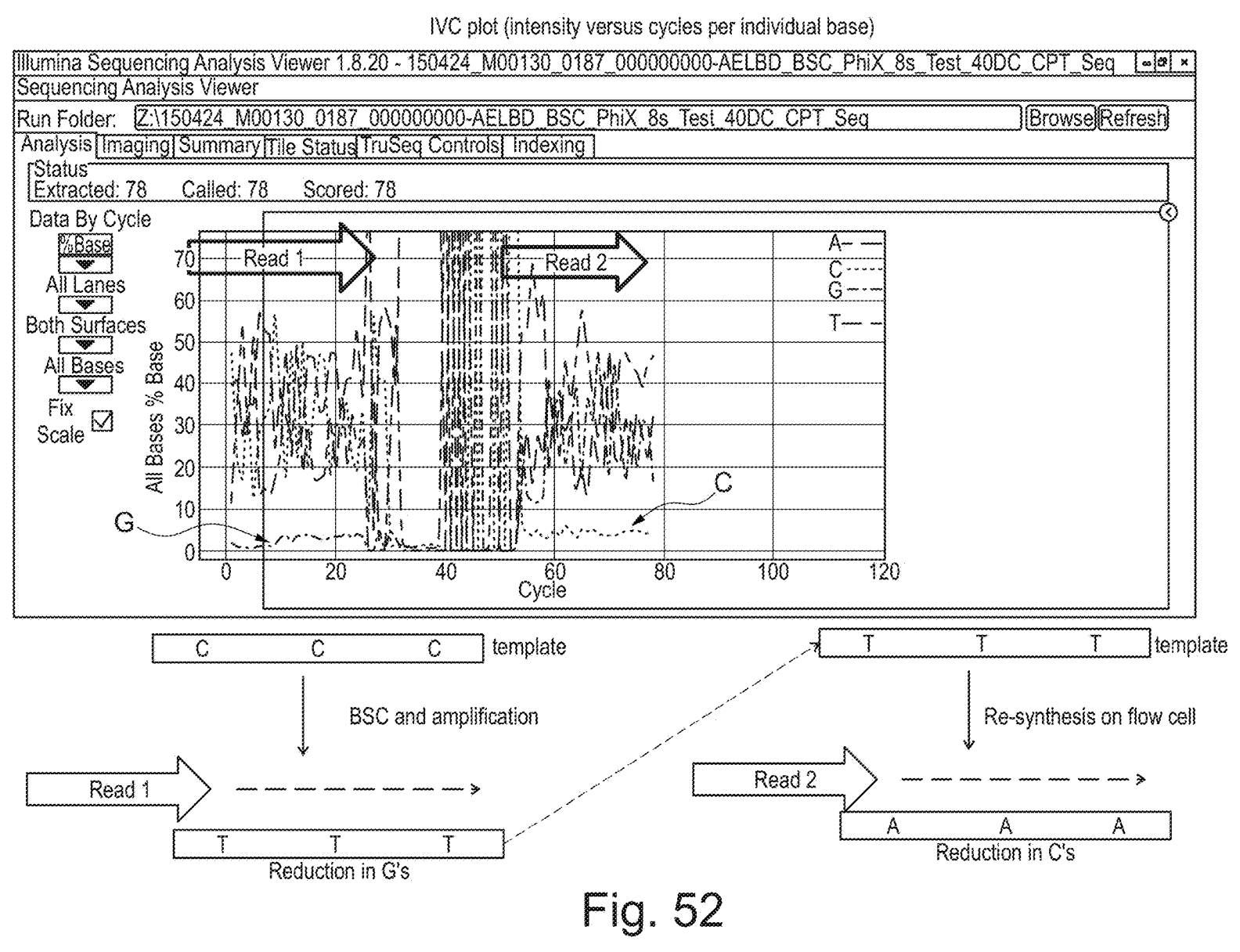

Expected sequencing read structure after sequencing BSC converted CPT-seq on beads libraries observed. Percent base metrics displayed with the IVC plot in FIG. 52.

Figure 53:
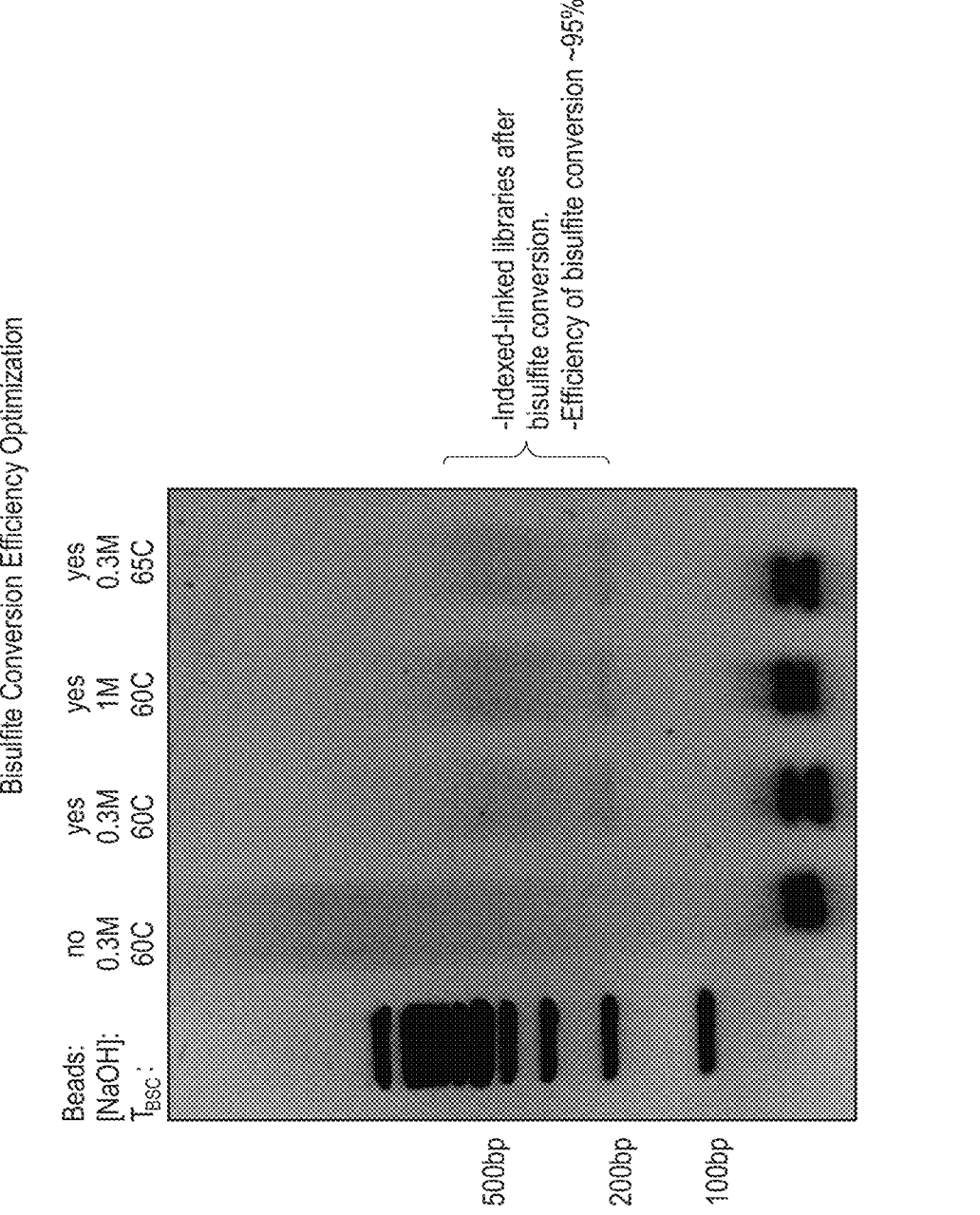
FIG. 53 shows an image of agarose gel electrophoresis of indexed-linked libraries after PCR after BSC.

FIG. 53 shows an image of agarose gel electrophoresis of indexed-linked libraries after PCR after bisulfite conversion. The expected size-range of 200-500 bp libraries was observed. Reaction without DNA does not yield indexed-linked libraries.

Example 17—Targeted Phasing

Figure 54:
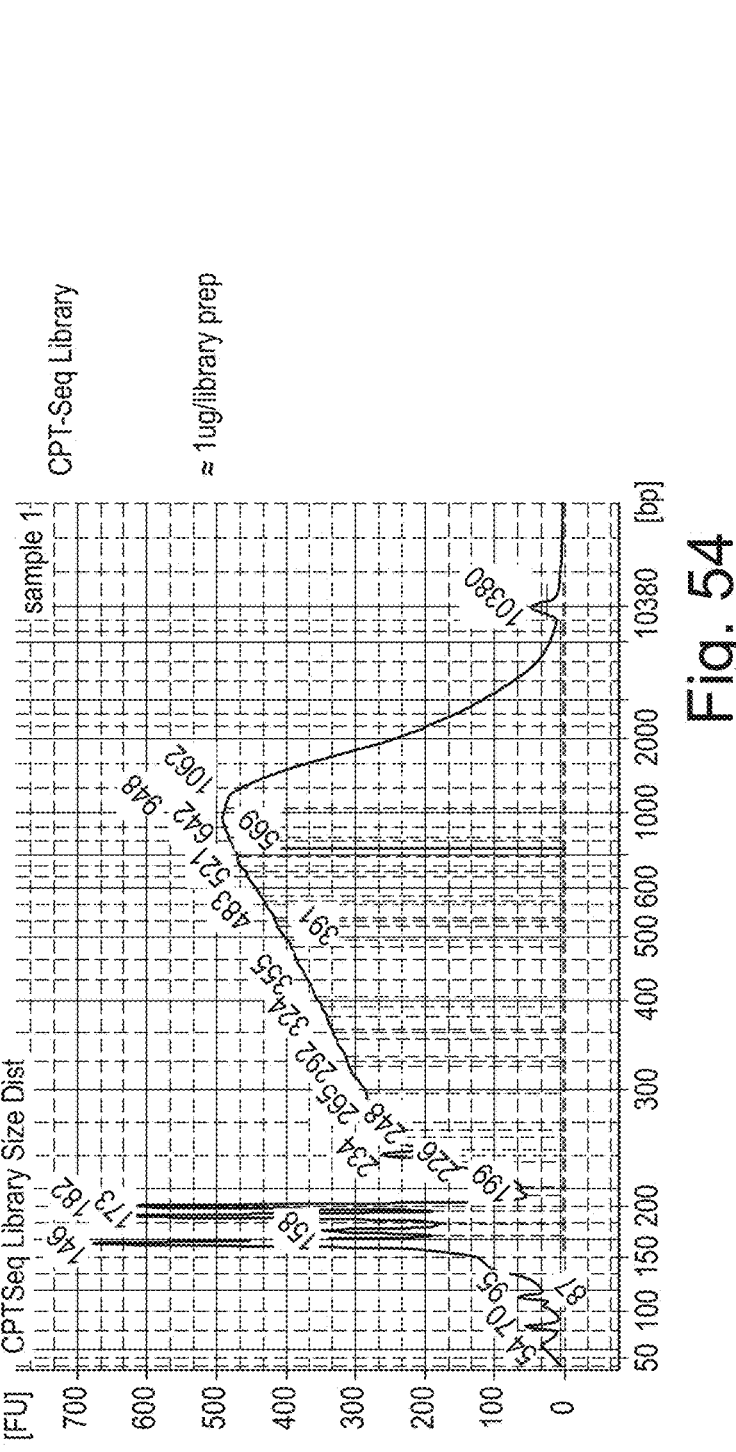
FIG. 54 shows the bioanalyzer trace of whole-genome indexed linked CPT-seq libraries before enrichment without size-selection.
Figure 55:
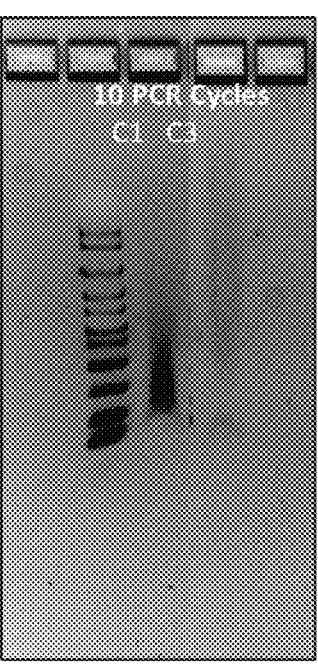
FIG. 55 shows the agarose gel analysis of libraries after enrichment.

Whole-genome indexed linked CPT-seq libraries were enriched. FIG. 54 the bioanalyzer trace of whole-genome indexed linked CPT-seq libraries before enrichment without size-selection. FIG. 55 shows the agarose gel analysis of libraries after enrichment.

Enrichment statistics for HLA region is shown below:

| Sample ID | C3 |
|---|---|
| Sample Name: | HLA Probes |
| Padding size: | 150 |
| Total length of targeted reference: | 5062748 |
| Total PF reads: | 2516 |
| Percent Q30 | 94.90% |
| Total aligned reads: | 2498 |
| Percent aligned reads: | 99.40% |
| Targeted aligned reads: | 840 |
| Read enrichment: | 30.80% |
| Percent duplicate paired reads: | 12.70% |
| Fragment length median: | 195 |

Figure 56:
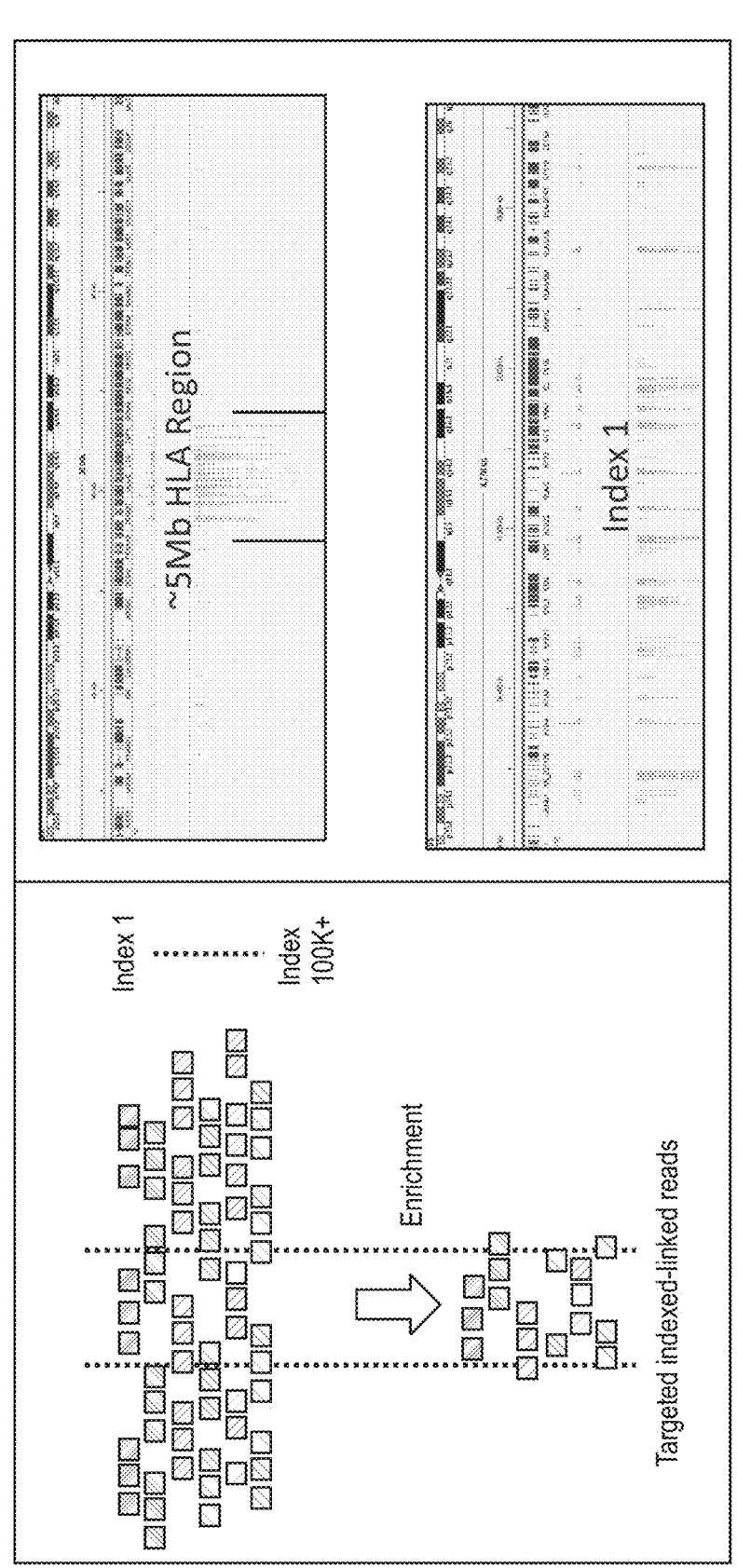
FIG. 56 shows the results of application of targeted haplotyping to the HLA region in the chromosome.

FIG. 56 shows the results of application of targeted haplotyping to the HLA region in the chromosome. Illustration of enrichment of whole genome indexed linked read library in the left. Each small bar represents an indexed short library. Clusters of indexed libraries are "islands", the region that got clonally indexed on a single bead with the same index, hence the proximity of the reads ("island" character) on a genomic scale. Enrichment (see Selective enrichment of nucleic acids WO 2012108864 A1) of libraries in the targeted region are displayed on the right. Reads are enriched for the HLA region. Additionally, when reads are sorted by index and aligned to the genome they again display the "island" structure indicating that contiguity information is maintained from the indexed linked reads.

Example 18—Index Exchange

To evaluate the exchange of the mosaic ends (ME) of transposome complexes, bead with different indices were prepared. After mixing, index exchange was determined by sequencing the libraries and reporting the indices for each library. % "swapped" was calculated as (D4+D5+E3+E5+f4)/(sum of all 96) and shown in the FIG. 65.

Figure 66:
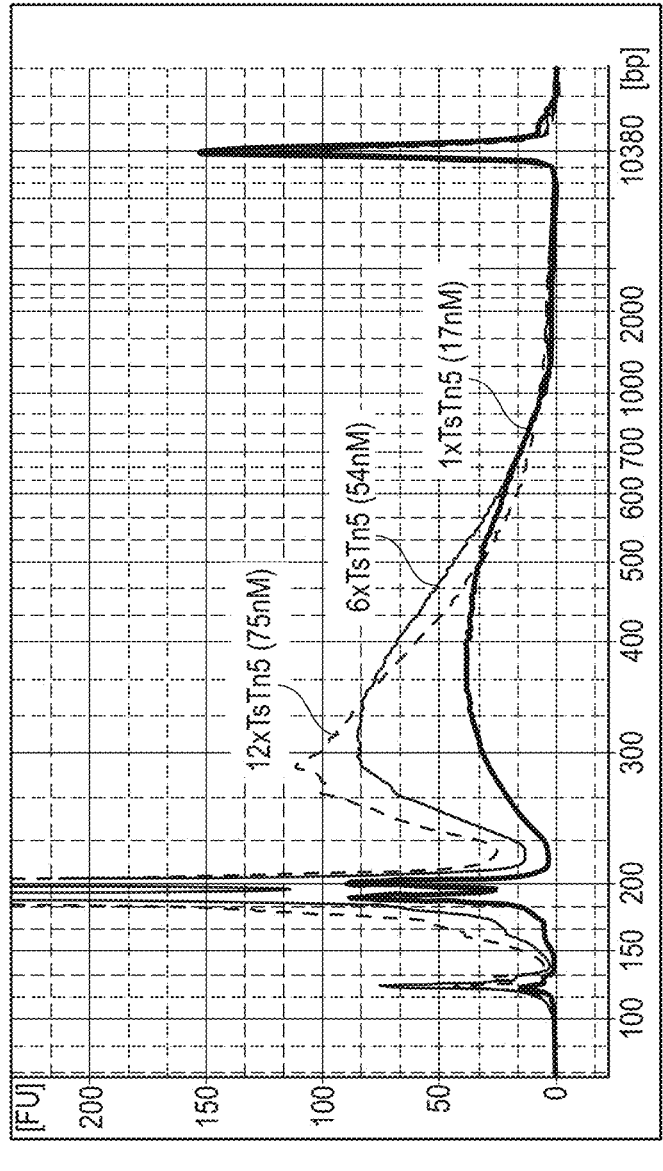
FIG. 66 shows Agilent BioAnalyzer analysis of fragment sizes of Ts-Tn5 titration.
Figure 67:
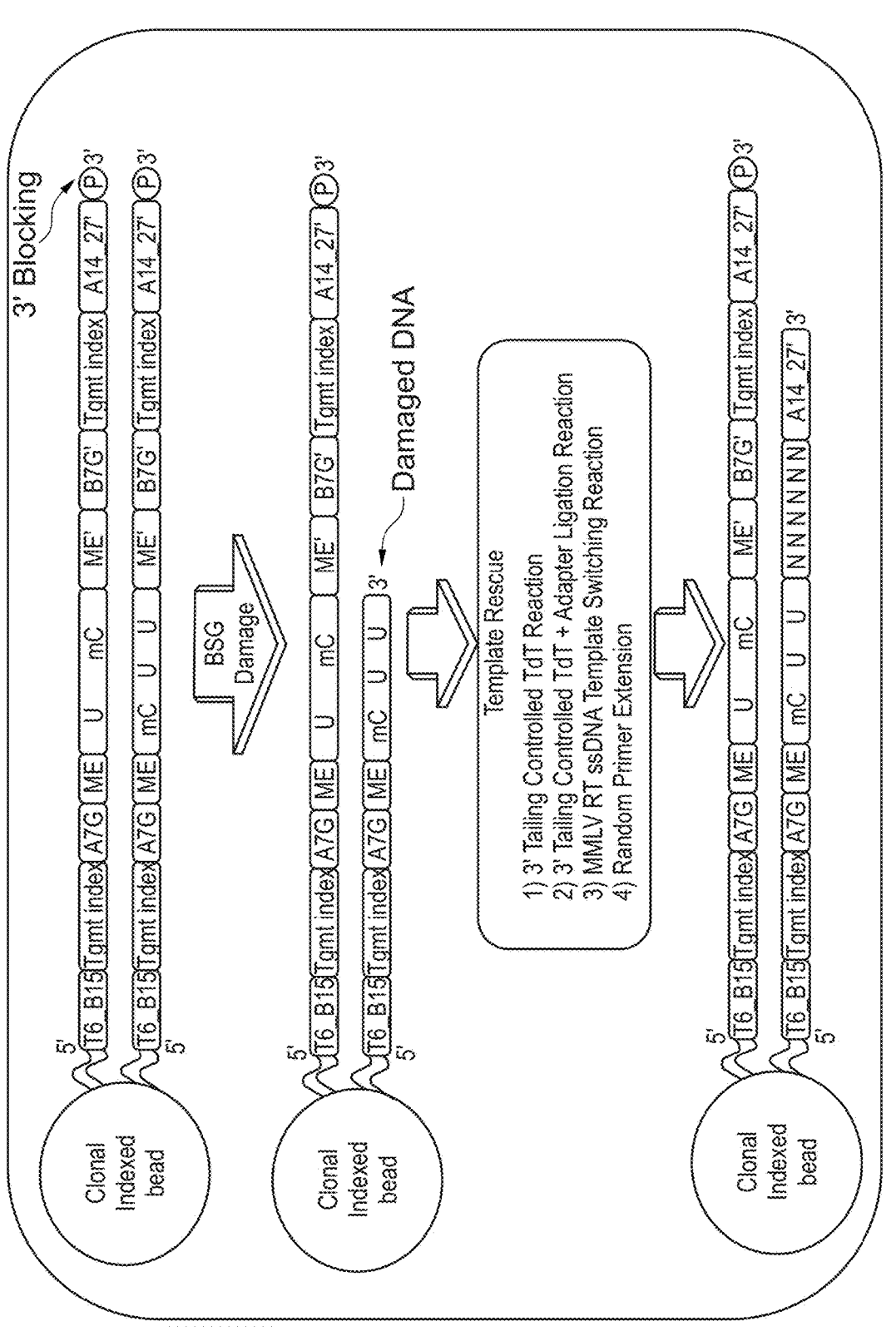
FIG. 67 shows an exemplary scheme to improve DNA yield of the Epi-CPTSeq protocol using enzymatic methods for recovery of broken library elements after bisulfite treatment.

Example 19—Decreasing Library Insert Size by More Densely Populating Transposome Complexes to the Streptavidin Beads Streptavidin magnetic beads were loaded with 1×, 6×, and 12× concentrations of TsTn5 transposome complex. The Epi-CPT seq protocol was performed for each bead type. The final PCR product was loaded on the Agilent BioAnalyzer for analysis and shown in FIG. 66. Epi-CPT seq libraries fragments are smaller and have greater yield when more TsTn5 is loaded on beads.

Example 20—Fragmentation of DNA Library During Sodium Bisulfite Conversion

Figure 70:
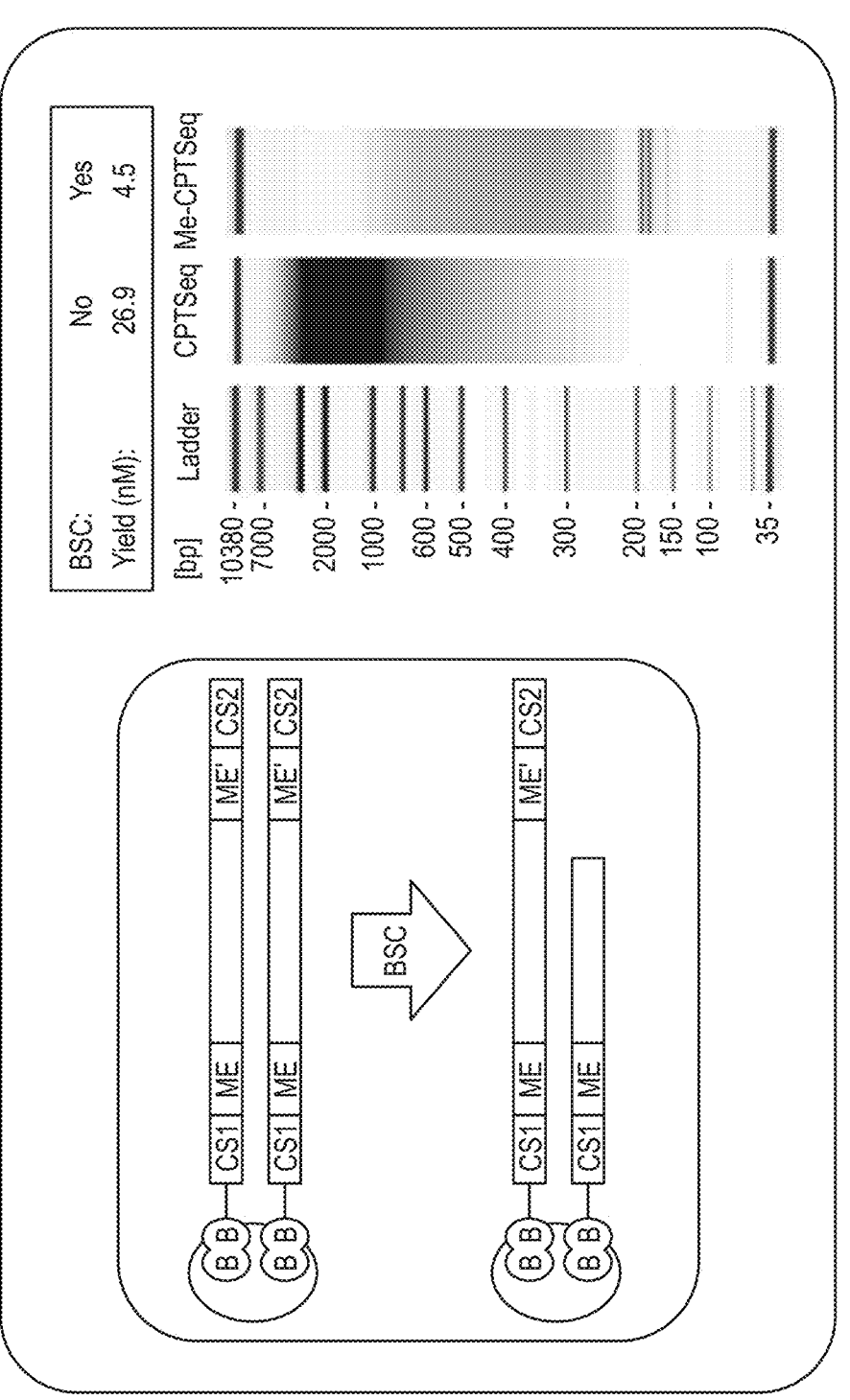
FIG. 70 shows the Fragmentation of DNA library during sodium bisulfate conversion. Left panel illustrates fragmentation during bisulfate conversion of a portion of DNA tagmented on magnetic beads. Right panel shows the Bio-Analyzer traces of CPTSeq and Epi-CPTSeq (Me-CPTSeq) libraries.

After bisulfite conversion, DNA becomes damaged, resulting in loss of the common sequences (CS2) needed for PCR amplification. DNA fragments CPTSeq and Epi-CPT-Seq (Me-CPTSeq) libraries were analyzed by BioAnalyzer. Due to DNA damage during bisulfite conversion, the Epi-CPTSeq library has 5-fold lower yield and a smaller library size distribution compared to the CPTSeq library as shown in FIG. 70.

Example 21—TdT Mediated ssDNA Ligation Reaction

Figure 71:
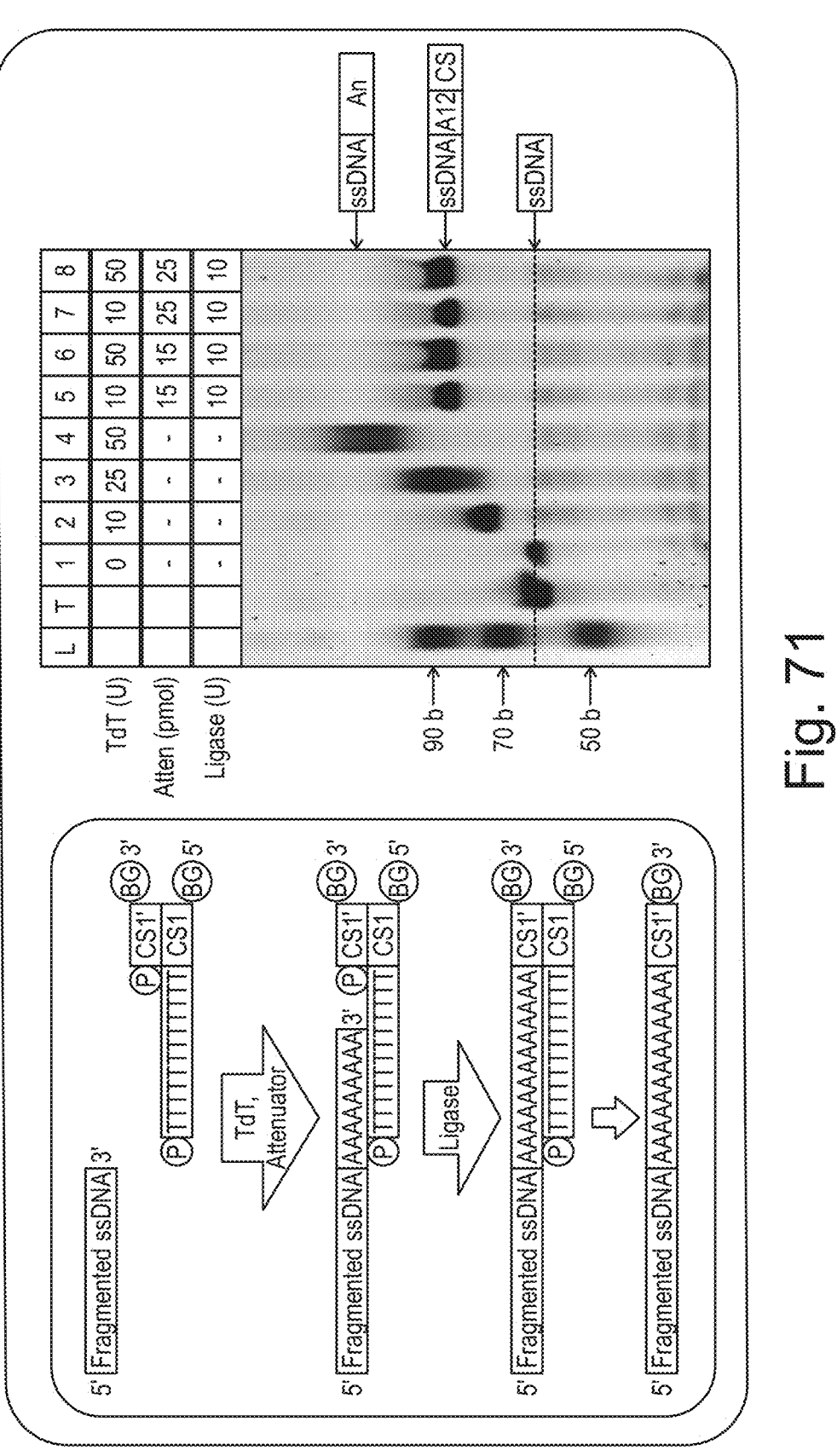
FIG. 71 shows an exemplary scheme and the results of TdT mediated ssDNA ligation reaction.

Feasibility of the DNA end-recovery by Terminal transferase (TdT) mediated ligation was tested. Briefly, 5 pmoles of ssDNA template was incubated with TdT (10/50U), Attenuator/adapter duplex (0/15/25 pmoles) and DNA Ligase (0/10U) were incubated for 15 m at 37 C. DNA products of extension/ligation were analyzed on a TBE-Urea gel and the results were shown in FIG. 71. Addition of all reaction components resulted in almost complete ligation of the adapter molecule (Lanes 5-8).

Figure 72:
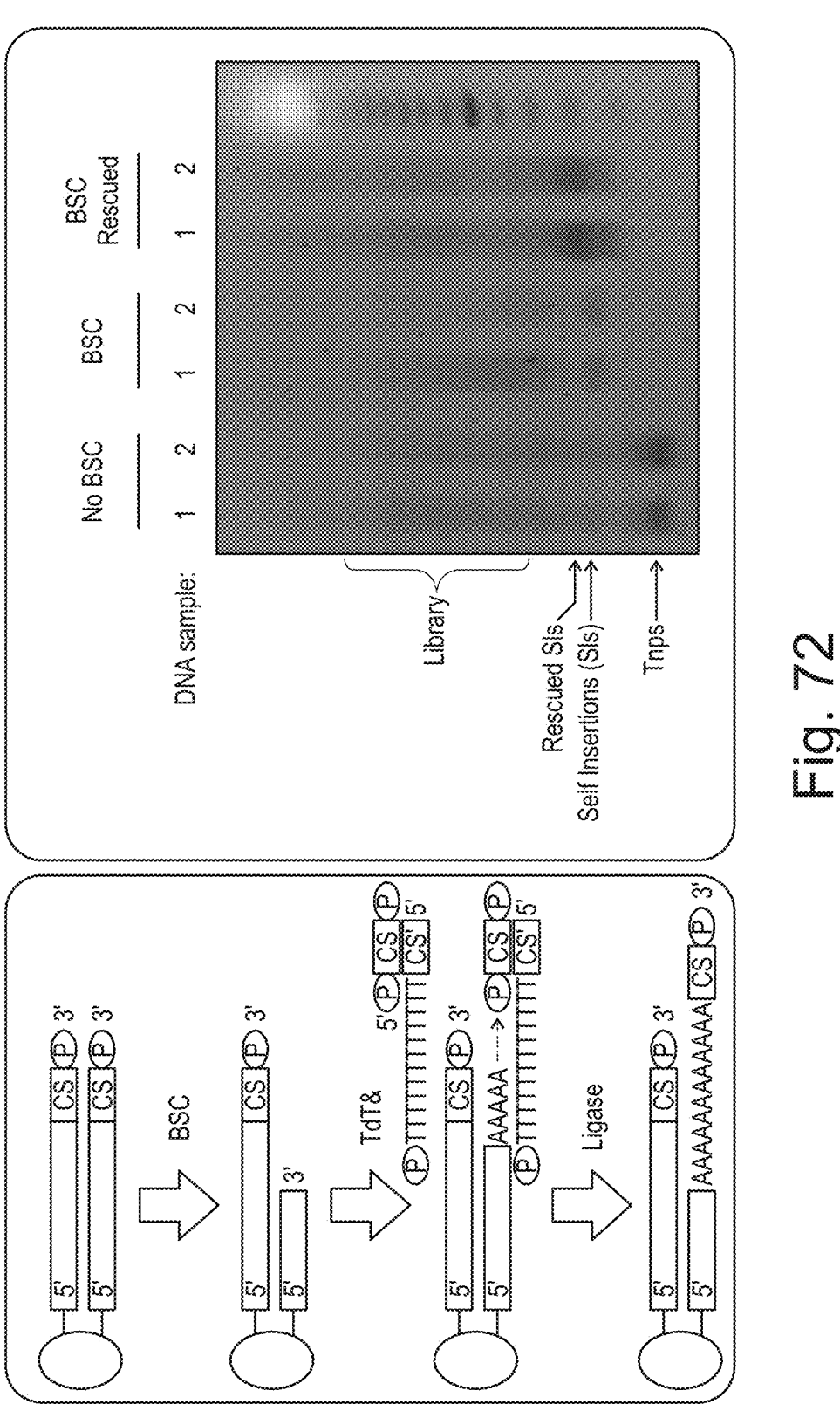
FIG. 72 shows a scheme and the results of TdT mediated recovery of sodium bisulfate converted bead bound library. Left panel illustrates the rescue workflow of damaged bisulfite converted DNA library using TdT mediated ligation reaction (SEQ ID NOS 7, 7, and 9, respectively, in order of appearance). Results of DNA library rescue experiment are shown in the right panel.

Feasibility of the DNA end-recovery by Terminal transferase (TdT) mediated ligation was tested for sodium bisulfate converted bead bound library and shown in FIG. 72. Briefly, DNA was tagmented on beads (first two lanes), treated with Promega's MethylEdge bisulfate conversion kit (lanes 3 and 4) and subjected to DNA rescue protocol (lanes 5 and 6). There is an obvious increase in yield and size of DNA library after rescue reaction. There is also an increase in abundance of self inserted transposons (SIs) indicating efficient ligation of the adapter molecule.

Figure 73:
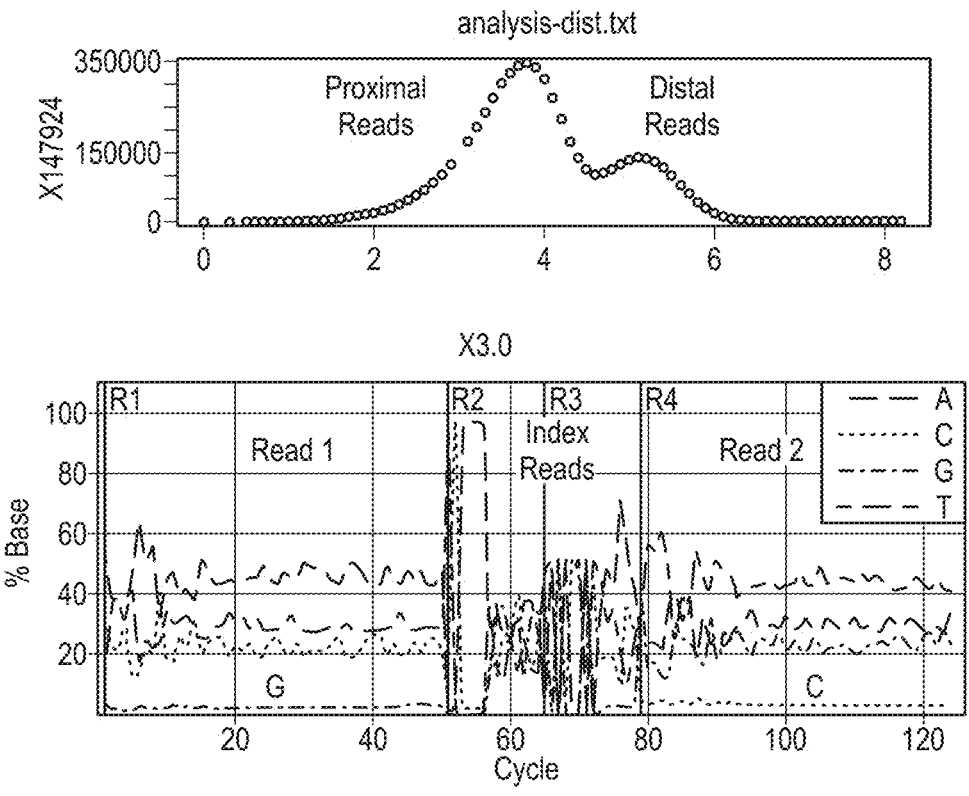
FIG. 73 shows the results of Methyl-CPTSeq assay.

Results of Methyl-CPTSeq assay are presented in FIG. 73.

---

What is claimed is:

1. A method for maintaining contiguity information of a double-stranded target nucleic acid, the method comprising:

(a) providing a plurality of solid supports each having a plurality of transposome complexes immobilized thereon, wherein the plurality of transposome complexes each comprises more than one transposome monomeric unit, wherein a first transposome monomeric units is linked to a second transposome monomeric unit to form an individual transposome complex, and wherein an individual transposome monomeric unit comprises a transposase bound to a polynucleotide, said polynucleotide comprising:

(i) a 3' portion comprising a transposon end sequence, and (ii) a first adaptor comprising a first barcode sequence;

(b) applying double-stranded target nucleic acids to the plurality of solid supports, wherein the plurality of transposome complexes on a respective solid support of the plurality of solid supports bind to a plurality of portions of an individual double-stranded target nucleic acid under conditions whereby the individual double-stranded target nucleic acid is fragmented into double-stranded target nucleic acid fragments by the plurality of transposome complexes such that the contiguity of the individual double-stranded target nucleic acid is maintained, wherein the transposon end sequence of the polynucleotide is transferred to a 5' end of at least one strand of the double-stranded target nucleic acid fragments, thereby producing an immobilized library of double-stranded target nucleic acid fragments wherein at least the one strand is 5'-tagged with the first barcode sequence, wherein a plurality of first barcode sequences on the respective solid support comprise the same nucleic acid sequence, and wherein a nucleic acid sequence of the plurality of first barcode sequences on the respective solid support differs from a nucleic acid sequence of a plurality of first barcode sequences from other solid supports of the plurality of solid supports;

(c) determining a sequence based on the double-stranded target nucleic acid fragments and associated first barcode sequences; and (d) determining the contiguity information of the double-stranded target nucleic acids by identifying the first barcode sequences.

2. The method of claim 1, wherein the contiguity information of the double-stranded target nucleic acid is indicative of genomic variants selected from the group consisting of deletions, translocations, interchromosomal gene fusions, duplications, and paralogs.

3. The method of claim 1, wherein the double-stranded target nucleic acid fragments comprising the first barcodes are amplified prior to determining the sequence of the target nucleic acid fragments.

4. The method of claim 1, wherein plurality of solid supports comprises beads.

5. The method of claim 1, wherein the first adaptor further comprises a first primer binding sequence.

6. The method of claim 1, wherein the double-stranded target nucleic acid is from a single cell.

7. The method of claim 1, wherein the double-stranded target nucleic acid is from a single organelle.

8. The method of claim 1, wherein the double-stranded target nucleic acid comprises genomic DNA.

9. The method of claim 1, wherein the double-stranded target nucleic acid is cross-linked to another nucleic acid.

10. The method of claim 1, wherein the double-stranded target nucleic acid comprises cell-free tumor DNA.

11. The method of claim 1, wherein the double-stranded target nucleic acid comprises cDNA.

* * * * *